United States Patent
Beller et al.

(10) Patent No.: US 11,078,499 B2
(45) Date of Patent: Aug. 3, 2021

(54) HOST CELLS AND METHODS FOR PRODUCING TOLUENE BIOCHEMICALLY

(71) Applicants: Harry R. Beller, Berkeley, CA (US); Andria V. Rodrigues, Oakland, CA (US); Kamrun Zargar, Rocklin, CA (US)

(72) Inventors: Harry R. Beller, Berkeley, CA (US); Andria V. Rodrigues, Oakland, CA (US); Kamrun Zargar, Rocklin, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 16/286,411

(22) Filed: Feb. 26, 2019

(65) Prior Publication Data

US 2020/0270642 A1 Aug. 27, 2020
US 2021/0002671 A9 Jan. 7, 2021

Related U.S. Application Data

(60) Provisional application No. 62/636,066, filed on Feb. 27, 2018.

(51) Int. Cl.
*C12P 5/00* (2006.01)
*C12N 9/14* (2006.01)
*C12N 15/79* (2006.01)
*C12N 1/38* (2006.01)

(52) U.S. Cl.
CPC ............. *C12P 5/005* (2013.01); *C12N 1/38* (2013.01); *C12N 9/14* (2013.01); *C12N 15/79* (2013.01)

(58) Field of Classification Search
None
See application file for complete search history.

(56) References Cited

PUBLICATIONS

Beller HR et al. Discovery of enzymes for toluene synthesis from anoxic microbial communities. 2018. vol. 14. p. 451-457. (Year: 2018).*
Gerlt et al., "The Enzyme Function Initiative." Biochemistry 50, 9950-9962 (2011).
Anton et al., "The COMBREX project: design, methodology, and initial results." PLoS Biol. 11, e1001638 (2013).
Lespinet et al., "Orphan enzymes?" Science 307, 42 (2005).
Sorokina et al., "Profiling the orphan enzymes." Biol. Direct 9, 10 (2014).
Jüttner et al., "Anoxic hypolimnion is a significant source of biogenic toluene." Nature 323, 797-798 (1986).
Zargar et al., "In vitro characterization of phenylacetate decarboxylase, a novel enzyme catalyzing toluene biosynthesis in an anaerobic microbial community." Scientific Reports 6: 31362 (2016), 10 pages.
Fischer-Romero et al., "*Tolumonas auensis* gen. nov., sp. nov., a toluene-producing bacterium from anoxic sediments of a freshwater lake." Int. J. Syst. Bacteriol. 46:183-188 (1996).
Pons et al., "Biosynthesis of toluene in Clostridium aerofoetidum strain WS", Ann. Microbiol. (Paris) 135B, 219-222 (1984), Eng abstract.
Akhtar et al., "Carboxylic acid reductase is a versatile enzyme for the conversion of fatty acids into fuels and chemical commmodities." Proc. Natl. Acad. Sci. U S A 110, 87-92 (2013).
Schirmer et al., "Microbial biosynthesis of alkanes". Science 329: 559-562 (2010).
Selmer et al., "p-Hydroxyphenylacetate decarboxylase from Clostridium difficile. A novel glycyl radical enzyme catalysing the formation of p-cresol." Eur. J. Biochem. 268, 1363-1372 (2001).
Yu et al., 4-Hydroxyphenylacetate decarboxylases: properties of a novel subclass of glycyl radical enzyme systems. Biochemistry 45: 9584-9592 (2006).
Selmer et al., "New glycyl radical enzymes catalysing key metabolic steps in anaerobic bacteria." Biol. Chem. 386, 981-988 (2005).
Leuthner et al., "Biochemical and genetic characterization of benzylsuccinate synthase from Thauera aromatica: a new glycyl radical enzyme catalysing the first step in anaerobic toluene metabolism." Mol. Microbiol. 28, 615-628 (1998).
O'Brien et al., "Insight into the mechanism of the B12-independent glycerol dehydratase from Clostridium butyricum: preliminary biochemical and structural characterization." Biochemistry 43, 4635-4645 (2004).
Beller et al., Substrate range of benzylsuccinate synthase from *azoarcus* sp. strain T. FEMS Microbiol. Lett. 178, 147-153 (1999).
Becker et al., "Structure and mechanism of the glycyl radical enzyme pyruvate formate-lyase." Nat. Stud. Biol. 6, 969-975 (1999).
Larsson et al., "Structural basis for allosteric substrate specificity regulation in anaerobic ribonucleotide reductases." Structure 9, 739-750 (2001).
Heider et al., "Anaerobic bacterial metabolism of hydrocarbons." FEMS Microbiology Reviews 22, 459-473 (1998).
Feliks et al., "Catalytic mechanism of the glycyl radical enzyme 4-hydroxyphenylacetate decarboxylase from continuum electrostatic and QC/MM calculations." J. Am. Chem. Soc. 135, 14574-14585 (2013).
Kalnins et al., "Structure and function of CutC choline lyase from human microbiota bacterium Klebsiella pneumoniae." J Biol Chem 290, 21732-21740 (2015).

(Continued)

*Primary Examiner* — Paul J Holland
(74) *Attorney, Agent, or Firm* — Robin C. Chiang; Lawrence Berkeley National Laboratory

(57) ABSTRACT

The present invention provides for a genetically modified host cell comprising a first polypeptide comprising a sequence having at least 70% amino acid sequence identity with a phenylacetate decarboxylase, and having an enzymatic activity to decarboxylate a phenylacetic acid into a toluene and a carbon dioxide, and a second polypeptide comprising a sequence having at least 70% amino acid sequence identity with a phenylacetate decarboxylase activating enzyme, and having an enzymatic activity to cleave a S-adenosylmethionine (SAM) to form a methionine and a 5'-deoxyadenosyl radical.

13 Claims, 12 Drawing Sheets

Specification includes a Sequence Listing.

(56) References Cited

PUBLICATIONS

Craciun et al., "Microbial conversion of choline to trimethylamine requires a glycyl radical enzyme." Proc. Natl. Acad. Sci. U S A 109, 21307-21312 (2012).
Levin et al., "A prominent glycyl radical enzyme in human gut microbiomes metabolizes trans-4-hydroxy-l-proline." Science 355 (2017), 11 pages.
Funk et al., "Substrate-bound structures of benzylsuccinate synthase reveal how toluene is activated in anaerobic hydrocarbon degradation." J. Biol. Chem. 290, 22398-22408 (2015).
Martins et al., "Structural basis for a Kolbe-type decarboxylation catalyzed by a glycyl radical enzyme." J. Am. Chem. Soc. 133, 14666-14674 (2011).
Kielak et al., "The Ecology of Acidobacteria: Moving beyond Genes and Genomes." Front. Microbiol. 7, 744 (2016).
Ward et al., "Three genomes from the phylum Acidobacteria provide insight into the lifestyles of these microorganisms in soils." Appl. Environ. Microbiol. 75, 2046-2056 (2009).
Altschul et al., "Basic local alignment search tool." J. Mol. Biol. 215, 403-410 (1990).
Dawson et al., "Assessing the role of p-cresol tolerance in Clostridium difficile." J. Med. Microbiol. 57, 745-749 (2008).
Schneider et al., "Anaerobic metabolism of L-phenylalanine via benzoyl-CoA in the denitrifying bacterium Thauera aromatica." Arch. Microbiol. 168, 310-320 (1997).
Carmona et al., "Anaerobic catabolism of aromatic compounds: a genetic and genomic view." Microbiol. Mol. Biol. Rev. 73, 71-133 (2009).
Molenaar et al., "Generation of a proton motive force by histidine decarboxylation and electrogenic histidine/histamine antiport in Lactobacillus buchneri." J Bacteriol 175, 2864-2870 (1993).
Pereira et al., "Dual role for the tyrosine decarboxylation pathway in Enterococcus faecium E17: response to an acid challenge and generation of a proton motive force." Appl Environ Microbiol 75, 345-352 (2009).
Beller et al., "Genetic manipulation of the obligate chemolithoautotrophic bacterium Thiobacillus denitrificans." Methods Mol. Biol. 881, 99-136 (2012).
Huntemann et al., "The standard operating procedure of the DOE-JGI Microbial Genome Annotation Pipeline (MGAP v.4)." Stand. Genomic Sci. 10, 86 (2015).
Edgar, "UPARSE: highly accurate OTU sequences from microbial amplicon reads." Nat. Methods 10, 996-998 (2013).
Quast et al., "The SILVA ribosomal RNA gene database project: improved data processing and web-based tools." Nucleic Acids Res. 41, D590-D596 (2013).
Studier, "Protein production by auto-induction in high density shaking cultures." Protein Expr. Purif. 41, 207-234 (2005).
Gao et al., "*Arabidopsis thaliana* Nfu2 accommodates [2Fe—2S] or [4Fe—4S] clusters and is competent for in vitro maturation of chloroplast [2Fe—2S] and [4Fe—4S] cluster-containing proteins." Biochemistry 52, 6633-6645 (2013).
Mackay et al., "A critical review of Henry's Law constants for chemicals of environmental interest." Journal of Physical and Chemical Reference Data 10, 1175-1199 (1981).
Grant et al., "FIMO: scanning for occurrences of a given motif." Bioinformatics 27, 1017-1018 (2011).
Edgar, "Muscle: multiple sequence alignment with high accuracy and high throughput." Nucleic Acids Res. 32, 1792-1797 (2004).
Stamatakis, "RAxML version 8: a tool for phylogenetic analysis and post-analysis of large phylogenies." Bioinformatics 30, 1312-1313 (2014).
Letunic et al., "Interactive tree of life (iTOL) v3: an online tool for the display and annotation of phylogenetic and other trees." Nucleic Acids Res. 44, W242-245 (2016).
Bankevich et al., SPAdes: a new genome assembly algorithm and its applications to single-cell sequencing. J. Comput. Biol. 19, 455-477 (2012).
Wu et al., "MaxBin 2.0: an automated binning algorithm to recover genomes from multiple metagenomic datasets." Bioinformatics 32, 605-607 (2016).
Hyatt et al., "Prodigal: prokaryotic gene recognition and translation initiation site identification." BMC bioinformatics 11, 119 (2010) 11 pages.
Parks et al., "CheckM: assessing the quality of microbial genomes recovered from isolates, single cells, and metagenomes." Genome Res. 25, 1043-1055 (2015).
Krzywinski et al., Circos: an information aesthetic for comparative genomics. Genome Res. 19, 1639-1645 (2009).
Price et al., "FastTree: computing large minimum evolution trees with profiles instead of a distance matrix." Mol. Biol. Evol. 26, 1641-1650 (2009).
Biasini et al., "Swiss-Model: modelling protein tertiary and quaternary structure using evolutionary information." Nucleic Acids Research 42, W252-258 (2014).
Emsley et al., "Coot: model-building tools for molecular graphics." Acta Crystallogr. D Biol. Crystallogr. 60, 2126-2132 (2004).
Vagin et al., "REFMAC5 dictionary: organization of prior chemical knowledge and guidelines for its use." Acta Cristallogr. D Biol. Crystallogr. 60, 2184-2195 (2004).
Davis et al., "MolProbity: all-atom contacts and structure validation for proteins and nucleic acids." Nucleic Acids Research 35, W375-383 (2007).
Sievers et al., "Fast, scalable generation of high-quality protein multiple sequence alignments using Clustal Omega." Mol. Syst. Biol. 7, 539 (2011).
Takabayashi et al., "The Oligomeric States of the Photosystems and the Light-Harvesting Complexes in the Chl b-Less Mutant" Plant Cell Physiol. 52(12): 2103-2114 (2011).
Beller et al., "Discovery of enzymes for toluene synthesis from anoxic microbial communities" Nature Chemical Biol, 14: 451-457 (2018).

\* cited by examiner b
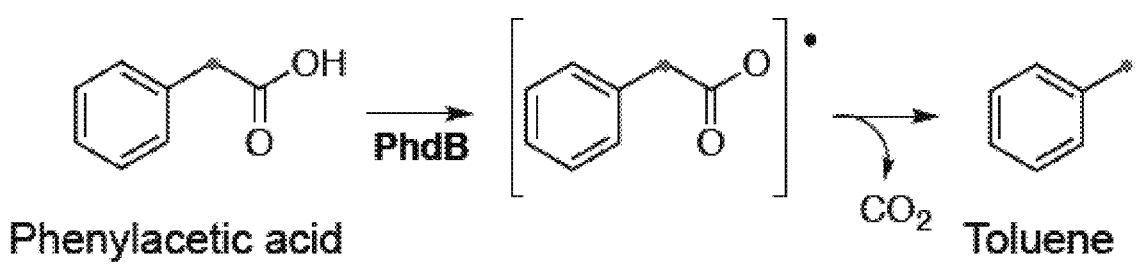
Phenylacetic acid → [intermediate] → Toluene + $CO_2$ (via PhdB)
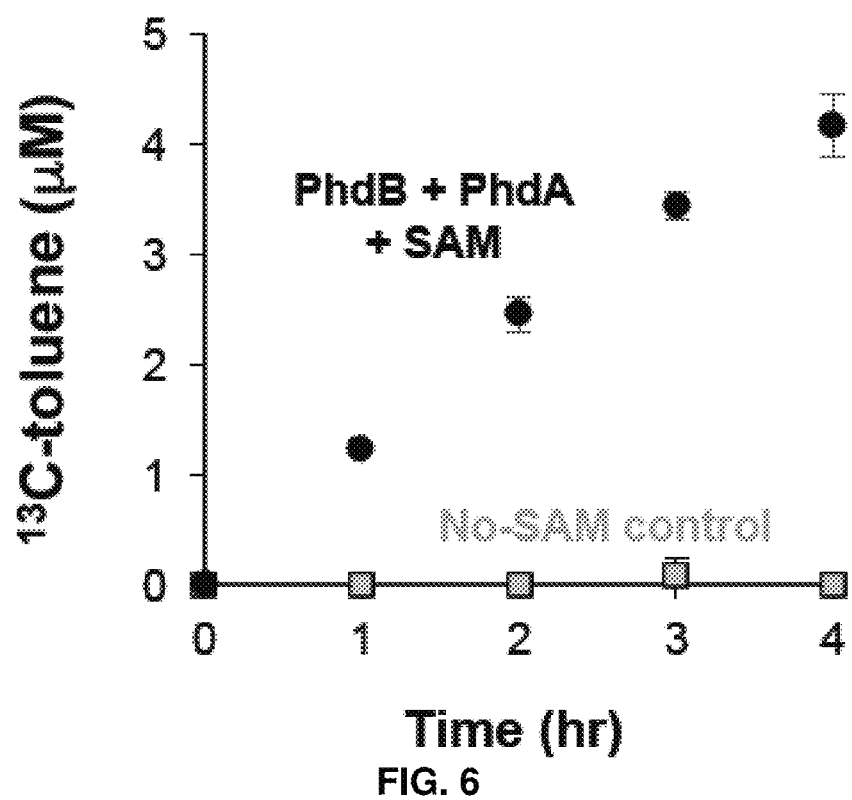
FIG. 6 a

| | | |
|---|---|---|
| PflB | MLLDAMENPEKYPQLTIRVSGYAVRFNSLTKEQQQDVITRTFTQSM | 760 |
| CsdB | TLRDAQLTPEKYRELMVRVAGFTQYWCEIGKPIQDEVIYRTEYDK | 897 |
| BssA | EMRAAQREPEKHHDLIVRVSGYSARFVDIPTYGQNTIIARQEQDFSASDL | 857 |
| Gdh | ILLAAQKNPEKYQDLIVRVAGYSAQFISLDKSIQNDIIARTEHVM | 787 |
| CutC | VLKKAQQEPEKYRDLIVRVAGYSAYFVELCKEVQDEIISRTVIEKF | 1128 |
| HypD | VLLEAQKNPQDYKDLIVRVAGYSDHFNNLSRTLQDEIIGRTEQTF | 789 |
| PhdB-s | TLRAAQKDPDSYRDLIVRVAGFSAYFITLCPEVQDEIVSRTCQTW | 839 |
| PhdB-l | TLRAAQKDPDSFRDLIVRVAGFSAYFITLCPEVQNEIVSRTSQQW | 839 | b

| | | |
|---|---|---|
| PflB | DDYAIACCVSPMIVG----------KQM-----QF------FGARANLAKTML | 444 |
| CsdB | RAWCLGGCLESAPGCFLPLEYNGKVTMIPGGASPTCGTGVNFIGMPKVLE | 545 |
| BssA | HNWVNVLCMSPGIHG----------RRK-----TQKTRSEGGGSIFPAKLLE | 521 |
| Gdh | RDYGIIGCVEPQKPG----------KTE-----GWH------DSAFFNLARIVE | 458 |
| CutC | RDYCLMGCVEPQKSG----------RIY-----QWT----STGYTQWPIAIE | 796 |
| HypD | RLGGTSGCVETGCPG----------K-E-----AYV----LTGYMNIPKILE | 458 |
| PhdB-s | RDQAVAGCVQSIIGG----------KTD-----GP------WEARFNMTKMME | 506 |
| PhdB-l | RDQAVAGCVQSIIGG----------KTD-----GT------WEARFNMCKMIE | 506 | c

| | | |
|---|---|---|
| NrdG | MNYHQYYPVDIVNGPGTRCTLFVSGCVHECPGCYNKS | 37 |
| BssD | MKIPLITEIQRFSLDGPGIRTTIFLKGCPLRCPWCHNPE | 40 |
| PflA | MSVIGRIHSFESCGTVDGPGIRFITFFQGCLMRCLYCHNRD | 36 |
| CutD | MIAKQELTGRIFNIQKYSIYDGDIRTLVFFKGCNIRCPWCANPE | 45 |
| CsdA | MKEKGLIFDIQSFSVHDGPGCRTSVFFIGCPLQCKWCANPE | 41 |
| GD-AE | MSKEIKGVLFNIQKFSLHDGPGIRTIVFFKGCSMSCLRCSNPE | 43 |
| HypD-AE | MNPLVINLQKCSIHDGPGIRSTVFFKGCPLECVWCHNPE | 39 |
| PhdA-s | MGTNELTGMVFNIQGYSVQDGPGIRPTVFLKGCPLRCLRCSNPE | 44 |
| PhdA-l | MGTSELTGTNELTGMVFNIQGYSIQDGPGIRTTIFLKGCPLRCLWCSNPE | 50 |

FIG. 11

HOST CELLS AND METHODS FOR PRODUCING TOLUENE BIOCHEMICALLY

CROSS-REFERENCE TO RELATED APPLICATIONS

This application claims priority to U.S. Provisional Patent Application Ser. No. 62/636,066, filed on Feb. 27, 2018, which is hereby incorporated by reference.

STATEMENT OF GOVERNMENTAL SUPPORT

The invention was made with government support under Contract Nos. DE-AC02-05CH11231 awarded by the U.S. Department of Energy. The government has certain rights in the invention.

FIELD OF THE INVENTION

The present invention is in the field of producing toluene, in particular from renewable, non-petroleum sources.

BACKGROUND OF THE INVENTION

The extraordinary metabolic diversity of microorganisms in combination with ready access to increasingly rapid and less expensive DNA sequencing technologies has revealed a well-recognized challenge in modern biology: the dearth of experimental evidence to support functional annotation of a large fraction of genes/proteins in public data repositories[1-3]. A related challenge, termed "orphan enzymes"[4], is the abundance of unambiguously defined enzymatic activities that are not linked with specific amino acid sequences; in 2014, 22% of defined EC (Enzyme Commission) numbers were orphan enzymes[5]. To the extent that specific enzymes can be better linked to a broad range of chemically diverse reactions, the scope and versatility of biochemical transformations harnessed for biotechnological applications will be enhanced. One area in which knowledge of enzymes is very limited is biosynthesis of aromatic hydrocarbons, which could be useful as renewable fuels or chemicals made from non-petroleum feedstocks. Currently, the only known aromatic hydrocarbon that can currently be synthesized wholly from known enzymes is styrene, which can be produced from phenylalanine-derived trans-cinnamic acid by enzymes displaying phenylacrylate decarboxylase activity, such as FDC1 from *Saccharomyces cerevisiae*[6]. There is a need for the discovery of other enzymes for the purpose of synthesizing other aromatic hydrocarbons.

SUMMARY OF THE INVENTION

The present invention provides for a genetically modified host cell comprising a first polypeptide comprising a sequence having at least 70% amino acid sequence identity with SEQ ID NO:1 or SEQ ID NO:2, and having an enzymatic activity to decarboxylate a phenylacetic acid into a toluene and a carbon dioxide, and a second polypeptide comprising a sequence having at least 70% amino acid sequence identity with SEQ ID NO:3 or SEQ ID NO:4, and having an enzymatic activity to cleave a S-adenosylmethionine (SAM) to form a methionine and a 5'-deoxyadenosyl radical.

The present invention provides for a genetically modified host cell comprising a first nucleic acid encoding the first polypeptide comprising a sequence having at least 70% amino acid sequence identity with SEQ ID NO:1 or SEQ ID NO:2, and having an enzymatic activity to decarboxylate a phenylacetic acid into a toluene and a carbon dioxide; and optionally the first nucleic acid, or a second nucleic acid, encoding the second polypeptide comprising a sequence having at least 70% amino acid sequence identity with SEQ ID NO:3 or SEQ ID NO:4, and having an enzymatic activity to cleave a S-adenosylmethionine (SAM) to form a methionine and a 5'-deoxyadenosyl radical; wherein the genetically modified host cell is capable of expressing the first and/or the second polypeptide. In some embodiments, the genetically modified host cell is capable of endogenously synthesizing the SAM and/or an unsubstituted or substituted phenylacetic acid.

In some embodiments, the first and/or second nucleic acids comprise a promoter operatively linked to the open reading frame(s) of the first and/or second polypeptides. In some embodiments, the host cell is a non-human cell. In some embodiments, the first and/or second polypeptides are heterologous to the genetically modified host cell and/or promoter.

In some embodiments, the host cell lacks the expression of the tyrA, tyrB and/or tyrR genes, or is knocked out for one or more endogenous of the following endogenous genes: the tyrA, tyrB and/or tyrR genes. In some embodiments, the host cell expresses endogenous genes encoding phenylpyruvate decarboxylase and/or phenylacetaldehyde dehydrogenase, or is modified to express one or more of heterologous genes encoding phenylpyruvate decarboxylase and/or phenylacetaldehyde dehydrogenase.

The present invention provides for a method of producing a substituted or unsubstituted toluene or 2-methyl-1H-indole in a genetically modified host cell. The method comprises culturing the genetically modified host cell in a medium under a suitable condition such that the culturing results in the genetically modified host cell producing the substituted or unsubstituted toluene or 2-methyl-1H-indole.

In some embodiments, the medium comprises SAM and/or an unsubstituted or substituted phenylacetic acid and the genetically modified host cell can uptake or absorb SAM and/or an unsubstituted or substituted phenylacetic acid from the medium. In some embodiments, the genetically modified host cell is capable of endogenously synthesizing SAM and/or an unsubstituted or substituted phenylacetic acid from a carbon source. In some embodiments, the method further comprises introducing the first and/or second nucleic acids into the genetically modified host cell, wherein the introducing step is prior to the culturing step. In some embodiments, the method further comprises separating the substituted or unsubstituted toluene or 2-methyl-1H-indole from the genetically modified host cell and/or the medium, wherein the separating step is subsequent, concurrent or partially concurrent with the culturing step.

The present invention further provides for a composition comprising an isolated substituted or unsubstituted toluene or 2-methyl-1H-indole produced from the method of the present invention, wherein the composition further comprises trace amounts of the genetically modified host cell, or parts thereof, and/or the medium.

BRIEF DESCRIPTION OF THE DRAWINGS

The foregoing aspects and others will be readily appreciated by the skilled artisan from the following description of illustrative embodiments when read in conjunction with the accompanying drawings.

FIG. 6. Reactions catalyzed by PhdB. Proposed reaction of PhdB with phenylacetic acid-2-$^{13}$C, as supported in vitro by [methyl-$^{13}$C]toluene production by partially purified PhdB in combination with PhdA and SAM (black circles). Controls without SAM are also shown (gray squares). $^{13}$C-labeled C atoms in the proposed reaction are highlighted with a red circle. Data points represent means and error bars represent one standard deviation (n=3). Experiments demonstrating labeled toluene production from labeled phenylacetate in the presence of PhdB were performed 6 times (four times with no-SAM negative controls).

FIG. 11. Multiple sequence alignments comparing PhdB and PhdA with other glycyl radical enzymes and glycyl radical activating enzymes, respectively. a, C-terminal region of GREs containing the conserved glycyl radical motif, with the glycyl radical site highlighted in red with an asterisk and other conserved residues in bold. b, mid-sequence region of GREs containing conserved, active-site cysteine residue (which bears the thioyl radical that interacts with the substrate), highlighted in red with an asterisk, along with other conserved residues shown in blue. c, N-Terminal region of activating enzymes highlighting the CxxxCxxC (SEQ ID NO:10) motif (highlighted with asterisks) coordinating with the [4Fe-45] cluster. Sequences used in these alignment comparisons include the following GREs and AEs [PDB (Protein Data Bank) or GenBank accession number]: PhdB-s (SEQ ID NO:1), PhdB-1 (SEQ ID NO:2), PhdA-s (SEQ ID NO:3), PhdA-1 (SEQ ID NO:4), PflB (GenBank: NP_415423) (SEQ ID NO:15), PflA (GenBank: NP_415422) (SEQ ID NO:16), CsdB (GenBank: ABB05046.1) (SEQ ID NO:17), CsdA (GenBank: 2580384209) (SEQ ID NO:18), BssA (PDB: 4PKC:A) (SEQ ID NO:19), BssD (GenBank: CAA05050.2) (SEQ ID NO:20), Gdh (PDB: 1R8W) (SEQ ID NO:21), GD-AE (GenBank: AAM54729) (SEQ ID NO:22), CutC (PDB: 5A0Z) (SEQ ID NO:23), CutD (GenBank: EP020361.1) (SEQ ID NO:24), HypD (UniProt: A0A031WDE4) (SEQ ID NO:25), HypD-AE (UniProt: A0A069AMK2) (SEQ ID NO:26), NrdG (GenBank: NP_418658) (SEQ ID NO:27). The "s" and "l" suffixes for PhdB and PhdA stand for sewage and lake, respectively. Alignment was performed with Clustal Omega[58].

DETAILED DESCRIPTION OF THE INVENTION

Figure 1:
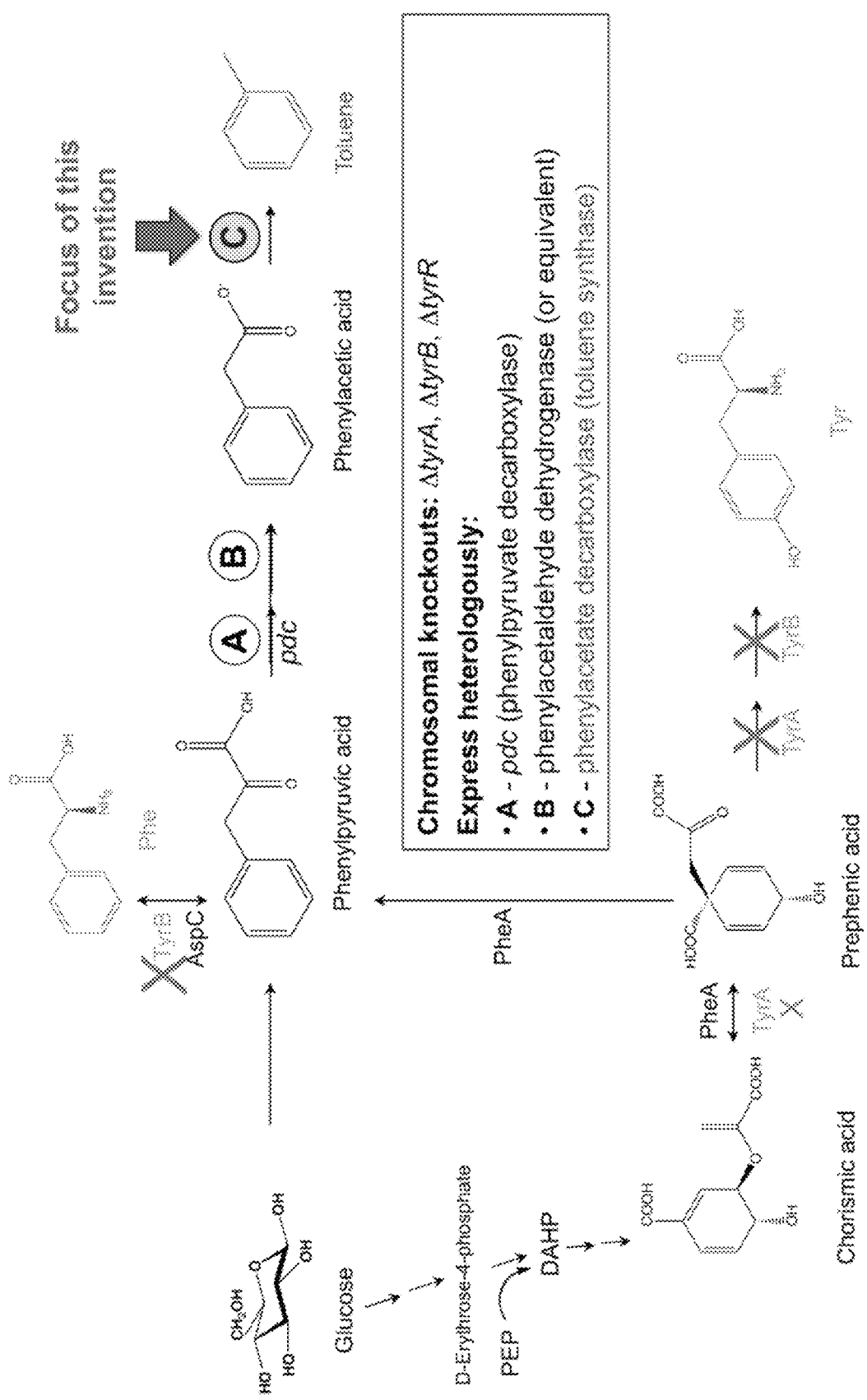
FIG. 1. Novel glycyl radical enzyme (PhdB) and cognate activase (PhdA) enable first-time biochemical toluene synthesis. In this specific example, the carbon source is glucose derived from a cellulosic biomass.
Figure 2:
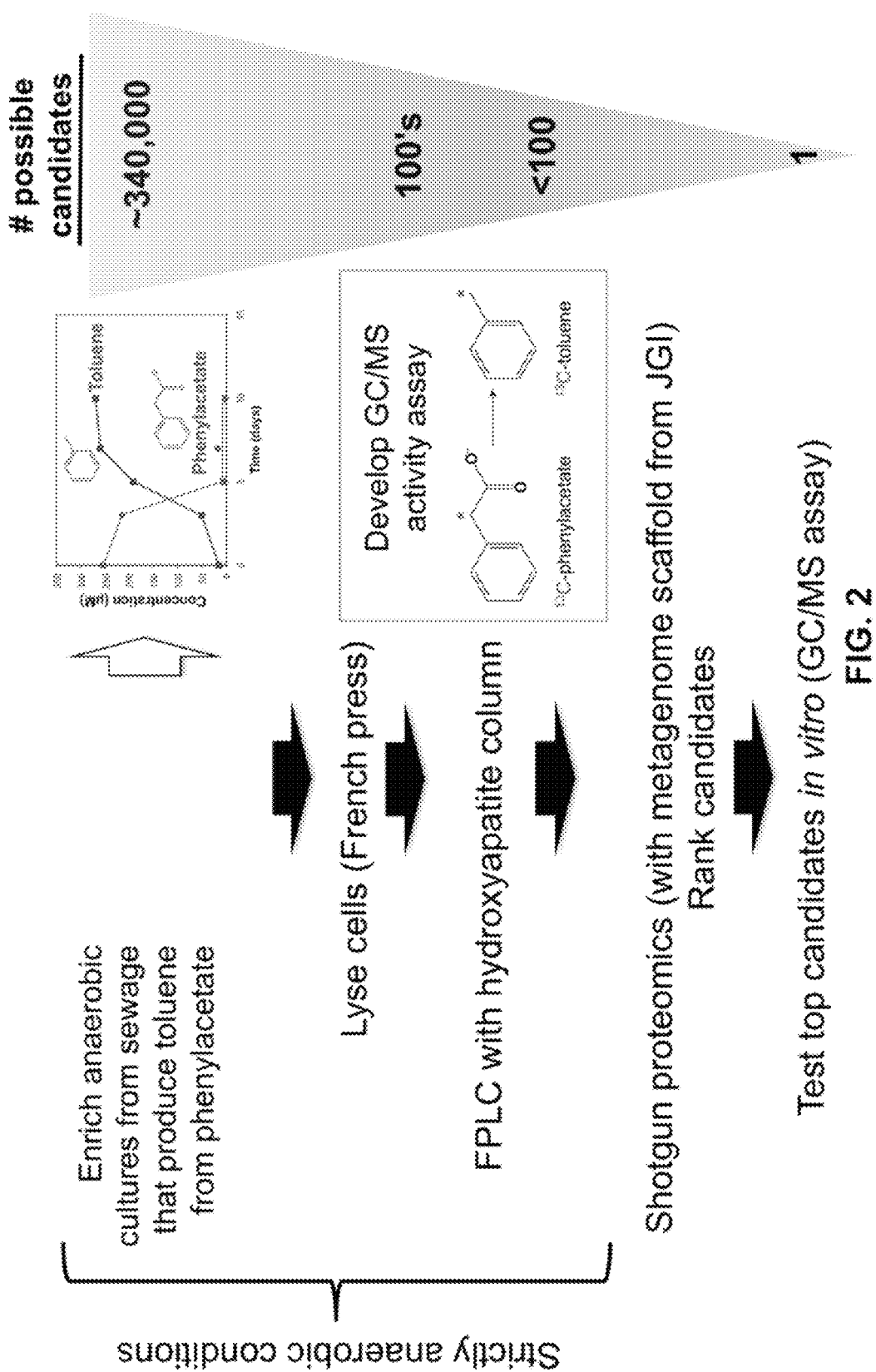
FIG. 2. Overview of activity-based enzyme discovery for phenylacetate decarboxylase, which catalyzes toluene biosynthesis.
Figure 3:
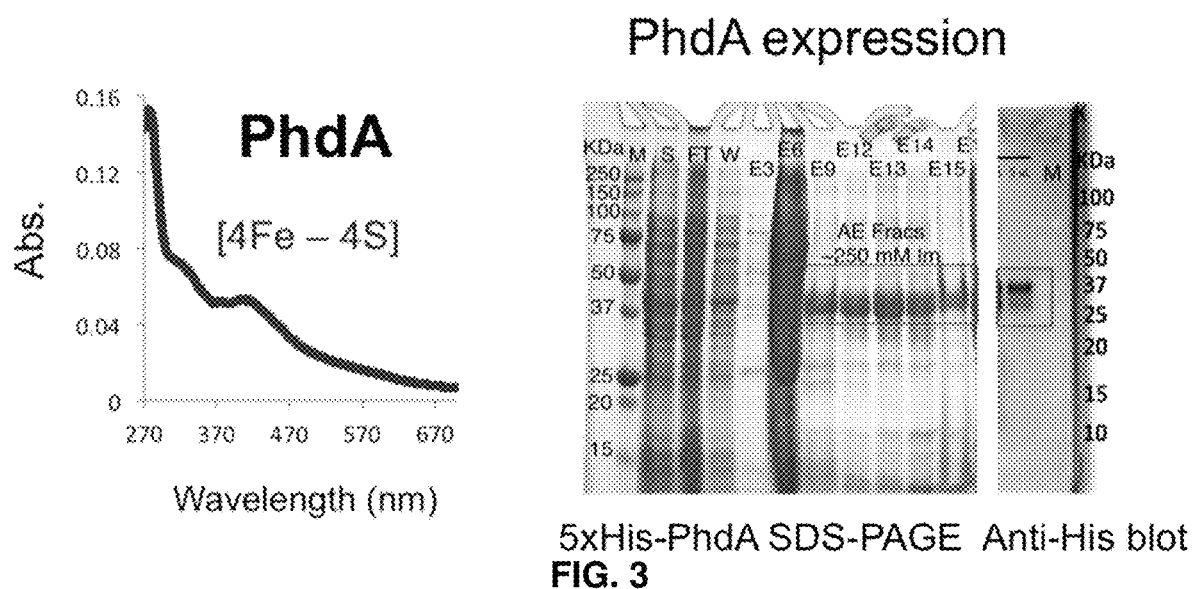
FIG. 3. Expression and purification of PhdA (phenylacetate decarboxylase activating enzyme).
Figure 4:
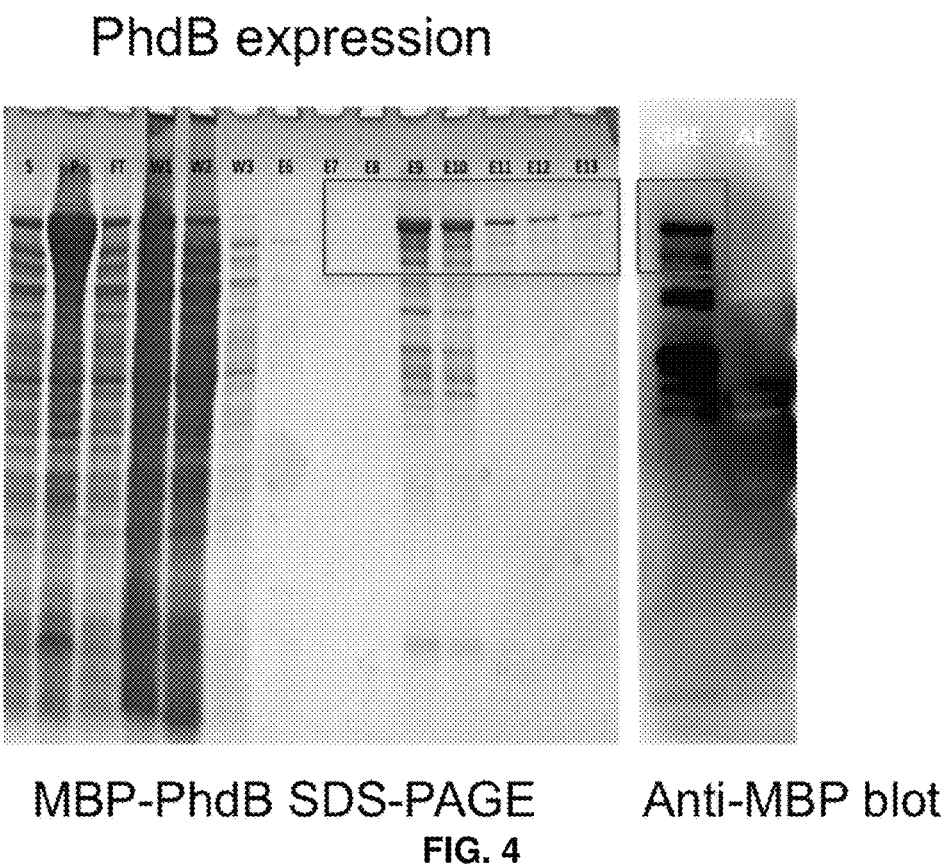
FIG. 4. Phenylacetate decarboxylase (PhdB) expression and purification.

Before the invention is described in detail, it is to be understood that, unless otherwise indicated, this invention is not limited to particular sequences, expression vectors, enzymes, host microorganisms, or processes, as such may vary. It is also to be understood that the terminology used herein is for purposes of describing particular embodiments only, and is not intended to be limiting.

In this specification and in the claims that follow, reference will be made to a number of terms that shall be defined to have the following meanings:

The terms "optional" or "optionally" as used herein mean that the subsequently described feature or structure may or may not be present, or that the subsequently described event or circumstance may or may not occur, and that the description includes instances where a particular feature or structure is present and instances where the feature or structure is absent, or instances where the event or circumstance occurs and instances where it does not.

As used in the specification and the appended claims, the singular forms "a," "an," and "the" include plural referents unless the context clearly dictates otherwise. Thus, for example, reference to an "expression vector" includes a single expression vector as well as a plurality of expression vectors, either the same (e.g., the same operon) or different; reference to "cell" includes a single cell as well as a plurality of cells; and the like.

In this specification and in the claims that follow, reference will be made to a number of terms that shall be defined to have the following meanings:

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

The term "about" refers to a value including 10% more than the stated value and 10% less than the stated value.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

The terms "host cell" and "host microorganism" are used interchangeably herein to refer to a living biological cell that can be transformed via insertion of an expression vector. Thus, a host organism or cell as described herein may be a prokaryotic organism (e.g., an organism of the kingdom Eubacteria) or a eukaryotic cell. As will be appreciated by one of ordinary skill in the art, a prokaryotic cell lacks a membrane-bound nucleus, while a eukaryotic cell has a membrane-bound nucleus.

The terms "expression vector" or "vector" refer to a compound and/or composition that transduces, transforms, or infects a host microorganism, thereby causing the cell to express nucleic acids and/or proteins other than those native to the cell, or in a manner not native to the cell. An "expression vector" contains a sequence of nucleic acids (ordinarily RNA or DNA) to be expressed by the host microorganism. Optionally, the expression vector also comprises materials to aid in achieving entry of the nucleic acid into the host microorganism, such as a virus, liposome, protein coating, or the like. The expression vectors contemplated for use in the present invention include those into which a nucleic acid sequence can be inserted, along with any preferred or required operational elements. Further, the expression vector must be one that can be transferred into a host microorganism and replicated therein. Particular expression vectors are plasmids, particularly those with restriction sites that have been well documented and that contain the operational elements preferred or required for transcription of the nucleic acid sequence. Such plasmids, as well as other expression vectors, are well known to those of ordinary skill in the art.

The terms "polynucleotide" and "nucleic acid" are used interchangeably and refer to a single or double-stranded polymer of deoxyribonucleotide or ribonucleotide bases read from the 5' to the 3' end. A nucleic acid of the present invention will generally contain phosphodiester bonds, although in some cases, nucleic acid analogs may be used that may have alternate backbones, comprising, e.g., phosphoramidate, phosphorothioate, phosphorodithioate, or O-methylphophoroamidite linkages (see Eckstein, Oligonucleotides and Analogues: A Practical Approach, Oxford University Press); positive backbones; non-ionic backbones, and non-ribose backbones. Thus, nucleic acids or polynucleotides may also include modified nucleotides that permit correct read-through by a polymerase. "Polynucleotide sequence" or "nucleic acid sequence" includes both the sense and antisense strands of a nucleic acid as either individual single strands or in a duplex. As will be appreciated by those in the art, the depiction of a single strand also defines the sequence of the complementary strand; thus the sequences described herein also provide the complement of the sequence. Unless otherwise indicated, a particular nucleic acid sequence also implicitly encompasses variants thereof (e.g., degenerate codon substitutions) and complementary sequences, as well as the sequence explicitly indicated. The nucleic acid may be DNA, both genomic and cDNA, RNA or a hybrid, where the nucleic acid may contain combinations of deoxyribo- and ribo-nucleotides, and combinations of bases, including uracil, adenine, thymine, cytosine, guanine, inosine, xanthine hypoxanthine, isocytosine, isoguanine, etc.

The term "promoter," as used herein, refers to a polynucleotide sequence capable of driving transcription of a DNA sequence in a cell. Thus, promoters used in the polynucleotide constructs of the invention include cis- and trans-acting transcriptional control elements and regulatory sequences that are involved in regulating or modulating the timing and/or rate of transcription of a gene. For example, a promoter can be a cis-acting transcriptional control element, including an enhancer, a promoter, a transcription terminator, an origin of replication, a chromosomal integration sequence, 5' and 3' untranslated regions, or an intronic sequence, which are involved in transcriptional regulation. These cis-acting sequences typically interact with proteins or other biomolecules to carry out (turn on/off, regulate, modulate, etc.) gene transcription. Promoters are located 5' to the transcribed gene, and as used herein, include the sequence 5' from the translation start codon (i.e., including the 5' untranslated region of the mRNA, typically comprising 100-200 bp). Most often the core promoter sequences lie within 1-2 kb of the translation start site, more often within 1 kbp and often within 500 bp of the translation start site. By convention, the promoter sequence is usually provided as the sequence on the coding strand of the gene it controls. In the context of this application, a promoter is typically referred to by the name of the gene for which it naturally regulates expression. A promoter used in an expression construct of the invention is referred to by the name of the gene. Reference to a promoter by name includes a wildtype, native promoter as well as variants of the promoter that retain the ability to induce expression. Reference to a promoter by name is not restricted to a particular species, but also encompasses a promoter from a corresponding gene in other species.

The term "heterologous" as used herein refers to a material, or nucleotide or amino acid sequence, that is found in or is linked to another material, or nucleotide or amino acid sequence, wherein the materials, or nucleotide or amino acid sequences, are foreign to each other (i.e., not found or linked together in nature, such as within the same species of organism). A polynucleotide is "heterologous" to an organism or a second polynucleotide sequence if it originates from a foreign species, or, if from the same species, is modified from its original form. For example, when a polynucleotide encoding a polypeptide sequence is said to be operably linked to a heterologous promoter, it means that the polynucleotide coding sequence encoding the polypeptide is derived from one species whereas the promoter sequence is derived from another, different species; or, if both are derived from the same species, the coding sequence is not naturally associated with the promoter (e.g., is a genetically engineered coding sequence, e.g., from a different gene in the same species, or an allele from a different ecotype or variety).

The term "operably linked" refers to a functional relationship between two or more polynucleotide (e.g., DNA) segments. Typically, it refers to the functional relationship of a transcriptional regulatory sequence to a transcribed sequence. For example, a promoter or enhancer sequence is operably linked to a DNA or RNA sequence if it stimulates or modulates the transcription of the DNA or RNA sequence in an appropriate host cell or other expression system. Generally, promoter transcriptional regulatory sequences that are operably linked to a transcribed sequence are physically contiguous to the transcribed sequence, i.e., they are cis-acting. However, some transcriptional regulatory sequences, such as enhancers, need not be physically contiguous or located in close proximity to the coding sequences whose transcription they enhance.

The term "expression cassette" or "DNA construct" or "expression construct" refers to a nucleic acid construct that, when introduced into a host cell, results in transcription and/or translation of an RNA or polypeptide, respectively. Antisense or sense constructs that are not or cannot be translated are expressly included by this definition. In the case of both expression of transgenes and suppression of endogenous genes (e.g., by antisense, RNAi, or sense suppression) one of skill will recognize that the inserted polynucleotide sequence need not be identical, but may be only substantially identical to a sequence of the gene from which it was derived. As explained herein, these substantially identical variants are specifically covered by reference to a specific nucleic acid sequence. One example of an expression cassette is a polynucleotide construct that comprises a polynucleotide sequence encoding a protein operably linked to a heterologous promoter.

In some embodiments, the host organism is yeast. Yeast host cells suitable for practice of the methods of the invention include, but are not limited to, *Yarrowia, Candida, Bebaromyces, Saccharomyces, Schizosaccharomyces* and *Pichia*, including engineered strains provided by the invention. In one embodiment, *Saccharomyces cerevisae* is the host cell. In one embodiment, the yeast host cell is a species of *Candida*, including but not limited to *C. tropicalis, C. maltosa, C. apicola, C. paratropicalis, C. albicans, C. cloacae, C. guillermondii, C. intermedia, C. lipolytica, C. panapsilosis* and *C. zeylenoides*. In one embodiment, *Candida tropicalis* is the host cell.

In some embodiments the host is bacteria that is not an obligate aerobe. In some embodiments the host is bacteria that is a facultative anaerobe or an obligate anaerobe. Bacterial host cells suitable for practice of the methods of the invention include, but are not limited to, *Escherichia, Clostridium*, and *Bacillus*, including engineered strains provided by the invention. In one embodiment, the bacterial host cell is a species of *Bacillus*, including but not limited to *B. subtilis, B. brevis, B. megaterium, B. aminovorans*, and *B. fusiformis*. In one embodiment, *B. subtilis* is the host organism.

The amino acid sequence of a PhdB obtained from a sewage culture is:

```
                                            (SEQ ID NO: 1)
MSTQVSQHAPKAPEQMPRKIKLNFDPNGKMSDRFKKEKEKLFAAPARLDV

QKLQIETDVYSKWAASKSYSEIKAMIFDRLSREKKVWLDGNPICGHLTNF

IYGGYIQPWRDSYWIEDDKEFALQRGVHKTTEEERKIIQECGKFWIGQNM

QDRVRPIVKAKYGLDVQKLVDIGLGLNFDDDMGGMVVPCHRTVIERGLED

VLRQIACVKSKCKVYGVQAPDPTAGQVPNENTILTSVSPTSDYKKWHFLC

ACEVSIKALIHQAERYAALAREAAASEKDPCKKAEYEEMADRCSWVPAKP

ARTFKEALQAQWFITMGDWQNQCMTVHHAPMRFPQYVYANYKKDIEEGRI

TDEEAIEFLQFWFLKVNTQNFVMNPELAIWQQSRIAQQLTLGGLDPATGE

DGTCEVDYLILEAQRRAQCPEPLLSVMYHNKLSPKFLMECVKLIRTGIGQ

PSFHSQEVSMKRRLLHEEGPIEDIRDQAVAGCVQSIIGGKTDGTWEARFN

MTKMMEFFFSNGRDIKTGVAYGPAYGDPCECKTWEECYDRLYKYYEYWID

ICRDISTLEWNMERDHPTPLGSAVTYDCVERGMDMVDGGARYNWGDGVCL

AGSVDATNCLAAMKKLIFDDKSVSMEKMVAAITANFVGYEDVQNLCKKAP

KYGNDDPFADELGRRLMRDYAEIHNRKPDYMGRWTITPSAYSVTAHWAFG

KKTWATPDGRKAGECMTDATLSATPGTDVKGPTALIRSALKLIDPVVYGS

THFNVKFHPTALEGEAGAQKFLQLVKTYFDGGGYQIQFNCVTQETLRAAQ

KDPDSYRDLIVRVAGFSAYFITLCPEVQDEIVSRTCQTW
```

The amino acid sequence of a PhdB obtained from a lake sediment culture is:

```
                                            (SEQ ID NO: 2)
MSTQVTQKAPPAPEQMPRKIKLTFDPNGKMTDRFKKEKEKLFAAPARLDV

QKLQIETDVYSKWAASKSYNEIKAMIFDRLSREKKVWLDGNPICGHLTNF

VYGGYIQPWRDSYWIEDDKEFALQRGVHKTTAEEQKIIQECGKFWIGQNM

QDRVRPIVKAKYGLDVQKLVDIGLGLNFDDDMGGMVVPDHRMVIERGLED
```

```
                                           (SEQ ID NO: 2)
VLRQIADVKKRCKVYGVQAPDPTAGQVPTETTILTSVAPQPDYRKWHFLT

ACEISIKALIHQASRYAELAKEAAAKETDACKKAELEEMAERCSWVPAKP

ARTFKEAVQAQWFITMGDWQNQCMTVHHAPMRFPQYVYANYKKDIEEGRI

TDEEAIEFLCFWFLKVNTQNFVMNPELAIWQQSRIAQQLTIGGLDPATGE

DGTCEVDYLLLEAQRRAHCPEPQLAVMYHNKLSPKFLMACVTLIRTGLGQ

PSFHSQEVAMKRRLLHEEGPIEDIRDQAVAGCVQSIIGGKTDGTWEARFN

MCKMIEFFLSNGKDIKSGVSYGPAYGDPCECKTWDEFYDRLYKYYEYWID

ICRDISTLEWNMERDHPTPLGSAVTYDCVERGMDMTDGGARYNWGDGVCL

AGSVDVTNCLAAIKKLVYDDKSVSMDTMVKAIHADFVGYDEVRNLCMKAP

KYGNDDPAADELGRRLMRDYAEIHNRKPDYLGRWTITPSAYSVTAHWAFG

KKSWATPDGRKAGACMTDATLSANPGTDVKGPTALIRSALKLIDPVVYGS

THENVKFHPTALEGDAGAQKFLQLIKTYFDGGGYQIQFNCVTQETLRAAQ

KDPDSFRDLIVRVAGFSAYFITLCPEVQNEIVSRTSQQW
```

The amino acid sequence of a PhdA obtained from a sewage culture is:

```
                                           (SEQ ID NO: 3)
MGTNELTGMVFNIQGYSVQDGPGIRTTVFLKGCPLRCLWCSNPESQTTPK

DVLYIRAKCVKCHRCVNICKNGAISYNPDLEPEGYVTVNHEICATCKDHV

CVQGCYESAYEDVGTPMTVDQVMEILEADQPFFVQSGGGVTVSGGEPLLS

HEFLRELFKRCKQSYIHTAIETTGYAPWDNFKSVLEYTDLALFDVKHMDP

VIHKQLTGVSNELIHSNLEKVFAETKTQVVIRIPVIPGGNDTVENMQATA

KFMKKIGAREVDLMPYHRMGMGKYAGLGREYPMPPGVETPPAEKINELKA

VFESNGIVCHIGGNH
```

The amino acid sequence of a PhdA obtained from a lake sediment culture is:

```
                                           (SEQ ID NO: 4)
MGTSELTGTNELTGMVFNIQGYSIQDGPGIRTTIFLKGCPLRCLWCSNPE

SQTSPRDVLNIRAKCQKCHRCVDLCTNGAISYNPELEPEGYVTINHEICG

TCKDHLCVKGCFHNAYEDAGNPMTVSEVMEILEADQPFFVQSGGGVTVSG

GEPLVHHQFLRELFRRCKQSFIHTAIETTGYAPWDNFKSVLEYTDLALFD

VKHMDPIRHKELTGVSNELILKNLEKVFAETRTQVVVRIPVIPEGNDTVE

NMQATAQFMKKIGAREVDLMPYHRMGTGKYAGLGREYPLPMSLETPPVEK

IKELKGVFESNGIVCHIGGNH
```

The first polypeptide comprises an amino acid sequence that is at least 70%, 75%, 80%, 85%, 90%, 95% or 99% identical to the amino acid sequence of SEQ ID NO:1 or SEQ ID NO:2. The first polypeptide retains amino acids residues that are recognized as conserved for the enzyme. The first polypeptide may have non-conserved amino acid residues replaced or found to be of a different amino acid, or amino acid(s) inserted or deleted, but which does not affect or has insignificant effect on the enzymatic activity of the enzymatically active fragment. The first polypeptide may be found in nature or be an engineered mutant thereof. In some embodiments, the first polypeptide comprise a conserved glycyl radical motif comprising one or more of the following conserved amino acid sites/residues: R at position 812, V at position 813, G at position 815 (the position of the radical), F at position 816, L at position 823, Q at position 828, I at position 831, and/or R at position 834 of SEQ ID NO:1 or SEQ ID NO:2. In some embodiments, the first polypeptide comprises the following amino acid sequences: RVXGX$_{12}$QX$_5$R (SEQ ID NO:5), RVAGFX$_6$LX$_4$QX$_2$IX$_2$R (SEQ ID NO:6), or RVAGFSAYFITLCPEVQXEIVSR (SEQ ID NO:7). In some embodiments, the first polypeptide comprises a conserved C at position 482 (the location of the thiyl radical) of SEQ ID NO:1 or SEQ ID NO:2. In some embodiments, the first polypeptide comprises the following amino acid sequence: GCVXSG (SEQ ID NO:8) or GCVQQSIIGG (SEQ ID NO:9). A generalized glycyl radical motif is: RVxG[FWY]x$_{6-8}$[IL]x$_4$Qx$_2$[IV]x$_2$R, where the bold G is at position 815 of SEQ ID NO:1 or SEQ ID NO:2.

The second polypeptide comprises an amino acid sequence that is at least 70%, 75%, 80%, 85%, 90%, 95% or 99% identical to the amino acid sequence of SEQ ID NO:3 or SEQ ID NO:4. The second polypeptide retains amino acids residues that are recognized as conserved for the enzyme. The second polypeptide may have non-conserved amino acid residues replaced or found to be of a different amino acid, or amino acid(s) inserted or deleted, but which does not affect or has insignificant effect on the enzymatic activity of the enzymatically active fragment. The second polypeptide may be found in nature or be an engineered mutant thereof. In some embodiments, the second polypeptide comprise a conserved CxxxCxxC motif comprising one or more of the following conserved amino acid sites/residues: C at position 33, C at position 37, and/or C at position 40 of SEQ ID NO:3, or C at position 39, C at position 43, and/or C at position 46 of SEQ ID NO:4. In some embodiments, the first polypeptide comprises the following amino acid sequences: CXXXCXXC (SEQ ID NO:10), CXXXCXXCXN (SEQ ID NO:11), CPLRCLWC (SEQ ID NO:12), GXRX$_3$FX$_2$GCX$_3$CX$_2$CXN (SEQ ID NO:13), or FLKGCPLRCLWCSNPE (SEQ ID NO:14).

One can modify the expression of a gene encoding any of the enzymes taught herein by a variety of methods in accordance with the methods of the invention. Those skilled in the art would recognize that increasing gene copy number, ribosome binding site strength, promoter strength, and various transcriptional regulators can be employed to alter an enzyme expression level. The present invention provides a method of producing a substituted or unsubstituted toluene or 2-methyl-1H-indole in a genetically modified host cell that is modified by the increased expression of one or more genes taught herein.

The present invention also provides methods and genetically modified host cells that have been engineered to be capable of secreting or excreting the substituted or unsubstituted toluene or 2-methyl-1H-indole into the media. In some embodiments, genetically modified host cells and methods are provided to make the substituted or unsubstituted toluene or 2-methyl-1H-indole that are secreted or excreted into the media or fermentation broth. In particular embodiments, these genetically modified host cells are further modified by expression of one or more genes encoding proteins involved in the export of substituted or unsubstituted toluene or 2-methyl-1H-indole such that the product is moved from the interior of the cell to the exterior.

Once in the media or fermentation broth, the substituted or unsubstituted toluene or 2-methyl-1H-indole can be separated, isolated, and/or purified in accordance with the invention. In some embodiments, the genetically modified host cells is modified to secrete the substituted or unsubstituted toluene or 2-methyl-1H-indole, and subsequently purified from the broth. In some embodiments, an ion exchange is employed for further purification of the substituted or unsubstituted toluene or 2-methyl-1H-indole.

In other embodiments, the host cells are not modified to secrete the product into the growth medium and the product accumulates in the host cell. In these embodiments, the substituted or unsubstituted toluene or 2-methyl-1H-indole is separated from the host cell in accordance with the invention by centrifugation or settling of the cell material, cell lysis, and subsequent purification of the substituted or unsubstituted toluene or 2-methyl-1H-indole.

REFERENCES CITED

1 Galperin, M. Y. & Koonin, E. V. From complete genome sequence to 'complete' understanding? *Trends Biotechnol.* 28, 398-406, doi:10.1016/j.tibtech.2010.05.006 (2010).
2 Gerlt, J. A. et al. The Enzyme Function Initiative. *Biochemistry* 50, 9950-9962, doi:10.1021/bi201312u (2011).
3 Anton, B. P. et al. The COMBREX project: design, methodology, and initial results. *PLoS Biol.* 11, e1001638, doi:10.1371/journal.pbio.1001638 (2013).
4 Lespinet, O. & Labedan, B. Orphan enzymes? *Science* 307, 42, doi:10.1126/science.307.5706.42a (2005).
5 Sorokina, M., Stam, M., Medigue, C., Lespinet, O. & Vallenet, D. Profiling the orphan enzymes. *Biol. Direct* 9, 10, doi:10.1186/1745-6150-9-10 (2014).
6 McKenna, R. & Nielsen, D. R. Styrene biosynthesis from glucose by engineered *E. coli. Metab. Eng.* 13, 544-554, doi:10.1016/j.ymben.2011.06.005 (2011).
7 Jüttner, F. & Henatsch, J. J. Anoxic hypolimnion is a significant source of biogenic toluene. *Nature* 323, 797-798 (1986).
8 Zargar, K. et al. In vitro characterization of phenylacetate decarboxylase, a novel enzyme catalyzing toluene biosynthesis in an anaerobic microbial community. *Scientific Reports* 6, 31362, doi:10.1038/srep31362 (2016).
9 Fischer-Romero, C., Tindall, B. J. & Juttner, F. *Tolumonas auensis* gen. nov., sp. nov., a toluene-producing bacterium from anoxic sediments of a freshwater lake. *Int. J. Syst. Bacteriol.* 46, 183-188, doi:10.1099/00207713-46-1-183 (1996).
10 Pons, J. L., Rimbault, A., Darbord, J. C. & Leluan, G. [Biosynthesis of toluene in *Clostridium aerofoetidum* strain WS]. *Ann. Microbiol. (Paris)* 135B, 219-222 (1984).
11 Akhtar, M. K., Turner, N. J. & Jones, P. R. Carboxylic acid reductase is a versatile enzyme for the conversion of fatty acids into fuels and chemical commodities. *Proc. Natl. Acad. Sci. USA* 110, 87-92, doi:10.1073/pnas.1216516110 (2013).
12 Schirmer, A., Rude, M. A., Li, X., Popova, E. & del Cardayre, S. B. Microbial biosynthesis of alkanes. *Science* 329, 559-562, doi:10.1126/science.1187936 (2010).
13 Selmer, T. & Andrei, P. I. p-Hydroxyphenylacetate decarboxylase from *Clostridium difficile*. A novel glycyl radical enzyme catalysing the formation of p-cresol. *Eur. J. Biochem.* 268, 1363-1372 (2001).
14 Yu, L., Blaser, M., Andrei, P. I., Pierik, A. J. & Selmer, T. 4-Hydroxyphenylacetate decarboxylases: properties of a novel subclass of glycyl radical enzyme systems. *Biochemistry* 45, 9584-9592, doi:10.1021/bi060840b (2006).
15 Selmer, T., Pierik, A. J. & Heider, J. New glycyl radical enzymes catalysing key metabolic steps in anaerobic bacteria. *Biol. Chem.* 386, 981-988, doi:10.1515/BC.2005.114 (2005).
16 Shisler, K. A. & Broderick, J. B. Glycyl radical activating enzymes: structure, mechanism, and substrate interactions. *Arch. Biochem. Biophys.* 546, 64-71, doi:10.1016/j.abb.2014.01.020 (2014).
17 Leuthner, B. et al. Biochemical and genetic characterization of benzylsuccinate synthase from *Thauera aromatica*: a new glycyl radical enzyme catalysing the first step in anaerobic toluene metabolism. *Mol. Microbiol.* 28, 615-628 (1998).
18 O'Brien, J. R. et al. Insight into the mechanism of the B12-independent glycerol dehydratase from *Clostridium butyricum*: preliminary biochemical and structural characterization. *Biochemistry* 43, 4635-4645, doi:10.1021/bi035930k (2004).
19 Beller, H. R. & Spormann, A. M. Substrate range of benzylsuccinate synthase from *Azoarcus* sp. strain T. *FEMS Microbiol. Lett.* 178, 147-153 (1999).
20 Becker, A. et al. Structure and mechanism of the glycyl radical enzyme pyruvate formate-lyase. *Nat. Struct. Biol.* 6, 969-975, doi:10.1038/13341 (1999).
21 Larsson, K. M., Andersson, J., Sjoberg, B. M., Nordlund, P. & Logan, D. T. Structural basis for allosteric substrate specificity regulation in anaerobic ribonucleotide reductases. *Structure* 9, 739-750 (2001).
22 Heider, J., Spormann, A. M., Beller, H. R. & Widdel, F. Anaerobic bacterial metabolism of hydrocarbons. *FEMS Microbiology Reviews* 22, 459-473 (1998).
23 Feliks, M., Martins, B. M. & Ullmann, G. M. Catalytic mechanism of the glycyl radical enzyme 4-hydroxyphenylacetate decarboxylase from continuum electrostatic and QC/MM calculations. *J. Am. Chem. Soc.* 135, 14574-14585, doi:10.1021/ja402379q (2013).
24 Kalnins, G. et al. Structure and function of CutC choline lyase from human microbiota bacterium *Klebsiella pneumoniae*. *J Biol Chem* 290, 21732-21740, doi:10.1074/jbc.M115.670471 (2015).
25 Craciun, S. & Balskus, E. P. Microbial conversion of choline to trimethylamine requires a glycyl radical enzyme. *Proc. Natl. Acad. Sci. USA* 109, 21307-21312, doi:10.1073/pnas.1215689109 (2012).
26 Levin, B. J. et al. A prominent glycyl radical enzyme in human gut microbiomes metabolizes trans-4-hydroxy-1-proline. *Science* 355, doi:10.1126/science.aai8386 (2017).
27 Funk, M. A., Marsh, E. N. & Drennan, C. L. Substrate-bound structures of benzylsuccinate synthase reveal how toluene is activated in anaerobic hydrocarbon degradation. *J. Biol. Chem.* 290, 22398-22408, doi:10.1074/jbc.M115.670737 (2015).
28 Martins, B. M. et al. Structural basis for a Kolbe-type decarboxylation catalyzed by a glycyl radical enzyme. *J. Am. Chem. Soc.* 133, 14666-14674, doi:10.1021/ja203344x (2011).
29 Kielak, A. M., Barreto, C. C., Kowalchuk, G. A., van Veen, J. A. & Kuramae, E. E. The Ecology of Acidobacteria: Moving beyond Genes and Genomes. *Front. Microbiol.* 7, 744, doi:10.3389/fmicb.2016.00744 (2016).
30 Ward, N. L. et al. Three genomes from the phylum Acidobacteria provide insight into the lifestyles of these microorganisms in soils. *Appl. Environ. Microbiol.* 75, 2046-2056, doi:10.1128/AEM.02294-08 (2009).

31 Altschul, S. F., Gish, W., Miller, W., Myers, E. W. & Lipman, D. J. Basic local alignment search tool. *J. Mol. Biol.* 215, 403-410, doi:10.1016/S0022-2836(05)80360-2 (1990).

32 Dawson, L. F., Stabler, R. A. & Wren, B. W. Assessing the role of p-cresol tolerance in *Clostridium difficile*. *J. Med. Microbiol.* 57, 745-749, doi:10.1099/jmm.0.47744-0 (2008).

33 Schneider, S., Mohamed, M. E. S. & Fuchs, G. Anaerobic metabolism of L-phenylalanine via benzoyl-CoA in the denitrifying bacterium *Thauera aromatica*. *Arch. Microbiol.* 168, 310-320 (1997).

34 Carmona, M. et al. Anaerobic catabolism of aromatic compounds: a genetic and genomic view. *Microbiol. Mol. Biol. Rev.* 73, 71-133, doi:10.1128/MMBR.00021-08 (2009).

35 Molenaar, D., Bosscher, J. S., ten Brink, B., Driessen, A. J. & Konings, W. N. Generation of a proton motive force by histidine decarboxylation and electrogenic histidine/histamine antiport in *Lactobacillus buchneri*. *J Bacteriol* 175, 2864-2870 (1993).

36 Pereira, C. I., Matos, D., San Romao, M. V. & Crespo, M. T. Dual role for the tyrosine decarboxylation pathway in *Enterococcus faecium* E17: response to an acid challenge and generation of a proton motive force. *Appl Environ Microbiol* 75, 345-352, doi:10.1128/AEM.01958-08 (2009).

37 Beller, H. R., Legler, T. C. & Kane, S. R. Genetic manipulation of the obligate chemolithoautotrophic bacterium *Thiobacillus denitrificans*. *Methods Mol. Biol.* 881, 99-136, doi:10.1007/978-1-61779-827-6_5 (2012).

38 Huntemann, M. et al. The standard operating procedure of the DOE-JGI Microbial Genome Annotation Pipeline (MGAP v.4). *Stand. Genomic Sci.* 10, 86, doi:10.1186/s40793-015-0077-y (2015).

39 Edgar, R. C. UPARSE: highly accurate OTU sequences from microbial amplicon reads. *Nat. Methods* 10, 996-998, doi:10.1038/nmeth.2604 (2013).

40 Quast, C. et al. The SILVA ribosomal RNA gene database project: improved data processing and web-based tools. *Nucleic Acids Res.* 41, D590-596, doi:10.1093/nar/gks1219 (2013).

41 Studier, F. W. Protein production by auto-induction in high density shaking cultures. *Protein Expr. Purif.* 41, 207-234 (2005).

42 Gao, H. et al. *Arabidopsis thaliana* Nfu2 accommodates [2Fe-2S] or [4Fe-4S] clusters and is competent for in vitro maturation of chloroplast [2Fe-2S] and [4Fe-4S] cluster-containing proteins. *Biochemistry* 52, 6633-6645, doi:10.1021/bi4007622 (2013).

43 Mackay, D. & Shiu, W. Y. A critical review of Henry's Law constants for chemicals of environmental interest. *Journal of Physical and Chemical Reference Data* 10, 1175-1199 (1981).

44 Grant, C. E., Bailey, T. L. & Noble, W. S. FIMO: scanning for occurrences of a given motif. *Bioinformatics* 27, 1017-1018, doi:10.1093/bioinformatics/btr064 (2011).

45 Edgar, R. C. MUSCLE: multiple sequence alignment with high accuracy and high throughput. *Nucleic Acids Res.* 32, 1792-1797, doi:10.1093/nar/gkh340 (2004).

46 Stamatakis, A. RAxML version 8: a tool for phylogenetic analysis and post-analysis of large phylogenies. *Bioinformatics* 30, 1312-1313, doi:10.1093/bioinformatics/btu033 (2014).

47 Letunic, I. & Bork, P. Interactive tree of life (iTOL) v3: an online tool for the display and annotation of phylogenetic and other trees. *Nucleic Acids Res.* 44, W242-245, doi:10.1093/nar/gkw290 (2016).

48 Bankevich, A. et al. SPAdes: a new genome assembly algorithm and its applications to single-cell sequencing. *J. Comput. Biol.* 19, 455-477, doi:10.1089/cmb.2012.0021 (2012).

49 Wu, Y. W., Simmons, B. A. & Singer, S. W. MaxBin 2.0: an automated binning algorithm to recover genomes from multiple metagenomic datasets. *Bioinformatics* 32, 605-607, doi:10.1093/bioinformatics/btv638 (2016).

50 Hyatt, D. et al. Prodigal: prokaryotic gene recognition and translation initiation site identification. *BMC bioinformatics* 11, 119, doi:10.1186/1471-2105-11-119 (2010).

51 Parks, D. H., Imelfort, M., Skennerton, C. T., Hugenholtz, P. & Tyson, G. W. CheckM: assessing the quality of microbial genomes recovered from isolates, single cells, and metagenomes. *Genome Res.* 25, 1043-1055, doi:10.1101/gr.186072.114 (2015).

52 Krzywinski, M. et al. Circos: an information aesthetic for comparative genomics. *Genome Res.* 19, 1639-1645, doi:10.1101/gr.092759.109 (2009).

53 Price, M. N., Dehal, P. S. & Arkin, A. P. FastTree: computing large minimum evolution trees with profiles instead of a distance matrix. *Mol. Biol. Evol.* 26, 1641-1650, doi:10.1093/molbev/msp077 (2009).

54 Biasini, M. et al. SWISS-MODEL: modelling protein tertiary and quaternary structure using evolutionary information. *Nucleic Acids Research* 42, W252-258, doi:10.1093/nar/gku340 (2014).

55 Emsley, P. & Cowtan, K. Coot: model-building tools for molecular graphics. *Acta Crystallogr. D Biol. Crystallogr.* 60, 2126-2132, doi:10.1107/S0907444904019158 (2004).

56 Vagin, A. A. et al. REFMAC5 dictionary: organization of prior chemical knowledge and guidelines for its use. *Acta Crystallogr. D Biol. Crystallogr.* 60, 2184-2195, doi:10.1107/S0907444904023510 (2004).

57 Davis, I. W. et al. MolProbity: all-atom contacts and structure validation for proteins and nucleic acids. *Nucleic Acids Research* 35, W375-383, doi:10.1093/nar/gkm216 (2007).

58 Sievers, F. et al. Fast, scalable generation of high-quality protein multiple sequence alignments using Clustal Omega. *Mol. Syst. Biol.* 7, 539, doi:10.1038/msb.2011.75 (2011).

It is to be understood that, while the invention has been described in conjunction with the preferred specific embodiments thereof, the foregoing description is intended to illustrate and not limit the scope of the invention. Other aspects, advantages, and modifications within the scope of the invention will be apparent to those skilled in the art to which the invention pertains.

All patents, patent applications, and publications mentioned herein are hereby incorporated by reference in their entireties.

The invention having been described, the following examples are offered to illustrate the subject invention by way of illustration, not by way of limitation.

Example 1

Enzyme Discovery for Toluene Synthesis in Anoxic Microbial Communities

Microbial toluene biosynthesis was reported in anoxic lake sediments more than three decades ago, however the enzyme(s) catalyzing this biochemically challenging reaction have never been elucidated. Herein is reported the first toluene synthase, a glycyl radical enzyme of bacterial origin that catalyzes phenylacetic acid decarboxylation (PhdB), and its cognate activating enzyme (PhdA, a radical S-adenosylmethionine enzyme), discovered in two distinct anoxic microbial communities that produced toluene. The unconventional process of enzyme discovery from a complex microbial community (>300,000 genes) rather than from a microbial isolate, involved metagenomics- and metaproteomics-enabled biochemistry, as well as in-vitro confirmation of activity with recombinant enzymes. This example expands the known catalytic range of glycyl radical enzymes (only seven reaction types had been characterized previously) and aromatic hydrocarbon-producing enzymes (only one reaction type characterized previously), and will enable first-time biochemical synthesis of an aromatic fuel hydrocarbon from renewable resources, such as lignocellulosic biomass, rather than petroleum.

The aromatic hydrocarbon toluene is targeted for enzyme discovery, as it is an important petrochemical with a global market of 29 million tons per year whose uses include synthesis of other aromatic feedstocks and serving as an effective octane booster in gasoline (octane number, 114). Microbial sources of biogenic toluene were reported more than three decades ago, however, the underlying biochemistry and specific enzymes catalyzing toluene biosynthesis have never been elucidated. Biogenic toluene was observed in anoxic lake sediments/hypolimnion[7], in anoxic enrichment cultures derived from municipal sewage sludge[8], and in two bacterial isolates, *Tolumonas auensis*[9] and *Clostridium aerofoetidum*[10], which were reported to synthesize toluene from phenylacetate and L-phenylalanine (however, recent attempts to reproduce toluene biosynthesis by these two isolates were unsuccessful[8]). Although a toluene synthase has not been specifically identified, in vitro studies with cell-free extracts from a toluene-producing culture suggest catalysis by a glycyl radical enzyme (GRE)[8]. Evidence supporting the hypothesized role of a GRE in toluene biosynthesis included (a) irreversible inactivation by $O_2$ (a characteristic of GREs), (b) the ruling out of a mechanism involving successive reduction (phenylacetate to phenylacetaldehyde) and decarbonylation/deformylation (phenylacetaldehyde to toluene), which would not be expected to be catalyzed by GREs[11,12], and (c) the observation that the known enzyme with the greatest functional similarity to phenylacetate decarboxylase, namely p-hydroxyphenylacetate decarboxylase (HpdBC or CsdBC), is a GRE[13,14]. Although a GRE has been implicated in toluene biosynthesis, even the most detailed in vitro studies conducted to date have not identified any specific gene candidates[8].

Identification of Toluene Synthase Candidates

Figure 8:
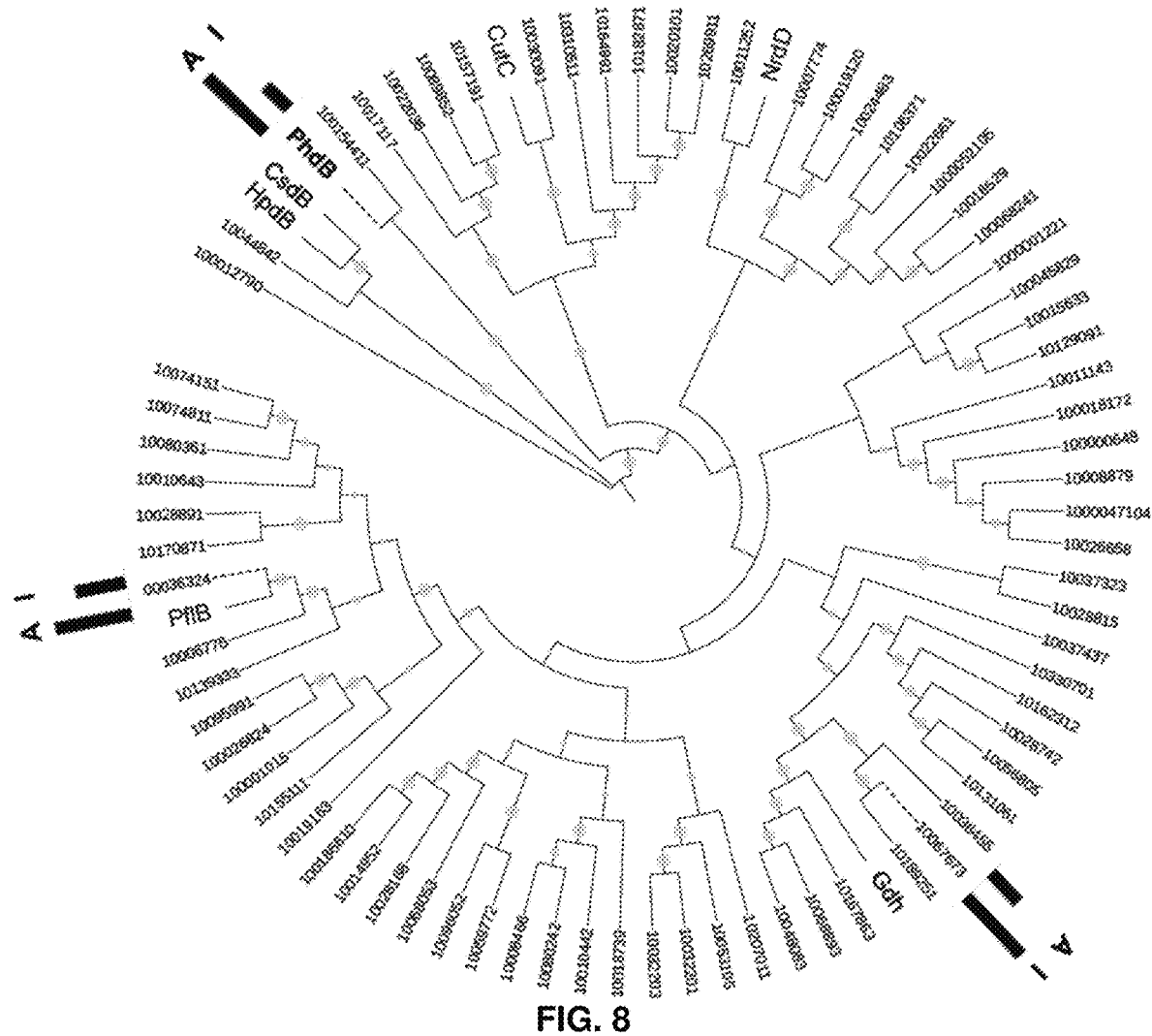
FIG. 8. Glycyl radical enzymes encoded in a toluene-producing sewage culture metagenome and their association with in vitro toluene synthase activity. This maximum-likelihood tree is based on protein sequences of putative glycyl radical enzymes (GREs) detected in the sewage-derived metagenome [IMG Taxon ID 3300001865 on JGI's IMG-M site (webpage for: img.jgi.doe.gov/cgi-bin/mer/main.cgi)]. Numerical values on the leaves represent locus tags in the metagenome from which the prefix "JGI2065J20421_" has been truncated for brevity. Leaves with protein names rather than locus tags are known GREs provided for context. The leaf marked PhdB represents the GRE characterized in this study. Leaves with dashed lines represent proteins detected by LC/MS/MS in active FPLC fractions, and the histograms on these leaves represent the maximum abundance of this protein in (A) the two most active fractions and (I) the two flanking inactive or less active fractions; histograms are normalized to the greatest of the A and I values. Purple circles on leaves represent bootstrap support values for each node (largest symbols are 100).

Studies to identify a toluene synthase (phenylacetate decarboxylase) are conducted with anaerobic, toluene-producing microbial cultures that derived from two different inocula: municipal sewage sludge[8] and lake sediments from Berkeley, Calif. The sewage culture, which was more amenable to cultivation and in vitro studies, served as the basis for most of the experimental discovery studies, whereas the lake sediment culture was used primarily for metagenome sequencing. A metagenomics- and metaproteomics-enabled protein purification approach is employed for enzyme discovery from these microbial communities. Toluene synthase activity is monitored in chromatographically separated fractions of cell-free extracts from the sewage culture using in vitro assays that measured phenylacetic acid-2-$^{13}$C conversion to [methyl-$^{13}$C]toluene. All experimental procedures, including cultivation, cell lysis, protein purification by FPLC (fast protein liquid chromatography), and in vitro assays, are performed under strictly anaerobic conditions to protect the organisms and enzymes from molecular oxygen. Proteomic profiles of active FPLC fractions are compared to those of adjacent inactive (or much less active) fractions to identify toluene synthase candidates (i.e., those proteins enriched in, and ideally unique to, active fractions). An unknown GRE (hereafter referred to as PhdB) co-eluted with the maximal toluene synthase activity. Although more than 650 proteins co-eluted with PhdB in these fractions, this protein is initially of interest because the toluene synthase in this sewage-derived culture had been postulated to be a GRE based upon in vitro studies with cell-free extracts[8]. Notably, PhdB was one of the few glycyl radical enzymes detected in active fractions among the many glycyl radical enzymes encoded in the sewage community metagenome (FIG. 8). As shown in FIG. 8, only three glycyl radical enzymes are detected in the active FPLC fractions: (1) PhdB, (2) pyruvate formate-lyase (PflB; JGI2065J20421_100036324; IMG Taxon ID 3300001865), which had 99% sequence identity to known *Enterobacter* PflB copies], and (3) an unknown glycyl radical enzyme (JGI2065J20421_10067673; IMG Taxon ID 3300001865)—this protein shares ca. 47% sequence identity and key conserved residues with a known glycerol dehydratase (PDB 1R8W). Of these three proteins, only PhdB and the PflB had greater abundance in active than in flanking inactive fractions (FIG. 8), and PflB is among the most abundant proteins in both active and inactive fractions, which, along with its well-characterized function, reduced its plausibility as a toluene synthase candidate.

Figure 9:
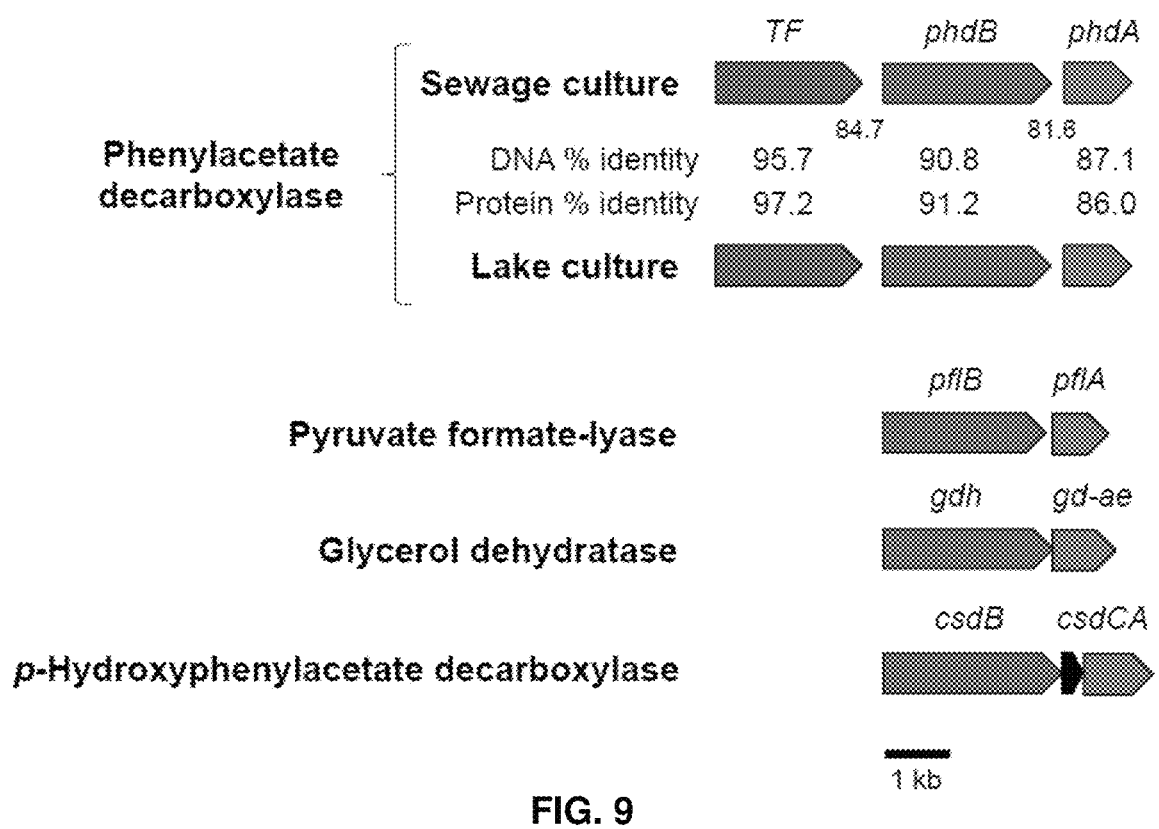
FIG. 9. Homologous phenylacetate decarboxylase gene clusters from sewage and lake sediment cultures. phdB, phenylacetate decarboxylase (a glycyl radical enzyme); phdA, a cognate activating enzyme for phdB; TF, putative transcription factor. Sequence identity is shown for the coding sequences as well as the two intergenic regions. Gene clusters for selected GREs (in red) and their cognate activating enzymes (in blue) are shown for comparison, including pyruvate formate-lyase (pflB, pflA; JGI IMG accession no.: b0903-2; *E. coli* MG1655), glycerol dehydratase (gdh, gd-ae; JGI IMG: Ga0175177_11489-8; *Clostridium butyricum*), and p-hydroxyphenylacetate decarboxylase (csdB, csdC, csdA; JGI IMG: Ga0077986_114454-2; *Clostridium scatologenes*). A 1-kb scale bar is included.

The strength of phdB as a candidate toluene synthase gene is enhanced by its identification in metagenomes of both the anoxic, toluene-producing sewage and lake sediment cultures, despite the fact that these cultures have disparate inocula and phylogenetic compositions. In sewage culture metagenomes, phdB occurred in a three-gene cluster consisting of a putative transcription factor, phdB, and a glycyl radical activating enzyme (hereafter referred to as phdA) (FIG. 9). Such adjacent positioning in genomes of genes encoding glycyl radical enzymes and their cognate activating enzymes is very common[15], as indicated in FIG. 9. Although assembled contigs from the lake sediment metagenomes (e.g., IMG Taxon ID 2100351000) are not observed to harbor the complete three-gene cluster detected in the sewage metagenome, the quality of these assemblies is suboptimal as a result of older sequencing methods used. Indeed, PCR amplification and Sanger sequencing of this cluster from genomic DNA of the lake culture revealed an intact three-gene cluster with identical length (6065 bp) and strikingly similar coding and intergenic sequences compared to the sewage culture (FIG. 9). As shown in FIG. 9, the three genes share from ca. 87 to 96% sequence identity (and 86 to 97% translated sequence identity) in the sewage and lake cultures and the intergenic regions are ca. 82-85% identical.

In Vitro Confirmation of PhdB and PhdA Activity

Figure 5:
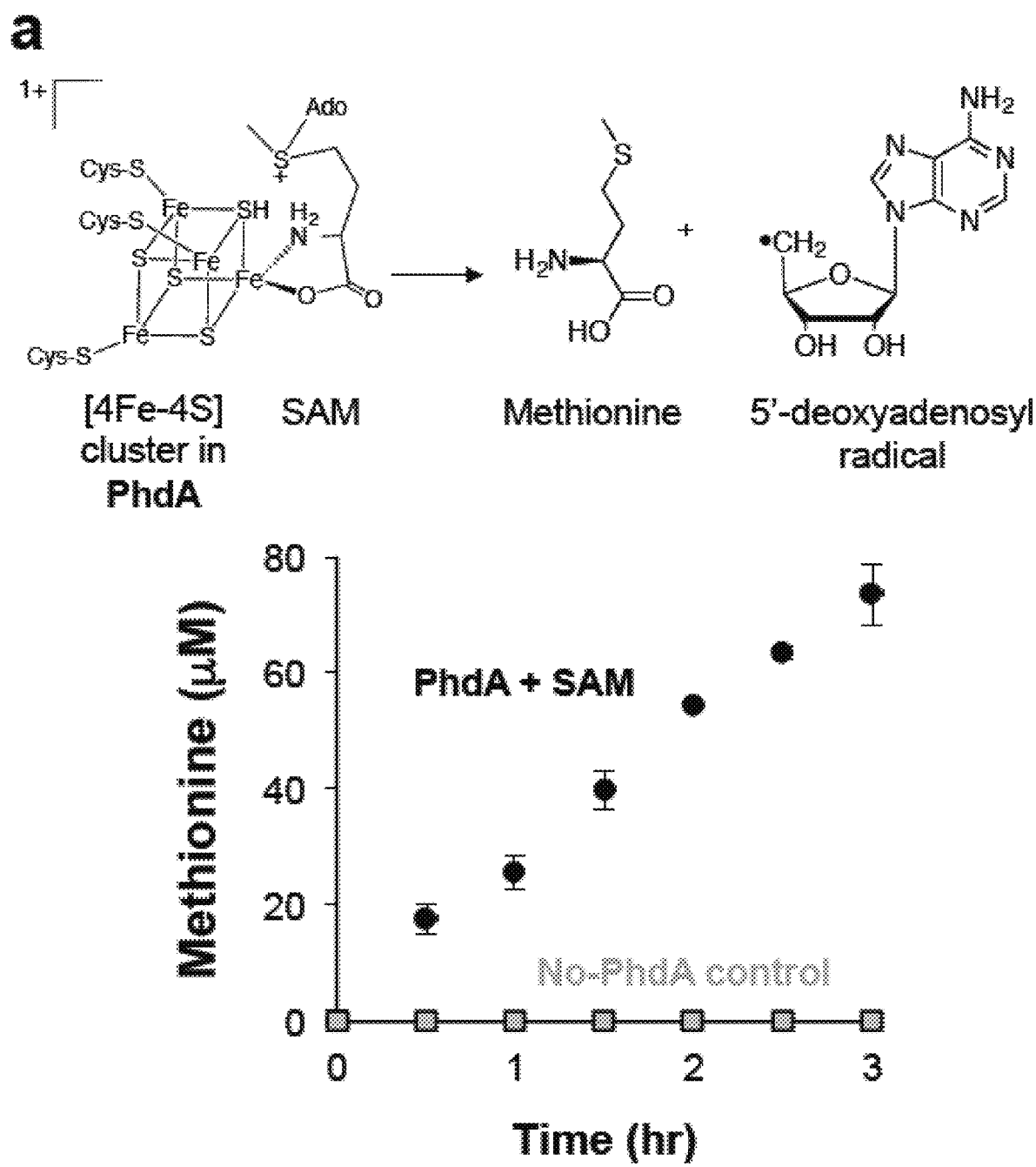
FIG. 5. Reactions catalyzed by PhdA. Proposed reaction of PhdA with SAM, as supported in vitro by methionine production by re-constituted and purified recombinant PhdA (black circles). Controls without PhdA are also shown (gray squares). Experiments demonstrating PhdA-catalyzed production of methionine from SAM were replicated three times and experiments demonstrating labeled toluene production from labeled phenylacetate in the presence of PhdA were performed 6 times (four times with no-SAM negative controls).
Figure 7:
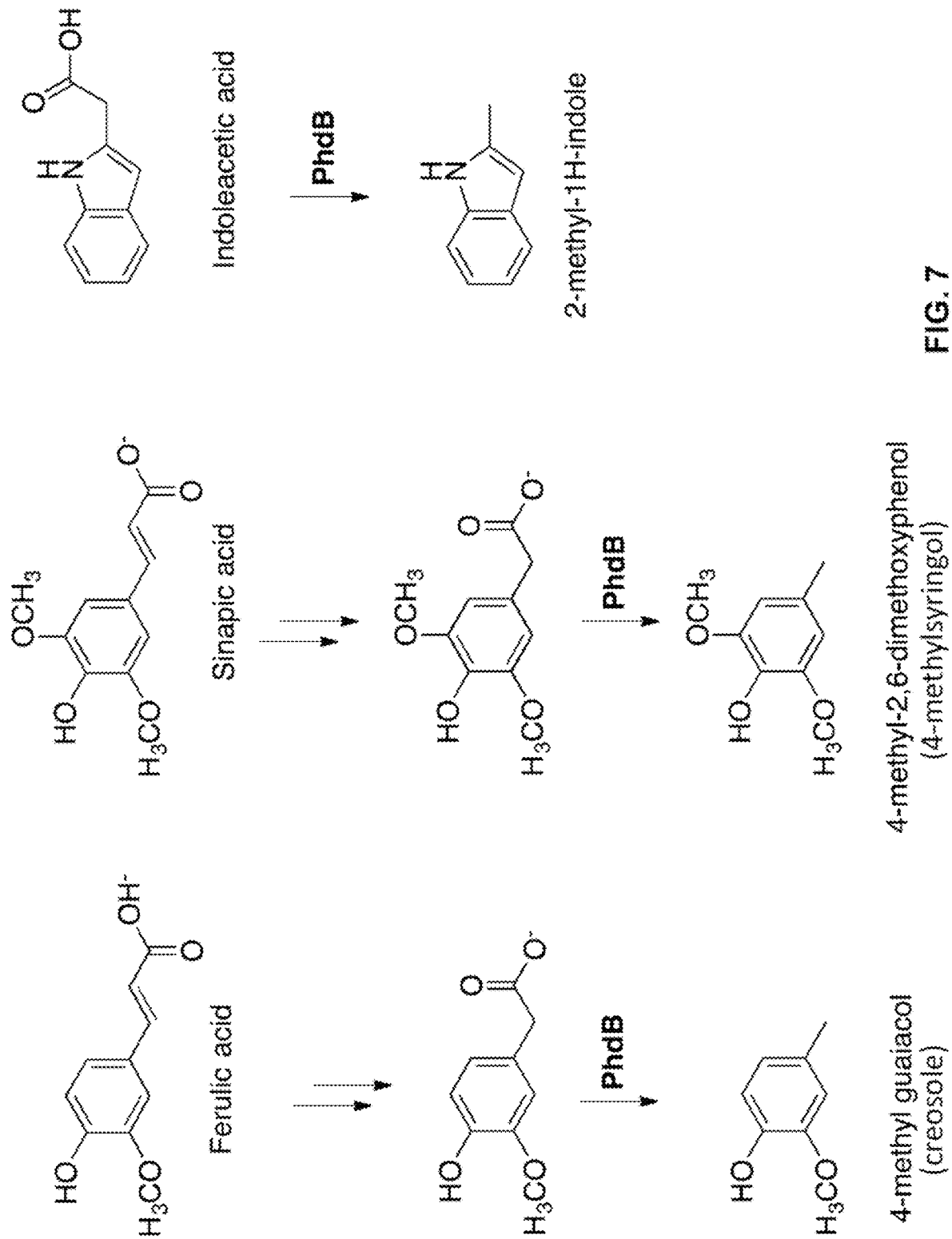
FIG. 7. Other reactions that can be catalyzed by PhdB. The question marks indicate the indicated reaction has not yet been tested.

Recombinant versions of PhdA and PhdB are assayed for in vitro activity to confirm their role in catalyzing toluene biosynthesis from phenylacetate. The expected activity for PhdA is based on characterization of other glycyl radical activating enzymes[16]. In glycyl radical systems, the reduced $[4Fe-4S]^{+1}$ cluster of the activase, a radical S-adenosylmethionine (SAM) enzyme, transfers an electron to SAM, resulting in homolytic cleavage of SAM to form methionine and a 5'-deoxyadenosyl radical (FIG. 5). The 5'-deoxyadenosyl radical activates the GRE by stereospecific abstraction of a C-2 pro-S H atom from a highly conserved glycine residue, which in turn abstracts an H atom from a conserved cysteine residue in the GRE to form a thiyl radical. A substrate radical is formed when the thiyl radical abstracts an H atom from the substrate (phenylacetic acid, in the case of PhdB; FIG. 6).

In vitro reconstitution of the [4Fe-4S] cluster of PhdA is performed before final purification (all under strictly anaerobic conditions), and the [4Fe-4S] cluster is reduced with dithionite in an anoxic assay measuring methionine production from SAM using liquid chromatography-mass spectrometry (LC/MS). Observed methionine production in the presence of PhdA, but not in its absence (FIG. 5), demonstrated the expected activity of a glycyl radical activating enzyme.

The ability of activated (enzyme-radical) PhdB to catalyze decarboxylation of phenylacetic acid-2-$^{13}$C to [methyl-$^{13}$C]toluene is tested in anoxic, in vitro assays in the presence of dithionite-reduced PhdA and SAM (FIG. 6). Labeled toluene is detected by gas chromatography-mass spectrometry (GC/MS) in the presence of SAM but not in its absence, confirming the role of PhdB in catalyzing toluene biosynthesis via a radical mechanism. A series of other negative control assays also displayed negligible activity, including the following: (1) assays lacking PhdB but containing dithionite-reduced PhdA and SAM, (2) assays conducted with a mutant version of PhdB (G815A) in which the putative site of the glycyl radical is modified to alanine, and (3) assays in which the assay mixture is briefly exposed to air before the substrate was added, demonstrating O$_2$ sensitivity that is characteristic of GREs. Specific activities observed in SAM-containing assays represented in FIG. 6 are relatively low (in the pmol·min$^{-1}$·mg protein$^{-1}$ range) compared to reported values for most other GREs, which range broadly from pmol·min$^{-1}$·mg protein$^{-1}$ (benzylsuccinate synthase[17]) to mmol·min$^{-1}$·mg protein$^{-1}$ (glycerol dehydratase[18]). In part, low PhdB activity may reflect the generally sensitive nature of GREs when purified and manipulated in vitro. For example, even for a given enzyme, reported specific activities have differed by orders of magnitude in various studies [e.g., for benzylsuccinate synthase, from 0.02[17] to 72 nmol·min$^{-1}$·mg protein$^{-1}$ [19]; for p-hydroxyphenylacetate decarboxylase, from 0.034[13] to 18.45 μmol·min$^{-1}$·mg protein$^{-1}$ [14]]. In the present example, a likely factor affecting PhdB activity is the poor solubility of the recombinant protein when expressed in E. coli; a maltose-binding protein (MBP) tag is used to enhance solubility but may not have fully ameliorated suboptimal folding. For biotechnological application of PhdB, enhanced solubility (e.g., through protein engineering) is required.

While PhdB displays phenylacetate decarboxylase activity, it does not display comparable p-hydroxyphenylacetate decarboxylase activity (characteristic of the GRE HpdBC/CsdBC). During assays in which equimolar amounts of phenylacetate and p-hydroxyphenylacetate are amended to a mixture containing PhdA, PhdB, and SAM, labeled toluene production is readily observed, however, p-cresol (the product of p-hydroxyphenylacetate decarboxylation) is detected at levels approximately 100-fold lower than those expected if PhdB activity are comparable for phenylacetate and p-hydroxyphenylacetate. Analogous assays with o- and m-hydroxyphenylacetate similarly indicated very low (in this case, undetectable) PhdB activity for these hydroxyphenylacetate isomers, whereas labeled toluene is easily detected.

Comparison of PhdB-PhdA to Other Glycyl Radical Systems

The demonstration of PhdB as a phenylacetate decarboxylase adds it to the group of seven characterized GREs (FIG. 10), which includes pyruvate formate-lyase (EC 2.3.1.54[20]), anaerobic ribonucleotide reductase (EC 1.17.4.1[21]), benzylsuccinate synthase (EC 4.1.99.11[17,19,22]) p-hydroxyphenylacetate decarboxylase (EC 4.1.1.82[13,14,23]), B$_{12}$-independent glycerol (and 1,2-propanediol) dehydratase (EC 4.2.1.30[18]), choline trimethylamine-lyase (EC 4.3.99.4[24,25]), and the very recently discovered trans-4-hydroxy-L-proline dehydratase[26]. Note that benzylsuccinate synthase, which catalyzes the first step of anaerobic toluene degradation, is the best characterized representative of a larger group of aromatic- and alkylsuccinate synthase enzymes that activate substrates including 2-methylnaphthalene, p-cresol, and n-hexane by fumarate addition and have been collectively termed "X-succinate synthases"[27].

PhdB shares important features characteristic of all known GREs, including the following: (1) a conserved glycyl radical motif (RVxG[FWY]x$_{6-8}$[/L]x$_4$Qx$_2$[IV]x$_2$R modification from Selmer et al.[15] indicated in italics) near the C-terminus of the protein (FIG. 11, Panel a), (2) a conserved cysteine residue near the middle of the protein sequence (the site of the thiyl radical in the active site that initiates H atom abstraction from the substrate) (FIG. 11, Panel b), and (3) a cognate activating enzyme that belongs to the radical SAM superfamily1[15]. However, PhdB is clearly distinct from the other known glycyl radical enzymes in a number of ways. For example, the sequence identity of PhdB (from the sewage and lake cultures) to other GREs is relatively low, ranging from ca. 14 to 31%. Further, PhdB does not share all of the conserved residues that have been assigned for other GREs. To illustrate, in the region near the conserved active-site C residue (FIG. 11, Panel b), some conserved residues not shared by PhdB include an additional C adjacent to the strictly conserved active-site C (PflB[20]), an E located two residues downstream of the active-site C (CsdB[23], Gdh[18], CutC[24], HypD[26]), and M-S-P residues immediately downstream of the active-site C (BssA[27]).

Figure 10:
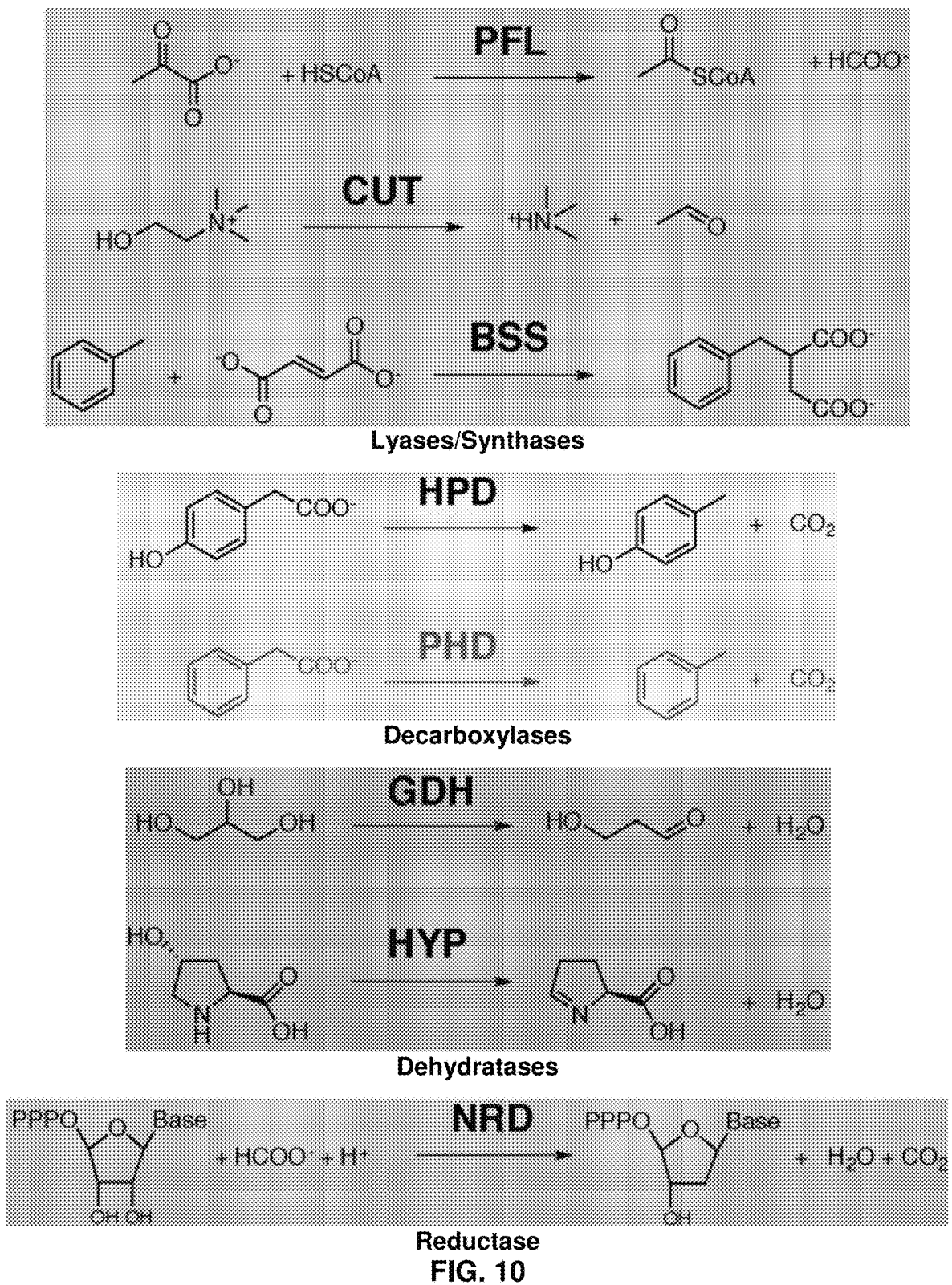
FIG. 10. Reactions catalyzed by characterized GREs. PFL, pyruvate formate-lyase; CUT, choline trimethylamine-lyase; BSS, benzylsuccinate synthase; HPD, p-hydroxyphenylacetate decarboxylase; PHD, phenylacetate decarboxylase (this study); GDH, glycerol dehydratase; HYP, trans-4-hydroxy-L-proline dehydratase; and NRD, anaerobic ribonucleotide reductase.

With respect to p-hydroxyphenylacetate decarboxylase in particular, differences from PhdB are noteworthy, since these proteins might be expected to be very similar based on the seemingly analogous reactions that they catalyze (FIG. 10). Phenylacetate decarboxylase (PhdB) has only one subunit type, in contrast to p-hydroxyphenylacetate decarboxylase (CsdBC or HpdBC), which has two (FIG. 9), and does not share conserved CsdB residues postulated to interact with the para-hydroxy group (e.g., active-site residue E637 of CsdB[23]). Furthermore, p-hydroxyphenylacetate decarboxylase (CsdBC) does not act on phenylacetate[8], and conversely, PhdB has far lower activity on p-hydroxyphenylacetate than on phenylacetate. Based upon the sole structural feature that differentiates the substrates of PhdB and p-hydroxyphenylacetate decarboxylase (CsdBC/HpdBC), namely a para-hydroxy group, and its essential role in the proposed mechanism of the latter enzyme, it is likely that PhdB and CsdBC/HpdBC differ mechanistically. The Kolbe-type decarboxylation proposed for CsdBC[23,28] involves an unprecedented mechanism for p-hydroxyphenylacetate activation: a concerted abstraction of a proton from the para-hydroxy group by E637 and abstraction of an electron from the carboxyl group by C503[23]. Together, the proton and electron abstraction constitute a de facto H-atom abstraction, although the abstraction occurs in two distinct locations on the substrate molecule. Molecular modeling of the substrate-bound active sites of PhdB (based on homology modeling) and CsdBC (based on crystallographic data) indicates important conserved residues, such as the sites of the thiyl radical (C482 in PhdB and C503 in CsdB) and glycyl radical (G815 in PhdB and G873 in CsdB), but also important differences, such as a hydrophobic pocket in PhdB (including W495, Y691, and V693) accommodating the unsubstituted ring of phenylacetate and lacking the H536 and E637 residues in CsdB that are proposed to interact with the para-hydroxy group of p-hydroxyphenylacetate.

Just as PhdB represents a novel glycyl radical enzyme, PhdA represents a new glycyl radical activating enzyme. Whereas PhdA shares some characteristics of the cognate activating enzymes for the seven GREs described above, such as a conserved CxxxCxxC [4Fe-4S]-binding motif near the N-terminus of the protein (FIG. 11, Panel c), its sequence identity to these activating enzymes is relatively low (from ca. 23 to 42% for both the sewage and lake culture versions of PhdA). To date, studies have indicated that glycyl radical activating enzymes are not interchangeable but rather are specific to their cognate glycyl radical enzymes[16].

Identity of Toluene-Producing Bacterium

Figure 12A:
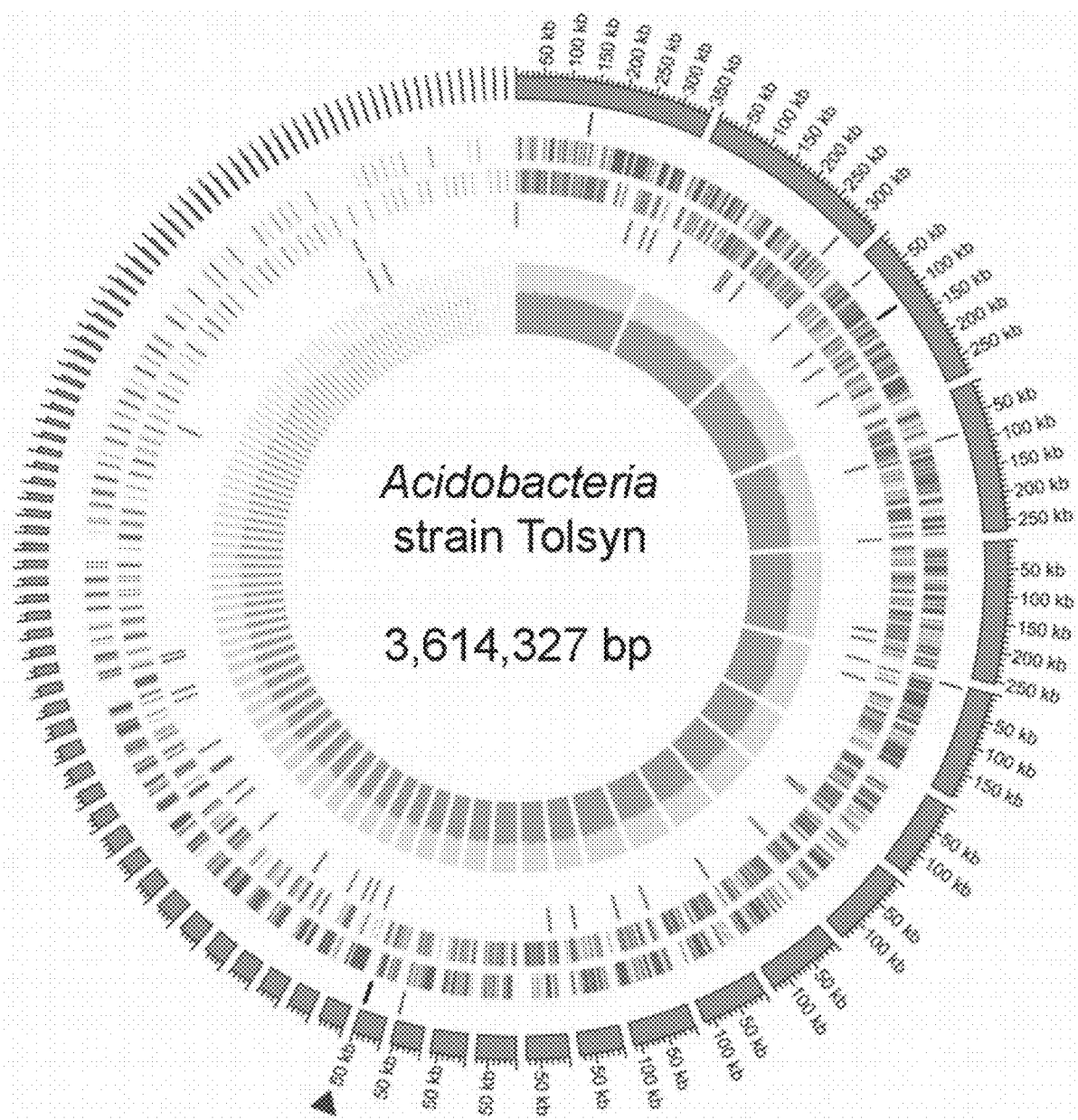
FIG. 12A. Characterization of the putatively toluene-producing *Acidobacterium* strain Tolsyn based on its recovered genome. Schematic circular diagram of the genome, with contigs in size order, displaying contigs and their corresponding lengths (outer ring), genes encoding radical-related enzymes (second ring; the contig containing phdA and phdB is indicated with a filled triangle), genes on the forward strand (third ring), genes on the reverse strand (fourth ring), tRNA genes (fifth ring), rRNA genes (sixth ring), and GC content (seventh ring; GC is averaged every 1000 bp and is represented as orange, whereas AT is light green).

As toluene synthase discovery is conducted with the proteome of a complex microbial community rather than that of a microbial isolate, the task of identifying the microbe whose genome encodes phdA and phdB was challenging. Nonetheless, one is able to recover the draft genome of the bacterium in the sewage community that putatively expressed phdA and phdB (FIG. 12A). This 3.61-Mbp genome (FIG. 12A), which results from co-assembly of Illumina reads from multiple metagenome sequences produced from the sewage culture, is estimated to be 96.35% complete and contains a 51.8-kb contig including the three-gene phd cluster (FIG. 9) relevant to toluene biosynthesis. In addition to phdA and phdB, the genome encodes other putative radical-related enzymes (FIG. 12A), including a GRE of unknown function and seven putative radical SAM enzymes that contain the CxxxCxxC motif near the N terminus.

Figure 12B:
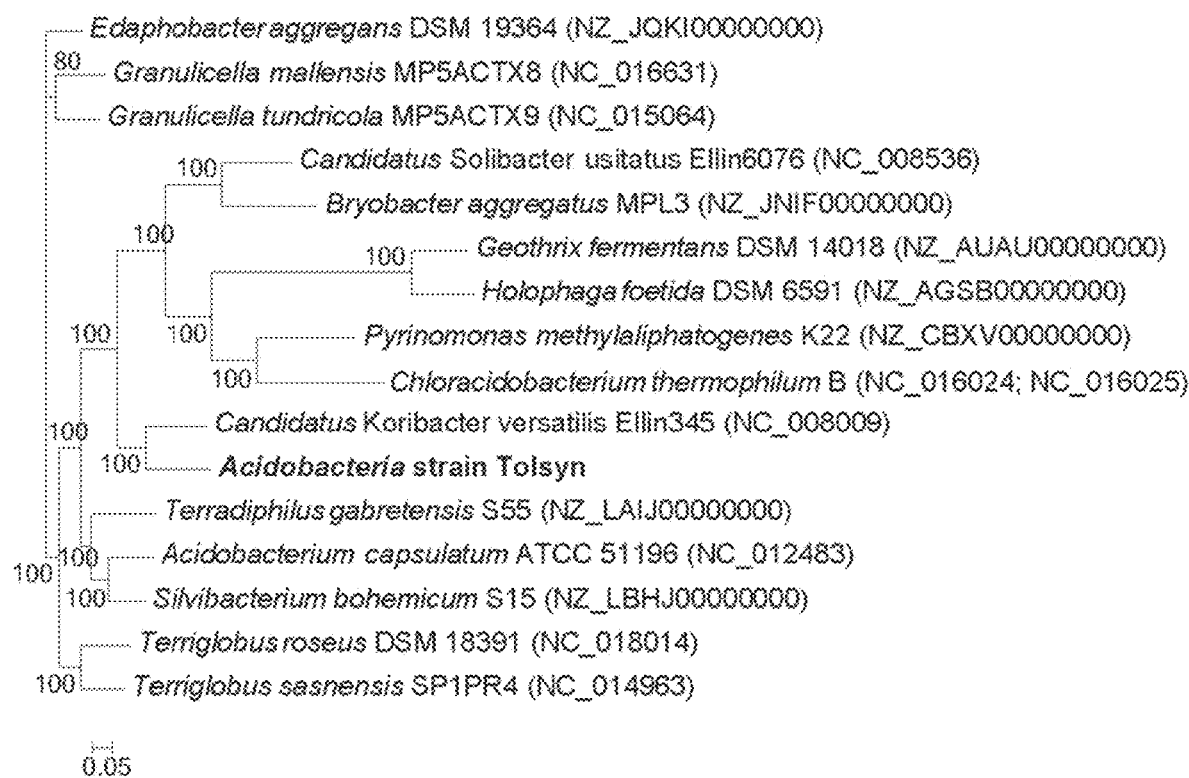
FIG. 12B. Characterization of the putatively toluene-producing *Acidobacterium* strain Tolsyn based on its recovered genome. Phylogenetic relationships among *Acidobacterium* strain Tolsyn and the most closely related Acidobacteria sequenced isolates based upon 129 concatenated marker proteins (GenBank accession numbers for species are shown in the tree). Numbers at nodes represent bootstrap support values. The scale bar represents substitution rate per site.

The recovered genome contains a partial 16S rRNA gene indicating that the toluene-producing bacterium (hereafter referred to as Acidobacteria strain Tolsyn) belongs to the Acidobacteria phylum. The closest match among bacterial isolates is to Candidatus *Koribacter versatilis* (95% identity), which is classified in Subdivision 1 of the Acidobacteria but is not well characterized with respect to its physiology and metabolism[29]. Evaluation of the recovered genome against the available Acidobacteria isolate genomes using 129 concatenated proteins (including 33 ribosomal proteins) indicates, as did the 16S rRNA analysis, that the closest isolated relative is Ca. *Koribacter versatilis* (FIG. 12B). However, the genomes of Acidobacteria strain Tolsyn and Ca. *Koribacter versatilis* are much less similar than the 16S rRNA comparison would suggest: average sequence identity for the proteins in these two genomes was only ca. 56%. Admittedly, there are few Acidobacteria isolates for comparison to strain Tolsyn, as Acidobacteria are notoriously difficult to isolate[29,30]. Notably, BLASTP[31] searches of the Ca. *Koribacter versatilis* genome did not yield any hits to PhdA or PhdB.

From an ecological perspective, the selective advantage conferred by toluene production in strain Tolsyn is currently unknown. The metabolic advantages rendered by phenylacetate conversion to toluene are not obvious, as the reaction yields only $CO_2$, which is unlikely to be limiting in environments like anoxic lake sediments or sewage sludge, and toluene, which is likely lost from the cell by diffusion and not further metabolized [e.g., benzylsuccinate synthase[22] was not found in the genome nor, indeed, in the entire sewage metagenome (IMG Taxon ID 3300001865)]. Here, two possible explanations for the selective advantage offered by toluene biosynthesis are presented. First, by analogy to p-hydroxyphenylacetate decarboxylation to p-cresol, as catalyzed by the nocosomial pathogen *Peptoclostridium difficile* (formerly *Clostridium difficile*), it is possible that toluene production represents a form of negative allelopathy. In *P. difficile*, production of the bacteriostatic agent p-cresol is thought to provide a competitive advantage to the producing strain and has been proposed as a virulence factor[32]. Just as the ultimate source of p-hydroxyphenylacetate to *P. difficile* is tyrosine metabolism, the source of phenylacetate to strain Tolsyn is likely phenylalanine metabolism[8], potentially involving transamination of phenylalanine to phenylpyruvate (e.g., via phenylalanine transaminase; EC 2.6.1.57), decarboxylation to phenylacetaldehyde (e.g., via phenylpyruvate decarboxylase; EC 4.1.1.43), and oxidation to phenylacetate (e.g., via phenylacetaldehyde dehydrogenase; EC 1.2.1.39)[33], although other pathways are possible[34]. Notably, BLASTP searches of the Acidobacteria strain Tolsyn genome did not reveal definitive copies of genes encoding any of these enzymes, suggesting that the conversion of phenylalanine to phenylacetate may not occur within strain Tolsyn, but rather that phenylacetate may be imported from its environment. Regardless of which microorganisms are converting phenylalanine to phenylacetate, previous studies have documented that the conversion of labeled phenylalanine (L-phenylalanine-β-$^{13}$C) to labeled toluene ([methyl-$^{13}$C] toluene) definitively occurs in this sewage culture[8].

The prospect of phenylacetate import into Acidobacteria strain Tolsyn introduces a second possible explanation for the selective advantage offered by toluene biosynthesis: intracellular pH homeostasis and/or development of a proton motive force (pmf). If the anion phenylacetate are imported into the cell, the PhdB-catalyzed decarboxylation to toluene consumes a proton from the cytoplasm (consistent with the balanced reaction of $C_8H_7O_2^-+H^+ \rightarrow C_7H_8+CO_2$), and the neutral reaction products toluene and $CO_2$ (or $H_2CO_3$) exits the cell (e.g., by diffusion), the result would be alkalinization of the cytoplasm and indirect development of a pmf (by depletion of protons from the cytoplasm rather than the canonical pumping of protons across the cytoplasmic membrane). Studies of tyrosine and histidine decarboxylation in *Enterococcus* and *Lactobacillus* spp. have experimentally supported analogous mechanisms for pmf development and intracellular pH regulation[35,36]. Thus, alkalinization of the cytoplasm via phenylacetate decarboxylation could promote tolerance to the moderately acidic conditions characteristic of some fermentative environments (such as those used to cultivate the sewage and lake sediment cultures and likely representative of their native habitats) and could also provide a source of energy to the bacterium (as pmf), even though the PhdB reaction would not provide reducing equivalents to the host because it is not an oxidation-reduction reaction.

Conclusion

A GRE that catalyzes an activity heretofore unavailable to biotechnology is discovered, enabling biochemical synthesis of toluene (and potentially other products of aromatic acid decarboxylation) from renewable feedstocks. Furthermore, this example, like the recent discovery of another GRE (trans-4-hydroxy-L-proline dehydratase[26]), provides a glimpse into the untapped catalytic potential of GREs. It is likely that the catalytic diversity of GREs has been widely underestimated because automated annotation pipelines routinely misidentify diverse GREs as pyruvate formate-lyase (as was the case for PhdB), and there is a dearth of experimental data to correct such misannotation. To illustrate the unexplored diversity of GREs, consider the sewage-derived microbial community investigated in this example. In addition to PhdB, it is conservatively estimated that there are at least four other novel GREs represented in the sewage culture metagenome (FIG. 8). These GREs deviate from known GREs with respect to at least one conserved residue, and share only ca. 16 to 38% protein sequence identity with known GREs and each other. All four of these putatively novel GREs were misannotated as pyruvate formate-lyase by an automated pipeline. Further experimental characterization of the catalytic range of GREs promises to expand our understanding of the metabolic diversity of anaerobic bacteria and the reach of biotechnology to catalyze challenging reactions.

Methods

Unless stated otherwise, all cultivation and biochemical processes are conducted under strictly anaerobic conditions[37] in an anaerobic glove box (Type B, Coy Laboratory Products, Inc., Grass Lake, Mich.) with a nominal gas composition of 85% $N_2$-10% $CO_2$-5% $H_2$ (ultra-high purity, anaerobic mixture) maintained at ambient temperature (~22° C.). Glass, plastic, and stainless steel materials used to manipulate microbial cells, cell-free extracts, and purified enzymes in the glove box are allowed to degas in the anaerobic glove box for at least one day before use, as are heat-labile solids that cannot be prepared in autoclaved and purged solutions. Highly purified water (18 MΩ resistance) obtained from a Barnstead Nanopure system (Thermo Scientific, Waltham, Mass.) is used to prepare all aqueous solutions described. Chemicals used in this example are of the highest purity available and are used as received.

Cultivation of Anaerobic Sewage and Lake Sediment Cultures

Anaerobic cultivation of sewage-derived cultures has been described previously[8]. In a similar fashion, reducing sediments from a lake in Berkeley, Calif., were used to inoculate cultures under anaerobic conditions using TP[9] or modified TP[8] growth medium in an anaerobic glove box. Amended phenylacetate (typically 200 μM) and evolved toluene were monitored by LC/MS and GC/MS, respectively, using methods described previously[8].

Partial Purification of Phenylacetate Decarboxylase Activity in Sewage Cultures with FPLC As described in detail elsewhere[8], cell-free extracts from the sewage-derived culture are generated under strictly anaerobic conditions with a French pressure cell[19] (138 MPa) and clarified by ultracentrifugation, before subjected to FPLC fractionation in an anaerobic glove box with a Bio-Scale Mini CHT-II ceramic hydroxyapatite column (5-mL bed volume, 40-μm particle diameter; Bio-Rad, Hercules, Calif.) and Bio-Rad Econo Gradient Pump. Phenylacetate decarboxylase activity in FPLC fractions is determined with a GC/MS static headspace assay that measured conversion of phenylacetic acid-2-$^{13}$C (Icon Isotopes, Summit, N.J.; 99 atom % $^{13}$C) to [methyl-$^{13}$C]toluene[8].

Proteomic Analysis of FPLC Fractions by LC/NIS/NIS

Details on proteomic analysis of selected FPLC fractions, including data processing, are provided by Zargar et al.[8] Briefly, proteomic LC/MS/MS analysis is performed with a Q Exactive Orbitrap mass spectrometer (Thermo Scientific) in conjunction with a Proxeon Easy-nLC II HPLC (Thermo Scientific) and Proxeon nanospray source.

Characterization of Sewage and Lake Cultures by Next-Generation Sequencing of Metagenomes and PCR-Amplified 16S rRNA Genes Extraction of genomic DNA from toluene-producing cultures is performed with a bead-beating method involving hexadecyltrimethylammonium bromide (CTAB) extraction buffer described elsewhere[8]. Genomic DNA is purified with Allprep DNA/RNA kits (Qiagen, Valencia, Calif.). The automated annotation pipeline for metagenome sequences is described previously[38].

Composition of the sewage-derived community is analyzed by Illumina sequencing of 16S rRNA genes amplified from the V4 region (primers 515F and 806R). Library construction and sequencing methods, and data analysis with iTagger v. 1.1, are performed as described previously[8].

Composition of the lake sediment-derived community is also assessed by Illumina sequencing of 16S rRNA genes amplified from the V4 region (primers 515F and 806R). Library construction is performed according to the Earth Microbiome Project standard protocol (webpage for: earthmicrobiome.org/protocols-and-standards/16s/). Sequencing is conducted on the Illumina MiSeq platform (San Diego, Calif.) with paired-end, 300-bp reads (MiSeq Reagent Kit v3, 600 cycle). The UPARSE method is used for sequence processing and operational taxonomic unit (OTU) clustering at 97% identity to process raw sequences (fastq_maxdiffs=3, fastq_trunclen=250, fastq_maxee=0.1). A set of 217 OTUs from a total of 108,041 filtered sequences are identified. For each OTU, a representative sequence is selected as described by Edgar[39]. Taxonomic assignments are made with a Naïve Bayes Classifier using the V4 region of the SILVA[40] SEED sequences and their taxonomic identities as a training set.

Cloning, Expression, In Vitro Reconstitution, and Purification of PhdA and PhdB

Strains and plasmids along with their associated information (annotated GenBank-format sequence files) are deposited in the public version of the JBEI Registry (webpage for: public-registry.jbei.org). Restriction enzymes are purchased from Thermo Scientific (Waltham, Mass.), and Phusion DNA polymerase and T4 ligase were from New England Biolabs (Ipswich, Mass.). Plasmid extractions are carried out using Qiagen (Valencia, Calif.) miniprep kits. Oligonucleotide primers are designed using the web-based PrimerBlast program (webpage for: ncbi.nlm.nih.gov/tools/primer-blast/index.cgi? LINK_LOC=BlastHomeAd) and synthesized by Integrated DNA Technologies (IDT), Inc. (San Diego, Calif.) or Eurofins MWG Operon (Huntsville, Ala.).

phdA and phdB are codon optimized (GenScript, Piscataway, N.J.) for expression in *E. coli* BL21(DE3). Each codon-optimized gene is individually cloned into plasmid pET28b (Novagen, Madison, Wis.). phdA is cloned between NdeI and BamHI restriction sites, resulting in a construct that encodes an N-terminal His$_6$-PhdA protein (pAS004). phdB was cloned between NdeI and XhoI restriction sites. To enhance soluble PhdB yield, the construct also includes the gene encoding maltose-binding protein (MBP) and a sequence encoding the tobacco etch virus (TEV) protease recognition site, which are inserted downstream of the N-terminal His$_6$ sequence and upstream of the phdB start codon, resulting in a construct that encodes a His$_6$-MBP-PhdB fusion protein with a TEV protease-cleavable His$_6$-MBP tag (pAS010). Plasmids are transformed into chemically competent *E. coli* DH10B cells grown on lysogeny broth (LB) agar plates under 50 μg/mL kanamycin selection (LB Kan-50 plates; Teknova, Hollister, Calif.). Plasmids are sequence-confirmed (Genewiz, South San Francisco, Calif.). Plasmids pAS004 (with phdA) and pAS010 (with phdB) are separately transformed into chemically competent *E. coli* BL21(DE3) cells (New England Biolabs) on LB Kan-50 plates. Transformants are grown in LB broth (supplemented with kanamycin) and stored as 100 μL glycerol stock aliquots at −80° C.

For overexpression of PhdA, a frozen glycerol stock of strain AS013 is used to inoculate 50 mL LB broth containing 50 µg/mL kanamycin (Teknova) in a 250-mL shake flask. The starter culture is incubated overnight at 30° C. with constant shaking at 200 rpm. For larger scale growth, the starter culture is diluted 100-fold in a 2-L baffled shake flask containing 1 L LB broth supplemented with 50 µg/mL kanamycin, and grown aerobically at 37° C. with constant shaking (190 rpm). At $OD_{600}$~0.7, the culture is induced with isopropyl β-D-1-thiogalactopyranoside (IPTG; IBI Scientific, Peosta, Iowa) to a final concentration of 0.5 mM and supplemented with an aqueous solution of $Fe(NH_4)_2(SO_4)_2.6H_2O$ (Sigma, St. Louis, Mo.; prepared anaerobically) to a final concentration of 200 µM. Following induction, the temperature is decreased to 18° C. and the culture is propagated overnight at this temperature for ~18 hours. Cells are then harvested by centrifugation and cell pellets are stored at −80° C. until lysis.

For overexpression of PhdB, strain AS019 is cultivated in autoinduction medium[41]. A frozen glycerol stock is used to inoculate 50 mL ZYP-0.8 G medium containing 100 µg/mL kanamycin in a 250-mL shake flask incubated overnight at 30° C. with constant shaking (200 rpm). The starter culture is diluted 100-fold into a 2-L baffled shake flask containing 1-L ZYP-5052 medium with 100 µg/mL kanamycin and grown aerobically at 37° C. with constant shaking at 190 rpm. At $OD_{600}$ ~1.5, the temperature is decreased to 18° C. and the culture is propagated overnight at this temperature for ~18 hours. Cells are then harvested by centrifugation and cell pellets are stored at −80° C. until lysis.

All purification steps are carried out under strictly anaerobic conditions. For lysis, cells are passed three times through a French pressure cell (138 MPa) under anaerobic conditions. Sealed lysates are centrifuged under anaerobic conditions at 19,000 rpm at 4° C. for 40 min. Clarified lysates are purified within an anaerobic glove box as described below using an Econo-Gradient pump coupled with a model 2110 fraction collector (Bio-Rad).

For PhdA purification, strain AS013 cell pellets are resuspended in buffer A [50 mM TRIS (pH 7.5; EMD Millipore, Billerica, Mass.), 300 mM NaCl (EMD Millipore), 10 mM imidazole (Sigma), 0.1 mM DL-dithiothreitol (DTT; VWR, Visalia, Calif.)] and mixed with powdered protease inhibitors (Pierce EDTA-free tablets, Thermo Scientific), chicken egg lysozyme (300 µg/mL, Sigma) and DNaseI (10 µg/mL, Sigma). This mixture is incubated for 20 min followed by cell lysis and clarification of the lysate as described above. The clarified lysate is filtered through a 0.45-µm filter (EMD Millipore) and loaded onto a 5-mL HisTrap HP column (GE Healthcare, Chicago, Ill.) that is pre-equilibrated with buffer A. The column is then washed with 3 column volumes (CV) of buffer A to remove unbound proteins and eluted using a stepwise imidazole gradient made by mixing buffer A with buffer B [50 mM TRIS (pH 7.5), 300 mM NaCl, 500 mM imidazole, 0.1 mM DTT] using stepwise concentrations of 20 mM, 50 mM, 250 mM, and 400 mM imidazole. Each step is set to 1.6 CV and 2-mL fractions are collected. Fractions containing PhdA are dark red-brown and eluted at a concentration of 250 mM imidazole. The purity of PhdA fractions is confirmed by SDS-PAGE. Elution fractions are pooled and DTT is added to a final concentration of 2 mM. To keep the protein anoxic during concentration outside the glove box, a 10-kDa molecular weight cutoff (MWCO) concentrator (EMD Millipore) is sealed inside a 250-mL centrifuge bottle (Nalgene, Rochester, N.Y.) with an O-ring-sealed cap. Concentrated protein is exchanged into buffer C [50 mM TRIS (pH 7.5), 300 mM NaCl, 5 mM DTT] using a pre-equilibrated PD-10 desalting column (GE Healthcare). Protein concentration is determined using the Bradford assay (Bio-Rad). Collected UV-visible spectra (UV-2450; Shimadzu Scientific, Pleasanton, Calif.) indicated the presence of [2Fe-2S] clusters bound to the protein[42].

For reconstitution of [4Fe-4S] clusters in PhdA, which are required for activity, the protein was diluted to 0.2 mM in buffer C in a stoppered serum bottle and cooled to 4° C. DTT was then added to a final concentration of 10 mM and the solution was incubated at 4° C. for ~1 hour. Aqueous $Fe(NH_4)_2(SO_4)_2.6H_2O$ was added to a final concentration of 1 mM and incubated at 4° C. for ~3-4 hours. Aqueous $Na_2S.9H_2O$ was then added to a final concentration of 0.9 mM and the mixture was incubated at 4° C. overnight (~18 hr). The protein mixture was then filtered through a 0.45-µm filter, concentrated, and diluted 15-fold in buffer D [50 mM TRIS (pH 7.5), 20 mM NaCl, 2 mM DTT]. The diluted protein was then loaded onto a 5-mL Bioscale High Q column (Bio-Rad) that was pre-equilibrated with buffer D and eluted using buffer E [50 mM TRIS (pH 7.5), 1 M NaCl, 2 mM DTT] with a stepwise NaCl gradient of concentrations 40 mM, 100 mM, 500 mM, and 800 mM NaCl. Each step was set to 1.6 CV and 2-mL fractions were collected. PhdA eluted at a concentration of ~500 mM NaCl and fractions were yellow-brown. Purity of eluted fractions was confirmed by SDS-PAGE. Pooled fractions were concentrated and exchanged into assay buffer [50 mM TRIS (pH 7.5), 150 mM NaCl, 1 mM $MgCl_2$ (Sigma), 5 mM $(NH_4)_2SO_4$ (Sigma), 5 mM DTT] using a pre-equilibrated PD-10 column and stored at 4° C. in a stoppered serum bottle. Protein concentration was determined using the Bradford assay. UV-visible spectra confirmed the presence of [4Fe-4S] clusters bound to the protein[42].

For PhdB purification, strain AS019 cell pellets were washed in buffer containing 50 mM TRIS (pH 7.5), 150 mM NaCl, and 0.5 mM dithionite. For purification, cell pellets were resuspended in buffer A [20 mM TRIS (pH 7.5), 200 mM NaCl, 1 mM EDTA (EMD Millipore), 1 mM DTT] and mixed with powdered protease inhibitors, chicken egg lysozyme (1 mg/mL) and DNaseI (10 µg/mL). This mixture was incubated for 30 minutes, followed by cell lysis with a French pressure cell under anaerobic conditions and clarification of the lysate as described for PhdA. The clarified lysate was filtered through a 0.45-µm filter (Millipore) and loaded on to a 5 mL-MBPTrap HP column (GE Healthcare) that was pre-equilibrated with buffer A. The column was then washed with 3 CV of buffer A to remove unbound proteins and eluted using a program consisting of a stepwise maltose gradient made by mixing buffer A with buffer B [20 mM TRIS (pH 7.5), 200 mM NaCl, 1 mM EDTA, 10 mM maltose (Sigma), 1 mM DTT] using concentrations of 0.4 mM, 1 mM, 5 mM, and 8 mM maltose. Each step was set to 1.6 CV and 1-mL fractions were collected. PhdB eluted at a concentration of ~1 mM maltose and purity of fractions was confirmed by SDS-PAGE. Elution fractions were pooled and DTT was added to a final concentration of 2 mM and the protein was concentrated anaerobically as described for PhdA (except with a 50-kDa MWCO rather than 10-kDa MWCO filter). Concentrated protein was exchanged into assay buffer [50 mM TRIS (pH 7.5), 150 mM NaCl, 1 mM $MgCl_2$, 5 mM $(NH_4)_2SO_4$, 5 mM DTT)] using a pre-equilibrated PD-10 desalting column (GE Healthcare). Protein concentration was determined using the Bradford assay (Bio-Rad). During initial purifications, protein identity was confirmed by Western blotting using 6× His-tag monoclonal primary antibody and HRP-conjugated secondary antibody (Thermo Fisher Scientific) for PhdA and PhdB. To confirm the MBP-tagged PhdB construct, HRP-conjugated anti-MBP antibody (New England Biolabs) was used. Protein bands were visualized using Clarity Western ECL Substrate (Bio-Rad) using a chemiluminescence imager (Amersham Imager 600, GE Healthcare)

Site-Directed Mutagenesis of PhdB to Create G815A Mutant

Plasmid pAS010 was used as a template for mutating the radical-propagating Gly-815 residue in PhdB to alanine. Site-directed mutagenesis was performed using the QuikChange Lightning kit (Agilent, Santa Clara, Calif.), using protocols recommended by the manufacturer. The G815A mutation was confirmed by plasmid sequencing (Illumina MiSeq platform). The resulting plasmid, pAS013, was transformed into chemically competent BL21(DE3) cells (New England Biolabs) (strain AS022). Growth and protein purification protocols used for the mutant PhdB G815A were identical to those used for wild-type PhdB.

Anaerobic In Vitro Assays for PhdA Activity with Recombinant Protein

In an anaerobic chamber at ambient temperature, 0.7 mM reconstituted PhdA was incubated in assay buffer [50 mM TRIS (pH 7.5), 150 mM NaCl, 1 mM $MgCl_2$, 5 mM $(NH_4)_2SO_4$, 5 mM DTT] with 2 mM dithionite (Sigma) for 1 hour in 4-mL screw-capped glass vials (Supelco). This was followed by the addition of 2 mM SAM [S-(5'-adenosyl)-L-methionine chloride dihydrochloride; Sigma]. The reaction mixture (1.2 mL) was shaken at low speed on a tabletop orbital shaker. Upon initiation of the PhdA reaction by SAM addition, sampling was conducted from 0 to 180 min at 30-min intervals. Immediately after sampling, 75 µL of reaction mixture was quenched by addition of 75 µL LC/MS grade methanol (Honeywell Research Chemicals, Muskegon, Mich.) and gentle bubbling of 0.5 mL of air (from a sealed serum bottle). Control reaction mixtures excluding PhdA were assayed in an identical manner. Post quenching, samples were centrifuged at 13,000 rpm for 15 min, then diluted in 50% (v/v) methanol in LC/MS grade water (J. T. Baker, Phillipsburg, N.J.) in preparation for LC/MS measurement. Replicates involved separate assays rather than multiple analyses of a given assay sample.

For analysis of methionine produced by PhdA activity with SAM, external standard quantification was performed with five-point calibration standards ranging from 0.25-10 µM methionine (Sigma) in 50/50 (v/v) methanol/water. Samples were run on an LC/MSD SL (Agilent) equipped with a model 1260 Infinity Binary Pump and operated in the electrospray ionization, positive-ion mode. The mobile phase initially flowed at 0.6 mL/min (0-13 min), and later at 1 mL/min (13-15 min), through a Kinetex HILIC column (2.6 µm particle size, 4.6-mm inner diameter×50-mm length; Phenomenex, Torrance, Calif.). The initial mobile phase composition was 10 vol % A (20 mM ammonium acetate in water) and 90 vol % B (10 mM ammonium acetate in 90% acetonitrile, 10% water), which was decreased linearly to 70% B at 4 minutes, then decreased linearly to 40% B from 6-11.5 minutes, and then increased linearly to 90% B from 12-15 minutes to re-equilibrate the column to initial conditions. Sample injection volume was 2 µL. Source conditions included 3.5 kV capillary voltage, 250° C. drying gas temperature, 12 L/min drying gas flow, and 25 psig nebulizer pressure. Data acquisition for methionine was in the selected ion monitoring (SIM) mode at m/z 150.2. Peak areas were integrated using Mass Hunter software (Agilent, version B.05.00).

Anaerobic In Vitro Assays for Phenylacetate Decarboxylase Activity with Recombinant PhdA and PhdB Assays for phenylacetate decarboxylase activity were performed under strictly anaerobic conditions within a glove box. Assays, which were performed in 4-mL glass vials sealed with 13-mm diameter PTFE Mininert screw-cap valves (Sigma-Aldrich), contained 250 µM PhdA in assay buffer [50 mM TRIS (pH 7.5), 150 mM NaCl, 1 mM $MgCl_2$, 5 mM $(NH_4)_2SO_4$, 5 mM DTT)], to which 2 mM dithionite was added and incubated for ~1 hour, followed by the addition of 2 mM SAM, 2.5 µM PhdB in assay buffer, and 2.5 mM phenylacetic acid-2-$^{13}$C in a final volume of 1 or 1.5 mL (depending on the specific experiment). Quantitative standards contained the same headspace/liquid ratios as assays and a dimensionless Henry's constant of 0.27[43] was used to calculate aqueous concentration. Negative controls were run concurrently and were identical except for the absence of SAM (FIG. 6). The vials were shaken on a tabletop orbital shaker at low speed. Gaseous headspace samples (100 µL) were taken within the glove box using a 500-µL gastight syringe (Sample-Lok series A-2; Sigma-Aldrich) and analyzed immediately by GC/MS, as described previously[8]. Briefly, toluene was analyzed by static headspace, electron ionization (EI) GC/MS using a model 7890A GC (Agilent, Santa Clara, Calif.) with a DB-5 fused silica capillary column (30-m length, 0.25-mm inner diameter, 0.25-µm film thickness; Agilent) coupled to an HP 5975C series quadrupole mass spectrometer. As described elsewhere[8], the identity of [methyl-$^{13}$C]toluene was confirmed with the expected m/z 93/92 ratio of 0.6. Replicates involved separate assays rather than multiple analyses of a given assay sample. In assays testing whether PhdB could decarboxylate o-, m-, or p-hydroxyphenylacetate to o-, m-, or p-cresol, conditions were as described above except that equimolar amounts (2.5 mM) of o-, m-, or p-hydroxyphenylacetic acid (Sigma) and phenylacetic acid-2-$^{13}$C were added, and GC/MS analysis of o-, m-, or p-cresol in 1-µL liquid injections of concentrated hexane extracts were conducted as described previously[8]. The identity of o-, m-, or p-cresol was assessed using retention time and the expected m/z 108/107 ratio of 1.16, 1.05, or 0.83, respectively, based on authentic standards.

PCR Amplification of Phd Gene Cluster from Genomic DNA from Lake Sediment Culture phdA, phdB, and an adjacent putative transcription factor were PCR-amplified from genomic DNA extracted from the lake sediment community using primers. Primer design was guided in part by partial gene sequences available from metagenomes (IMG Taxon ID 2100351000 and 3300001865). Amplified and gel-purified DNA was sequenced by Genewiz.

Construction of Maximum Likelihood Tree of Glycyl Radical Enzymes in Sewage-Derived Culture The maximum-likelihood tree in FIG. 8 encompasses protein sequences of putative glycyl radical enzymes (GREs) detected in the sewage culture metagenome (IMG Taxon ID 3300001865) based on BLASTP[31] searches against known GREs (>30% sequence identity), searches for the glycyl radical motif (FIMO[44]), and a minimum length of 171 amino acids (not all were full length). The following model sequences were also included in the tree to provide context (accession numbers in parenthesis): PflB (GenBank: NP_415423), HpdB (GenBank: AJ543425.1), CsdB (GenBank: ABB05046.1), CutC (PDB: 5A0Z), NrdD (GenBank: NP_418659), and Gdh (PDB: 1R8W). The collected set of model and putative GRE sequences (n=81, mean=675±194 aa) were aligned using MUSCLE v. 3.8.31[45]. The resulting MSA was screened for ambiguous C and N termini as well as columns with >97% gaps. The final alignment spanned 1138 columns. A maximum likelihood phylogenetic tree was inferred with RAxML v. 7.6.3[46], under the LG plus Gamma model of evolution as follows:

raxmlHPC-PTHREADS-SSE3-#50 -m PROTGAM-MAGTR -p 777 -x 2000 -f

The tree was constructed with iTOL[47].

Binning of Sewage Culture Metagenomes and Recovery of Acidobacteria Strain Tolsyn Genome For binning, two groups of sewage metagenomes (Group 1 from SRA accession numbers SRP077640, SRP072654, and SRP099295 and Group 2 from SRA accession numbers SRP105442 and SRP105443) were separately co-assembled using metaSPAdes v3.6[48] with the "- -careful" option. The two co-assemblies were separately binned using MaxBin 2.0[49] with default parameters (-min_contig_len 1000). The Acidobacteria strain Tolsyn bins were separately identified within the two co-assemblies, and scaffolds that were shared (with >98% identity) were selected to constitute the draft Acidobacteria genome. The scaffolds were further refined by mapping against the hybrid assemblies of the sewage sludge samples (IMG Taxon ID 3300017643, 3300017642, and 3300017814) and extracting scaffolds that unambiguously connected two or more sequences in the draft Acidobacteria genome. Genes were predicted from the genome using Prodigal (parameter: -p meta)[50]. Amino acid sequence identity between the draft Tolsyn genome and the Ca. *Koribacter versatilis* genome was carried out by comparing predicted proteins from the two genomes using BLASTP[31] with an e-value cutoff of 1e-10 and coverage cutoff 0.4. Annotation was performed by matching identical genes identified by the IMG pipeline (IMG Taxon ID 3300001865) using BLASTP with minimum amino acid identity set to 95% and minimum coverage set to 40%; the best matching IMG annotations were then assigned for those genes. CheckM software[51] reported that the genome was 96.35% complete with a contamination ratio of 1.69%. The circular genome plot (FIG. 12A) was made using Circos[52]. The 16S rRNA gene was identified as follows. A partial 16S rRNA gene (756 bp) was identified in a 1.7-kb scaffold and was 100% identical to a 16S rRNA gene identified from 16S rRNA iTag analysis: Acidobacteria OTU (Operational Taxonomic Unit) #9.

When OTU9 was used as query sequence for BLASTN searches of the sewage culture metagenome (IMG Taxon ID 3300001865), it had a 100% match with scaffold JGI2065J20421_1000212, which contained a 1382-bp 16S rRNA gene (JGI2065J20421_10002126). As a result, the partial 16S rRNA gene in the Acidobacteria strain Tolsyn genome was replaced by the 1382-bp 16S rRNA gene.

Construction of Phylogenetic Trees for Acidobacteria Strain Tolsyn

The 16S rRNA tree was constructed by aligning selected 16S rRNA gene sequences using MUSCLE[45] and then applying FastTree[53] to the alignment file. The concatenated protein tree (FIG. 12B) was constructed with ezTree (webpage for: github.com/yuwwu/ezTree), a pipeline for identifying single-copy marker genes from a collection of complete or draft genomes and using the marker genes to generate a concatenated protein tree.

Molecular Modeling of PhdB in Complex with its Phenylacetate Substrate

A molecular model of PhdB was created using homology modeling of three-dimensional protein structures implemented in the program SWISS-MODEL[54]. The GRE 1,2-propanediol dehydratase from *Roseburia inulinivorans* (PDB ID: 5I2A), which shares 32% sequence identity with PhdB, was used as a template to generate a molecular model of PhdB. Superposition of the CsdB in complex with p-hydroxyphenylacetate (PDB ID: 2YAJ)[28] with the molecular model of PhdB was performed with the program COOT[55] to extract the binding position of phenylacetate. A structure idealization of the PhdB-phenylacetate complex was performed with REFMAC[56] to generate the final molecular model of the complex. The overall stereochemical quality of the final models was assessed using the program MolProbity[57].

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

---

What is claimed is:

1. A genetically modified host cell comprising a first polypeptide comprising an amino acid sequence having at least 90% amino acid sequence identity to the amino acid sequence of SEQ ID NO:1 or SEQ ID NO:2 and a conserved qlycyl radical motif comprising R at position 812, V at position 813, G at position 815, F at position 816, L at position 823, Q at position 828, I at position 831, and R at position 834, and a conserved C at position 482, of the amino acid sequence of SEQ ID NO:1 or SEQ ID NO:2, and having an enzymatic activity to decarboxylate a phenylacetic acid into a toluene and a carbon dioxide, and a second polypeptide comprising an amino acid sequence having at least 90% amino acid sequence identity to the amino acid sequence of SEQ ID NO:3 or SEQ ID NO:4 and conserved amino acid residues: C at position 33, C at position 37, and C at position 40 of the amino acid sequence of SEQ ID NO:3, or C at position 39, C at position 43, and C at position 46 of the amino acid sequence of SEQ ID NO:4, and having an enzymatic activity to cleave a S-adenosylmethionine (SAM) to form a methionine and a 5'-deoxyadenosyl radical, wherein said 5'-deoxyadenosyl radical can activate the first polypeptide; wherein the first polypeptide or the second polypeptide is heterologous to the genetically modified host cell.

2. The genetically modified host cell of claim 1, wherein the conserved glycyl radical motif of the first polypeptide comprises the amino acid sequence RVXGX$_{12}$QX$_5$R (SEQ ID NO:5), RVAGFX$_6$LX$_4$QX$_2$IX$_2$R (SEQ ID NO:6), or RVAGFSAYFITLCPEVQXEIVSR (SEQ ID NO:7).

3. The genetically modified host cell of claim 1, wherein the first polypeptide comprises the amino acid sequence GCVXSG (SEQ ID NO: 9) or GCVQQSIIGG (SEQ ID NO: 10).

4. The genetically modified host cell of claim 1, wherein the second polypeptide comprises the amino acid sequence CXXXCXXC (SEQ ID NO: 10), CXXXCXXCXN (SEQ ID NO:11), CPLRCLWC (SEQ ID NO:12), GXRX3FX2 GCX3CX2CXN (SEQ ID NO: 13), or FLKGCPLRCLWCSNPE (SEQ ID NO:14).

5. A genetically modified host cell comprising a first nucleic acid encoding a first polypeptide operatively linked a first promoter, wherein the first polypeptide comprises an amino acid sequence having at least 90% amino acid sequence identity to the amino acid sequence of SEQ ID NO:1 or SEQ ID NO:2 and a conserved qlycyl radical motif comprising R at position 812, V at position 813, G at position 815, F at position 816, L at position 823, Q at position 828, 1 at position 831, and R at position 834, and a conserved C at position 482, of the amino acid sequence of SEQ ID NO:1 or SEQ ID NO:2, and having an enzymatic activity to decarboxylate a phenylacetic acid into a toluene and a carbon dioxide; and the first nucleic acid, or a second nucleic acid, encoding a second polypeptide operatively linked to the first promoter or a second promoter, wherein the second polypeptide comprises an amino acid sequence having at least 90% amino acid sequence identity to the amino acid sequence of SEQ ID NO:3 or SEQ ID NO:4 and conserved amino acid residues: C at position 33, C at position 37, and C at position 40 of the amino acid sequence of SEQ ID NO:3, or C at position 39, C at position 43, and C at position 46 of the amino acid sequence of SEQ ID NO:4, and having an enzymatic activity to cleave a S-adenosylmethionine (SAM) to form a methionine and a 5'-deoxyadenosyl radical; wherein the genetically modified host cell is capable of expressing the first and the second polypeptide and the first polypeptide or the second polypeptide is heterologous to (i) the genetically modified host cell, or (ii) the first promoter or the second promoter.

6. A method of producing a substituted or unsubstituted toluene or 2-methyl-1H-indole in a genetically modified host cell, the method comprising culturing the genetically modified host cell of claim 1 in a medium under a suitable condition such that the culturing results in the genetically modified host cell producing the substituted or unsubstituted toluene or 2-methyl-1H-indole.

7. The method of claim 6, wherein the medium comprises S-adenosylmethionine (SAM) and the genetically modified host cell uptakes or absorbs SAM and/or an unsubstituted or substituted phenylacetic acid from the medium.

8. The method of claim 6, wherein the genetically modified host cell is capable of endogenously synthesizing SAM and/or an unsubstituted or substituted phenylacetic acid from a carbon source.

9. The method of claim 6, further comprising introducing a first and/or second nucleic acids encoding the first and/or second polypeptide into the genetically modified host cell, wherein the introducing step is prior to the culturing step.

10. The method of claim 6, wherein the method further comprises separating the substituted or unsubstituted toluene or 2-methyl-1H-indole from the genetically modified host cell and/or the medium, wherein the separating step is subsequent, concurrent or partially concurrent with the culturing step.

11. The genetically modified host cell of claim 1, wherein the first polypeptide comprises an amino acid sequence having at least 95% amino acid sequence identity to the amino acid sequence of SEQ ID NO: 1 or SEQ ID NO: 2, and the second polypeptide comprises an amino acid sequence having at least 95% amino acid sequence identity to the amino acid sequence of SEQ ID NO: 3 or SEQ ID NO: 4.

12. The genetically modified host cell of claim 1, wherein the first polypeptide comprises an amino acid sequence having at least 99% amino acid sequence identity to the amino acid sequence of SEQ ID NO: 1 or SEQ ID NO: 2, and the second polypeptide comprises an amino acid sequence having at least 99% amino acid sequence identity to the amino acid sequence of SEQ ID NO: 3 or SEQ ID NO: 4.

13. The genetically modified host cell of claim 12, wherein the first polypeptide comprises the amino acid sequence of SEQ ID NO: 1 or SEQ ID NO: 2, and the second polypeptide comprises the amino acid sequence of SEQ ID NO: 3 or SEQ ID NO: 4.

* * * * *

SEQUENCE LISTING

```
<160> NUMBER OF SEQ ID NOS: 27

<210> SEQ ID NO 1
<211> LENGTH: 839
<212> TYPE: PRT
<213> ORGANISM: Unknown
<220> FEATURE:
<223> OTHER INFORMATION: The gene of this polypeptide was cloned from a
      sample selected and obtained from a sewage or lake

<400> SEQUENCE: 1

Met Ser Thr Gln Val Ser Gln His Ala Pro Lys Ala Pro Glu Gln Met
1               5                   10                  15

Pro Arg Lys Ile Lys Leu Asn Phe Asp Pro Asn Gly Lys Met Ser Asp
            20                  25                  30

Arg Phe Lys Lys Glu Lys Glu Leu Phe Ala Ala Pro Ala Arg Leu
        35                  40                  45

Asp Val Gln Lys Leu Gln Ile Glu Thr Asp Val Tyr Ser Lys Trp Ala
    50                  55                  60
```

```
Ala Ser Lys Ser Tyr Ser Glu Ile Lys Ala Met Ile Phe Asp Arg Leu
 65                  70                  75                  80

Ser Arg Glu Lys Lys Val Trp Leu Asp Gly Asn Pro Ile Cys Gly His
                 85                  90                  95

Leu Thr Asn Phe Ile Tyr Gly Gly Tyr Ile Gln Pro Trp Arg Asp Ser
                100                 105                 110

Tyr Trp Ile Glu Asp Lys Glu Phe Ala Leu Gln Arg Gly Val His
                115                 120                 125

Lys Thr Thr Glu Glu Glu Arg Lys Ile Ile Gln Glu Cys Gly Lys Phe
            130                 135                 140

Trp Ile Gly Gln Asn Met Gln Asp Arg Val Arg Pro Ile Val Lys Ala
145                 150                 155                 160

Lys Tyr Gly Leu Asp Val Gln Lys Leu Val Asp Ile Gly Leu Gly Leu
                165                 170                 175

Asn Phe Asp Asp Asp Met Gly Gly Met Val Val Pro Cys His Arg Thr
                180                 185                 190

Val Ile Glu Arg Gly Leu Glu Asp Val Leu Arg Gln Ile Ala Cys Val
            195                 200                 205

Lys Ser Lys Cys Lys Val Tyr Gly Val Gln Ala Pro Asp Pro Thr Ala
210                 215                 220

Gly Gln Val Pro Asn Glu Asn Thr Ile Leu Thr Ser Val Ser Pro Thr
225                 230                 235                 240

Ser Asp Tyr Lys Lys Trp His Phe Leu Cys Ala Cys Glu Val Ser Ile
                245                 250                 255

Lys Ala Leu Ile His Gln Ala Glu Arg Tyr Ala Ala Leu Ala Arg Glu
            260                 265                 270

Ala Ala Ala Ser Glu Lys Asp Pro Cys Lys Lys Ala Glu Tyr Glu Glu
            275                 280                 285

Met Ala Asp Arg Cys Ser Trp Val Pro Ala Lys Pro Ala Arg Thr Phe
290                 295                 300

Lys Glu Ala Leu Gln Ala Gln Trp Phe Ile Thr Met Gly Asp Trp Gln
305                 310                 315                 320

Asn Gln Cys Met Thr Val His His Ala Pro Met Arg Phe Pro Gln Tyr
                325                 330                 335

Val Tyr Ala Asn Tyr Lys Lys Asp Ile Glu Glu Gly Arg Ile Thr Asp
                340                 345                 350

Glu Glu Ala Ile Glu Phe Leu Gln Phe Trp Phe Leu Lys Val Asn Thr
            355                 360                 365

Gln Asn Phe Val Met Asn Pro Glu Leu Ala Ile Trp Gln Gln Ser Arg
            370                 375                 380

Ile Ala Gln Gln Leu Thr Leu Gly Gly Leu Asp Pro Ala Thr Gly Glu
385                 390                 395                 400

Asp Gly Thr Cys Glu Val Asp Tyr Leu Ile Leu Glu Ala Gln Arg Arg
                405                 410                 415

Ala Gln Cys Pro Glu Pro Leu Leu Ser Val Met Tyr His Asn Lys Leu
            420                 425                 430

Ser Pro Lys Phe Leu Met Glu Cys Val Lys Leu Ile Arg Thr Gly Ile
            435                 440                 445

Gly Gln Pro Ser Phe His Ser Gln Glu Val Ser Met Lys Arg Arg Leu
        450                 455                 460

Leu His Glu Glu Gly Pro Ile Glu Asp Ile Arg Asp Gln Ala Val Ala
465                 470                 475                 480
```

-continued

Gly Cys Val Gln Ser Ile Ile Gly Gly Lys Thr Asp Gly Thr Trp Glu
                    485                 490                 495

Ala Arg Phe Asn Met Thr Lys Met Met Glu Phe Phe Phe Ser Asn Gly
            500                 505                 510

Arg Asp Ile Lys Thr Gly Val Ala Tyr Gly Pro Ala Tyr Gly Asp Pro
            515                 520                 525

Cys Glu Cys Lys Thr Trp Glu Glu Cys Tyr Asp Arg Leu Tyr Lys Tyr
            530                 535                 540

Tyr Glu Tyr Trp Ile Asp Ile Cys Arg Asp Ile Ser Thr Leu Glu Trp
545                 550                 555                 560

Asn Met Glu Arg Asp His Pro Thr Pro Leu Gly Ser Ala Val Thr Tyr
                565                 570                 575

Asp Cys Val Glu Arg Gly Met Asp Met Val Asp Gly Gly Ala Arg Tyr
            580                 585                 590

Asn Trp Gly Asp Gly Val Cys Leu Ala Gly Ser Val Asp Ala Thr Asn
            595                 600                 605

Cys Leu Ala Ala Met Lys Lys Leu Ile Phe Asp Asp Lys Ser Val Ser
            610                 615                 620

Met Glu Lys Met Val Ala Ala Ile Thr Ala Asn Phe Val Gly Tyr Glu
625                 630                 635                 640

Asp Val Gln Asn Leu Cys Lys Lys Ala Pro Lys Tyr Gly Asn Asp Asp
                645                 650                 655

Pro Phe Ala Asp Glu Leu Gly Arg Arg Leu Met Arg Asp Tyr Ala Glu
            660                 665                 670

Ile His Asn Arg Lys Pro Asp Tyr Met Gly Arg Trp Thr Ile Thr Pro
            675                 680                 685

Ser Ala Tyr Ser Val Thr Ala His Trp Ala Phe Gly Lys Lys Thr Trp
            690                 695                 700

Ala Thr Pro Asp Gly Arg Lys Ala Gly Glu Cys Met Thr Asp Ala Thr
705                 710                 715                 720

Leu Ser Ala Thr Pro Gly Thr Asp Val Lys Gly Pro Thr Ala Leu Ile
                725                 730                 735

Arg Ser Ala Leu Lys Leu Ile Asp Pro Val Val Tyr Gly Ser Thr His
            740                 745                 750

Phe Asn Val Lys Phe His Pro Thr Ala Leu Glu Gly Glu Ala Gly Ala
            755                 760                 765

Gln Lys Phe Leu Gln Leu Val Lys Thr Tyr Phe Asp Gly Gly Gly Tyr
            770                 775                 780

Gln Ile Gln Phe Asn Cys Val Thr Gln Glu Thr Leu Arg Ala Ala Gln
785                 790                 795                 800

Lys Asp Pro Asp Ser Tyr Arg Asp Leu Ile Val Arg Val Ala Gly Phe
                805                 810                 815

Ser Ala Tyr Phe Ile Thr Leu Cys Pro Glu Val Gln Asp Glu Ile Val
            820                 825                 830

Ser Arg Thr Cys Gln Thr Trp
            835

<210> SEQ ID NO 2
<211> LENGTH: 839
<212> TYPE: PRT
<213> ORGANISM: Unknown
<220> FEATURE:
<223> OTHER INFORMATION: The gene of this polypeptide was cloned from a
      sample selected and obtained from a sewage or lake

<400> SEQUENCE: 2

```
Met Ser Thr Gln Val Thr Gln Lys Ala Pro Ala Pro Glu Gln Met
1               5                   10                  15

Pro Arg Lys Ile Lys Leu Thr Phe Asp Pro Asn Gly Lys Met Thr Asp
                20                  25                  30

Arg Phe Lys Lys Glu Lys Glu Lys Leu Phe Ala Ala Pro Ala Arg Leu
            35                  40                  45

Asp Val Gln Lys Leu Gln Ile Glu Thr Asp Val Tyr Ser Lys Trp Ala
50                  55                  60

Ala Ser Lys Ser Tyr Asn Glu Ile Lys Ala Met Ile Phe Asp Arg Leu
65                  70                  75                  80

Ser Arg Glu Lys Lys Val Trp Leu Asp Gly Asn Pro Ile Cys Gly His
                85                  90                  95

Leu Thr Asn Phe Val Tyr Gly Gly Tyr Ile Gln Pro Trp Arg Asp Ser
                100                 105                 110

Tyr Trp Ile Glu Asp Asp Lys Glu Phe Ala Leu Gln Arg Gly Val His
            115                 120                 125

Lys Thr Thr Ala Glu Glu Gln Lys Ile Ile Gln Glu Cys Gly Lys Phe
130                 135                 140

Trp Ile Gly Gln Asn Met Gln Asp Arg Val Arg Pro Ile Val Lys Ala
145                 150                 155                 160

Lys Tyr Gly Leu Asp Val Gln Lys Leu Val Asp Ile Gly Leu Gly Leu
                165                 170                 175

Asn Phe Asp Asp Asp Met Gly Gly Met Val Val Pro Asp His Arg Met
                180                 185                 190

Val Ile Glu Arg Gly Leu Glu Asp Val Leu Arg Gln Ile Ala Asp Val
            195                 200                 205

Lys Lys Arg Cys Lys Val Tyr Gly Val Gln Ala Pro Asp Pro Thr Ala
210                 215                 220

Gly Gln Val Pro Thr Glu Thr Thr Ile Leu Thr Ser Val Ala Pro Gln
225                 230                 235                 240

Pro Asp Tyr Arg Lys Trp His Phe Leu Thr Ala Cys Glu Ile Ser Ile
                245                 250                 255

Lys Ala Leu Ile His Gln Ala Ser Arg Tyr Ala Glu Leu Ala Lys Glu
                260                 265                 270

Ala Ala Ala Lys Glu Thr Asp Ala Cys Lys Lys Ala Glu Leu Glu Glu
            275                 280                 285

Met Ala Glu Arg Cys Ser Trp Val Pro Ala Lys Pro Ala Arg Thr Phe
290                 295                 300

Lys Glu Ala Val Gln Ala Gln Trp Phe Ile Thr Met Gly Asp Trp Gln
305                 310                 315                 320

Asn Gln Cys Met Thr Val His His Ala Pro Met Arg Phe Pro Gln Tyr
                325                 330                 335

Val Tyr Ala Asn Tyr Lys Lys Asp Ile Glu Glu Gly Arg Ile Thr Asp
                340                 345                 350

Glu Glu Ala Ile Glu Phe Leu Cys Phe Trp Phe Leu Lys Val Asn Thr
            355                 360                 365

Gln Asn Phe Val Met Asn Pro Glu Leu Ala Ile Trp Gln Gln Ser Arg
370                 375                 380

Ile Ala Gln Gln Leu Thr Ile Gly Gly Leu Asp Pro Ala Thr Gly Glu
385                 390                 395                 400

Asp Gly Thr Cys Glu Val Asp Tyr Leu Leu Leu Glu Ala Gln Arg Arg
                405                 410                 415
```

-continued

```
Ala His Cys Pro Glu Pro Gln Leu Ala Val Met Tyr His Asn Lys Leu
            420                 425                 430

Ser Pro Lys Phe Leu Met Ala Cys Val Thr Leu Ile Arg Thr Gly Leu
            435                 440                 445

Gly Gln Pro Ser Phe His Ser Gln Glu Val Ala Met Lys Arg Arg Leu
            450                 455                 460

Leu His Glu Glu Gly Pro Ile Glu Asp Ile Arg Asp Gln Ala Val Ala
465                 470                 475                 480

Gly Cys Val Gln Ser Ile Ile Gly Gly Lys Thr Asp Gly Thr Trp Glu
                485                 490                 495

Ala Arg Phe Asn Met Cys Lys Met Ile Glu Phe Phe Leu Ser Asn Gly
            500                 505                 510

Lys Asp Ile Lys Ser Gly Val Ser Tyr Gly Pro Ala Tyr Gly Asp Pro
            515                 520                 525

Cys Glu Cys Lys Thr Trp Asp Glu Phe Tyr Asp Arg Leu Tyr Lys Tyr
            530                 535                 540

Tyr Glu Tyr Trp Ile Asp Ile Cys Arg Asp Ile Ser Thr Leu Glu Trp
545                 550                 555                 560

Asn Met Glu Arg Asp His Pro Thr Pro Leu Gly Ser Ala Val Thr Tyr
                565                 570                 575

Asp Cys Val Glu Arg Gly Met Asp Met Thr Asp Gly Gly Ala Arg Tyr
            580                 585                 590

Asn Trp Gly Asp Gly Val Cys Leu Ala Gly Ser Val Asp Val Thr Asn
                595                 600                 605

Cys Leu Ala Ala Ile Lys Lys Leu Val Tyr Asp Asp Lys Ser Val Ser
610                 615                 620

Met Asp Thr Met Val Lys Ala Ile His Ala Asp Phe Val Gly Tyr Asp
625                 630                 635                 640

Glu Val Arg Asn Leu Cys Met Lys Ala Pro Lys Tyr Gly Asn Asp Asp
            645                 650                 655

Pro Ala Ala Asp Glu Leu Gly Arg Arg Leu Met Arg Asp Tyr Ala Glu
                660                 665                 670

Ile His Asn Arg Lys Pro Asp Tyr Leu Gly Arg Trp Thr Ile Thr Pro
            675                 680                 685

Ser Ala Tyr Ser Val Thr Ala His Trp Ala Phe Gly Lys Lys Ser Trp
            690                 695                 700

Ala Thr Pro Asp Gly Arg Lys Ala Gly Ala Cys Met Thr Asp Ala Thr
705                 710                 715                 720

Leu Ser Ala Asn Pro Gly Thr Asp Val Lys Gly Pro Thr Ala Leu Ile
                725                 730                 735

Arg Ser Ala Leu Lys Leu Ile Asp Pro Val Val Tyr Gly Ser Thr His
            740                 745                 750

Phe Asn Val Lys Phe His Pro Thr Ala Leu Glu Gly Asp Ala Gly Ala
            755                 760                 765

Gln Lys Phe Leu Gln Leu Ile Lys Thr Tyr Phe Asp Gly Gly Gly Tyr
            770                 775                 780

Gln Ile Gln Phe Asn Cys Val Thr Gln Glu Thr Leu Arg Ala Ala Gln
785                 790                 795                 800

Lys Asp Pro Asp Ser Phe Arg Asp Leu Ile Val Arg Val Ala Gly Phe
                805                 810                 815

Ser Ala Tyr Phe Ile Thr Leu Cys Pro Glu Val Gln Asn Glu Ile Val
            820                 825                 830

Ser Arg Thr Ser Gln Gln Trp
```

835

<210> SEQ ID NO 3
<211> LENGTH: 315
<212> TYPE: PRT
<213> ORGANISM: Unknown
<220> FEATURE:
<223> OTHER INFORMATION: The gene of this polypeptide was cloned from a
      sample selected and obtained from a sewage or lake

<400> SEQUENCE: 3

Met Gly Thr Asn Glu Leu Thr Gly Met Val Phe Asn Ile Gln Gly Tyr
1               5                   10                  15

Ser Val Gln Asp Gly Pro Gly Ile Arg Thr Thr Val Phe Leu Lys Gly
            20                  25                  30

Cys Pro Leu Arg Cys Leu Trp Cys Ser Asn Pro Glu Ser Gln Thr Thr
        35                  40                  45

Pro Lys Asp Val Leu Tyr Ile Arg Ala Lys Cys Val Lys Cys His Arg
    50                  55                  60

Cys Val Asn Ile Cys Lys Asn Gly Ala Ile Ser Tyr Asn Pro Asp Leu
65                  70                  75                  80

Glu Pro Glu Gly Tyr Val Thr Val Asn His Glu Ile Cys Ala Thr Cys
                85                  90                  95

Lys Asp His Val Cys Val Gln Gly Cys Tyr Glu Ser Ala Tyr Glu Asp
            100                 105                 110

Val Gly Thr Pro Met Thr Val Asp Gln Val Met Glu Ile Leu Glu Ala
        115                 120                 125

Asp Gln Pro Phe Phe Val Gln Ser Gly Gly Val Thr Val Ser Gly
    130                 135                 140

Gly Glu Pro Leu Leu Ser His Glu Phe Leu Arg Glu Leu Phe Lys Arg
145                 150                 155                 160

Cys Lys Gln Ser Tyr Ile His Thr Ala Ile Glu Thr Thr Gly Tyr Ala
                165                 170                 175

Pro Trp Asp Asn Phe Lys Ser Val Leu Glu Tyr Thr Asp Leu Ala Leu
            180                 185                 190

Phe Asp Val Lys His Met Asp Pro Val Ile His Lys Gln Leu Thr Gly
        195                 200                 205

Val Ser Asn Glu Leu Ile His Ser Asn Leu Lys Val Phe Ala Glu
    210                 215                 220

Thr Lys Thr Gln Val Val Ile Arg Ile Pro Val Ile Pro Gly Gly Asn
225                 230                 235                 240

Asp Thr Val Glu Asn Met Gln Ala Thr Ala Lys Phe Met Lys Lys Ile
                245                 250                 255

Gly Ala Arg Glu Val Asp Leu Met Pro Tyr His Arg Met Gly Met Gly
            260                 265                 270

Lys Tyr Ala Gly Leu Gly Arg Glu Tyr Pro Met Pro Pro Gly Val Glu
        275                 280                 285

Thr Pro Pro Ala Glu Lys Ile Asn Glu Leu Lys Ala Val Phe Glu Ser
    290                 295                 300

Asn Gly Ile Val Cys His Ile Gly Gly Asn His
305                 310                 315

<210> SEQ ID NO 4
<211> LENGTH: 321
<212> TYPE: PRT
<213> ORGANISM: Unknown
<220> FEATURE:

<223> OTHER INFORMATION: The gene of this polypeptide was cloned from a
      sample selected and obtained from a sewage or lake

<400> SEQUENCE: 4

Met Gly Thr Ser Glu Leu Thr Gly Thr Asn Glu Leu Thr Gly Met Val
1               5                   10                  15

Phe Asn Ile Gln Gly Tyr Ser Ile Gln Asp Gly Pro Gly Ile Arg Thr
            20                  25                  30

Thr Ile Phe Leu Lys Gly Cys Pro Leu Arg Cys Leu Trp Cys Ser Asn
        35                  40                  45

Pro Glu Ser Gln Thr Ser Pro Arg Asp Val Leu Asn Ile Arg Ala Lys
    50                  55                  60

Cys Gln Lys Cys His Arg Cys Val Asp Leu Cys Thr Asn Gly Ala Ile
65                  70                  75                  80

Ser Tyr Asn Pro Glu Leu Glu Pro Glu Gly Tyr Val Thr Ile Asn His
                85                  90                  95

Glu Ile Cys Gly Thr Cys Lys Asp His Leu Cys Val Lys Gly Cys Phe
            100                 105                 110

His Asn Ala Tyr Glu Asp Ala Gly Asn Pro Met Thr Val Ser Glu Val
        115                 120                 125

Met Glu Ile Leu Glu Ala Asp Gln Pro Phe Phe Val Gln Ser Gly Gly
    130                 135                 140

Gly Val Thr Val Ser Gly Gly Glu Pro Leu Val His His Gln Phe Leu
145                 150                 155                 160

Arg Glu Leu Phe Arg Arg Cys Lys Gln Ser Phe Ile His Thr Ala Ile
                165                 170                 175

Glu Thr Thr Gly Tyr Ala Pro Trp Asp Asn Phe Lys Ser Val Leu Glu
            180                 185                 190

Tyr Thr Asp Leu Ala Leu Phe Asp Val Lys His Met Asp Pro Ile Arg
        195                 200                 205

His Lys Glu Leu Thr Gly Val Ser Asn Glu Leu Ile Leu Lys Asn Leu
    210                 215                 220

Glu Lys Val Phe Ala Glu Thr Arg Thr Gln Val Val Arg Ile Pro
225                 230                 235                 240

Val Ile Pro Glu Gly Asn Asp Thr Val Glu Asn Met Gln Ala Thr Ala
                245                 250                 255

Gln Phe Met Lys Lys Ile Gly Ala Arg Glu Val Asp Leu Met Pro Tyr
            260                 265                 270

His Arg Met Gly Thr Gly Lys Tyr Ala Gly Leu Gly Arg Glu Tyr Pro
        275                 280                 285

Leu Pro Met Ser Leu Glu Thr Pro Pro Val Glu Lys Ile Lys Glu Leu
    290                 295                 300

Lys Gly Val Phe Glu Ser Asn Gly Ile Val Cys His Ile Gly Gly Asn
305                 310                 315                 320

His

<210> SEQ ID NO 5
<211> LENGTH: 23
<212> TYPE: PRT
<213> ORGANISM: Artificial Sequence
<220> FEATURE:
<223> OTHER INFORMATION: Sequence identified as conserved for toluene
      synthesis
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(16)
<223> OTHER INFORMATION: Xaa can be any naturally occurring amino acid
<220> FEATURE:
<221> NAME/KEY: misc_feature
<222> LOCATION: (18)..(22)
<223> OTHER INFORMATION: Xaa can be any naturally occurring amino acid

<400> SEQUENCE: 5

Arg Val Xaa Gly Xaa Xaa Xaa Xaa Xaa Xaa Xaa Xaa Xaa Xaa Xaa
1               5                   10                  15

Gln Xaa Xaa Xaa Xaa Xaa Arg
            20

<210> SEQ ID NO 6
<211> LENGTH: 23
<212> TYPE: PRT
<213> ORGANISM: Artificial Sequence
<220> FEATURE:
<223> OTHER INFORMATION: Sequence identified as conserved for toluene
      synthesis
<220> FEATURE:
<221> NAME/KEY: misc_feature
<222> LOCATION: (6)..(11)
<223> OTHER INFORMATION: Xaa can be any naturally occurring amino acid
<220> FEATURE:
<221> NAME/KEY: misc_feature
<222> LOCATION: (13)..(16)
<223> OTHER INFORMATION: Xaa can be any naturally occurring amino acid
<220> FEATURE:
<221> NAME/KEY: misc_feature
<222> LOCATION: (18)..(19)
<223> OTHER INFORMATION: Xaa can be any naturally occurring amino acid
<220> FEATURE:
<221> NAME/KEY: misc_feature
<222> LOCATION: (21)..(22)
<223> OTHER INFORMATION: Xaa can be any naturally occurring amino acid

<400> SEQUENCE: 6

Arg Val Ala Gly Phe Xaa Xaa Xaa Xaa Xaa Xaa Leu Xaa Xaa Xaa Xaa
1               5                   10                  15

Gln Xaa Xaa Ile Xaa Xaa Arg
            20

<210> SEQ ID NO 7
<211> LENGTH: 23
<212> TYPE: PRT
<213> ORGANISM: Artificial Sequence
<220> FEATURE:
<223> OTHER INFORMATION: Sequence identified as conserved for toluene
      synthesis
<220> FEATURE:
<221> NAME/KEY: misc_feature
<222> LOCATION: (18)..(18)
<223> OTHER INFORMATION: Xaa can be any naturally occurring amino acid

<400> SEQUENCE: 7

Arg Val Ala Gly Phe Ser Ala Tyr Phe Ile Thr Leu Cys Pro Glu Val
1               5                   10                  15

Gln Xaa Glu Ile Val Ser Arg
            20

<210> SEQ ID NO 8
<211> LENGTH: 10
<212> TYPE: PRT
<213> ORGANISM: Artificial Sequence
<220> FEATURE:
<223> OTHER INFORMATION: Sequence identified as conserved for toluene
      synthesis

```
-continued

<220> FEATURE:
<221> NAME/KEY: misc_feature
<222> LOCATION: (4)..(9)
<223> OTHER INFORMATION: Xaa can be any naturally occurring amino acid

<400> SEQUENCE: 8

Gly Cys Val Xaa Xaa Xaa Xaa Xaa Xaa Gly
1               5                   10

<210> SEQ ID NO 9
<211> LENGTH: 10
<212> TYPE: PRT
<213> ORGANISM: Unknown
<220> FEATURE:
<223> OTHER INFORMATION: The gene of this polypeptide was cloned from a
      sample selected and obtained from a sewage or lake

<400> SEQUENCE: 9

Gly Cys Val Gln Gln Ser Ile Ile Gly Gly
1               5                   10

<210> SEQ ID NO 10
<211> LENGTH: 8
<212> TYPE: PRT
<213> ORGANISM: Artificial Sequence
<220> FEATURE:
<223> OTHER INFORMATION: Sequence identified as conserved for toluene
      synthesis
<220> FEATURE:
<221> NAME/KEY: misc_feature
<222> LOCATION: (2)..(4)
<223> OTHER INFORMATION: Xaa can be any naturally occurring amino acid
<220> FEATURE:
<221> NAME/KEY: misc_feature
<222> LOCATION: (6)..(7)
<223> OTHER INFORMATION: Xaa can be any naturally occurring amino acid

<400> SEQUENCE: 10

Cys Xaa Xaa Xaa Cys Xaa Xaa Cys
1               5

<210> SEQ ID NO 11
<211> LENGTH: 10
<212> TYPE: PRT
<213> ORGANISM: Artificial Sequence
<220> FEATURE:
<223> OTHER INFORMATION: Sequence identified as conserved for toluene
      synthesis
<220> FEATURE:
<221> NAME/KEY: misc_feature
<222> LOCATION: (2)..(4)
<223> OTHER INFORMATION: Xaa can be any naturally occurring amino acid
<220> FEATURE:
<221> NAME/KEY: misc_feature
<222> LOCATION: (6)..(7)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid

<400> SEQUENCE: 11

Cys Xaa Xaa Xaa Cys Xaa Xaa Cys Xaa Asn
1               5                   10

<210> SEQ ID NO 12
<211> LENGTH: 8
<212> TYPE: PRT
<213> ORGANISM: Unknown
<220> FEATURE:
<223> OTHER INFORMATION: The gene of this polypeptide was cloned from a
``` sample selected and obtained from a sewage or lake

<400> SEQUENCE: 12

Cys Pro Leu Arg Cys Leu Trp Cys
1               5

<210> SEQ ID NO 13
<211> LENGTH: 20
<212> TYPE: PRT
<213> ORGANISM: Artificial Sequence
<220> FEATURE:
<223> OTHER INFORMATION: Sequence identified as conserved for toluene
      synthesis
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(6)
<223> OTHER INFORMATION: Xaa can be any naturally occurring amino acid
<220> FEATURE:
<221> NAME/KEY: misc_feature
<222> LOCATION: (8)..(9)
<223> OTHER INFORMATION: Xaa can be any naturally occurring amino acid
<220> FEATURE:
<221> NAME/KEY: misc_feature
<222> LOCATION: (12)..(14)
<223> OTHER INFORMATION: Xaa can be any naturally occurring amino acid
<220> FEATURE:
<221> NAME/KEY: misc_feature
<222> LOCATION: (16)..(17)
<223> OTHER INFORMATION: Xaa can be any naturally occurring amino acid
<220> FEATURE:
<221> NAME/KEY: misc_feature
<222> LOCATION: (19)..(19)
<223> OTHER INFORMATION: Xaa can be any naturally occurring amino acid

<400> SEQUENCE: 13

Gly Xaa Arg Xaa Xaa Xaa Phe Xaa Xaa Gly Cys Xaa Xaa Xaa Cys Xaa
1               5                   10                  15

Xaa Cys Xaa Asn
            20

<210> SEQ ID NO 14
<211> LENGTH: 16
<212> TYPE: PRT
<213> ORGANISM: Unknown
<220> FEATURE:
<223> OTHER INFORMATION: The gene of this polypeptide was cloned from a
      sample selected and obtained from a sewage or lake

<400> SEQUENCE: 14

Phe Leu Lys Gly Cys Pro Leu Arg Cys Leu Trp Cys Ser Asn Pro Glu
1               5                   10                  15

<210> SEQ ID NO 15
<211> LENGTH: 760
<212> TYPE: PRT
<213> ORGANISM: Escherichia coli

<400> SEQUENCE: 15

Met Ser Glu Leu Asn Glu Lys Leu Ala Thr Ala Trp Glu Gly Phe Thr
1               5                   10                  15

Lys Gly Asp Trp Gln Asn Glu Val Asn Val Arg Asp Phe Ile Gln Lys
                20                  25                  30

Asn Tyr Thr Pro Tyr Glu Gly Asp Glu Ser Phe Leu Ala Gly Ala Thr
            35                  40                  45

-continued

Glu Ala Thr Thr Thr Leu Trp Asp Lys Val Met Glu Gly Val Lys Leu
 50                 55                  60

Glu Asn Arg Thr His Ala Pro Val Asp Phe Asp Thr Ala Val Ala Ser
 65                  70                  75                  80

Thr Ile Thr Ser His Asp Ala Gly Tyr Ile Asn Lys Gln Leu Glu Lys
                 85                  90                  95

Ile Val Gly Leu Gln Thr Glu Ala Pro Leu Lys Arg Ala Leu Ile Pro
             100                 105                 110

Phe Gly Gly Ile Lys Met Ile Glu Gly Ser Cys Lys Ala Tyr Asn Arg
             115                 120                 125

Glu Leu Asp Pro Met Ile Lys Lys Ile Phe Thr Glu Tyr Arg Lys Thr
 130                 135                 140

His Asn Gln Gly Val Phe Asp Val Tyr Thr Pro Asp Ile Leu Arg Cys
145                  150                 155                 160

Arg Lys Ser Gly Val Leu Thr Gly Leu Pro Asp Ala Tyr Gly Arg Gly
                165                 170                 175

Arg Ile Ile Gly Asp Tyr Arg Arg Val Ala Leu Tyr Gly Ile Asp Tyr
             180                 185                 190

Leu Met Lys Asp Lys Leu Ala Gln Phe Thr Ser Leu Gln Ala Asp Leu
        195                 200                 205

Glu Asn Gly Val Asn Leu Glu Gln Thr Ile Arg Leu Arg Glu Glu Ile
210                 215                 220

Ala Glu Gln His Arg Ala Leu Gly Gln Met Lys Glu Met Ala Ala Lys
225                 230                 235                 240

Tyr Gly Tyr Asp Ile Ser Gly Pro Ala Thr Asn Ala Gln Glu Ala Ile
                245                 250                 255

Gln Trp Thr Tyr Phe Gly Tyr Leu Ala Ala Val Lys Ser Gln Asn Gly
            260                 265                 270

Ala Ala Met Ser Phe Gly Arg Thr Ser Thr Phe Leu Asp Val Tyr Ile
        275                 280                 285

Glu Arg Asp Leu Lys Ala Gly Lys Ile Thr Glu Gln Glu Ala Gln Glu
290                 295                 300

Met Val Asp His Leu Val Met Lys Leu Arg Met Val Arg Phe Leu Arg
305                 310                 315                 320

Thr Pro Glu Tyr Asp Glu Leu Phe Ser Gly Asp Pro Ile Trp Ala Thr
                325                 330                 335

Glu Ser Ile Gly Gly Met Gly Leu Asp Gly Arg Thr Leu Val Thr Lys
            340                 345                 350

Asn Ser Phe Arg Phe Leu Asn Thr Leu Tyr Thr Met Gly Pro Ser Pro
        355                 360                 365

Glu Pro Asn Met Thr Ile Leu Trp Ser Glu Lys Leu Pro Leu Asn Phe
370                 375                 380

Lys Lys Phe Ala Ala Lys Val Ser Ile Asp Thr Ser Ser Leu Gln Tyr
385                 390                 395                 400

Glu Asn Asp Asp Leu Met Arg Pro Asp Phe Asn Asn Asp Asp Tyr Ala
                405                 410                 415

Ile Ala Cys Cys Val Ser Pro Met Ile Val Gly Lys Gln Met Gln Phe
            420                 425                 430

Phe Gly Ala Arg Ala Asn Leu Ala Lys Thr Met Leu Tyr Ala Ile Asn
        435                 440                 445

Gly Gly Val Asp Glu Lys Leu Lys Met Gln Val Gly Pro Lys Ser Glu
450                 455                 460

Pro Ile Lys Gly Asp Val Leu Asn Tyr Asp Glu Val Met Glu Arg Met

```
            465                 470                 475                 480

Asp His Phe Met Asp Trp Leu Ala Lys Gln Tyr Ile Thr Ala Leu Asn
                    485                 490                 495

Ile Ile His Tyr Met His Asp Lys Tyr Ser Tyr Glu Ala Ser Leu Met
                    500                 505                 510

Ala Leu His Asp Arg Asp Val Ile Arg Thr Met Ala Cys Gly Ile Ala
                    515                 520                 525

Gly Leu Ser Val Ala Ala Asp Ser Leu Ser Ala Ile Lys Tyr Ala Lys
                    530                 535                 540

Val Lys Pro Ile Arg Asp Glu Asp Gly Leu Ala Ile Asp Phe Glu Ile
    545                 550                 555                 560

Glu Gly Glu Tyr Pro Gln Phe Gly Asn Asn Asp Pro Arg Val Asp Asp
                    565                 570                 575

Leu Ala Val Asp Leu Val Glu Arg Phe Met Lys Ile Gln Lys Leu
                    580                 585                 590

His Thr Tyr Arg Asp Ala Ile Pro Thr Gln Ser Val Leu Thr Ile Thr
                    595                 600                 605

Ser Asn Val Val Tyr Gly Lys Lys Thr Gly Asn Thr Pro Asp Gly Arg
                    610                 615                 620

Arg Ala Gly Ala Pro Phe Gly Pro Gly Ala Asn Pro Met His Gly Arg
    625                 630                 635                 640

Asp Gln Lys Gly Ala Val Ala Ser Leu Thr Ser Val Ala Lys Leu Pro
                    645                 650                 655

Phe Ala Tyr Ala Lys Asp Gly Ile Ser Tyr Thr Phe Ser Ile Val Pro
                    660                 665                 670

Asn Ala Leu Gly Lys Asp Asp Glu Val Arg Lys Thr Asn Leu Ala Gly
                    675                 680                 685

Leu Met Asp Gly Tyr Phe His His Glu Ala Ser Ile Glu Gly Gly Gln
                    690                 695                 700

His Leu Asn Val Asn Val Met Asn Arg Glu Met Leu Leu Asp Ala Met
    705                 710                 715                 720

Glu Asn Pro Glu Lys Tyr Pro Gln Leu Thr Ile Arg Val Ser Gly Tyr
                    725                 730                 735

Ala Val Arg Phe Asn Ser Leu Thr Lys Glu Gln Gln Gln Asp Val Ile
                    740                 745                 750

Thr Arg Thr Phe Thr Gln Ser Met
                    755                 760

<210> SEQ ID NO 16
<211> LENGTH: 246
<212> TYPE: PRT
<213> ORGANISM: Escherichia coli

<400> SEQUENCE: 16

Met Ser Val Ile Gly Arg Ile His Ser Phe Glu Ser Cys Gly Thr Val
1               5                   10                  15

Asp Gly Pro Gly Ile Arg Phe Ile Thr Phe Phe Gln Gly Cys Leu Met
                20                  25                  30

Arg Cys Leu Tyr Cys His Asn Arg Asp Thr Trp Asp Thr His Gly Gly
            35                  40                  45

Lys Glu Val Thr Val Glu Asp Leu Met Lys Glu Val Val Thr Tyr Arg
        50                  55                  60

His Phe Met Asn Ala Ser Gly Gly Gly Val Thr Ala Ser Gly Gly Glu
65                  70                  75                  80
```

```
Ala Ile Leu Gln Ala Glu Phe Val Arg Asp Trp Phe Arg Ala Cys Lys
             85                  90                  95

Lys Glu Gly Ile His Thr Cys Leu Asp Thr Asn Gly Phe Val Arg Arg
        100                 105                 110

Tyr Asp Pro Val Ile Asp Glu Leu Leu Glu Val Thr Asp Leu Val Met
        115                 120                 125

Leu Asp Leu Lys Gln Met Asn Asp Glu Ile His Gln Asn Leu Val Gly
    130                 135                 140

Val Ser Asn His Arg Thr Leu Glu Phe Ala Lys Tyr Leu Ala Asn Lys
145                 150                 155                 160

Asn Val Lys Val Trp Ile Arg Tyr Val Val Pro Gly Trp Ser Asp
                165                 170                 175

Asp Asp Asp Ser Ala His Arg Leu Gly Glu Phe Thr Arg Asp Met Gly
            180                 185                 190

Asn Val Glu Lys Ile Glu Leu Leu Pro Tyr His Glu Leu Gly Lys His
        195                 200                 205

Lys Trp Val Ala Met Gly Glu Glu Tyr Lys Leu Asp Gly Val Lys Pro
    210                 215                 220

Pro Lys Lys Glu Thr Met Glu Arg Val Lys Gly Ile Leu Glu Gln Tyr
225                 230                 235                 240

Gly His Lys Val Met Phe
                245

<210> SEQ ID NO 17
<211> LENGTH: 897
<212> TYPE: PRT
<213> ORGANISM: Clostridium scatologenes

<400> SEQUENCE: 17

Met Asn Val Lys Glu Thr Lys Leu Glu Asp Val Leu Lys Ser Arg Gly
1               5                   10                  15

Ile Asp Met Lys Asp Ala Tyr Asn Ile Ser Glu Ala Asp Ile Pro Glu
            20                  25                  30

Ala Lys Glu Ser Thr Gln Lys Leu Met Asp Ile Tyr Tyr Thr Leu Lys
        35                  40                  45

Val Thr Ala Asp Met Glu Ala Ala Tyr Trp Tyr Asn Arg Thr Trp Trp
    50                  55                  60

Glu Asn Asp Gly Glu Val Ile Glu Val Arg Arg Ala Lys Ala Val Ala
65                  70                  75                  80

Ala Ser Leu Ser His Met Thr Pro Thr Ile Leu Pro Tyr Glu Lys Leu
                85                  90                  95

Val Met Asn Lys Thr Lys Asn Val Arg Gly Ala Phe Pro Phe Pro Trp
            100                 105                 110

Val Cys Ala Ser Phe Phe Asn Ala Gln Ala Glu Ala Leu Met Asn Glu
        115                 120                 125

Val Asp Ala Pro Ala Glu Asn Glu Ala Asp Ser Val Ser Val Val Gly
    130                 135                 140

Ala Gly Gly Gly Asn Val Thr Glu Ser Tyr Gly Asn Val Ile Ser Ile
145                 150                 155                 160

Ala Lys Lys Phe Gly Met Arg Lys Glu Ile Pro Val Leu Val Lys
                165                 170                 175

Thr Ser Lys Pro Trp Glu Gly Ile Ser Val Glu Glu Leu Ser Asn Lys
            180                 185                 190

Tyr Ser Lys Met Thr Pro Gly Tyr Asp Gln Phe Lys Asn Ile Met Glu
        195                 200                 205
```

-continued

```
Ser Val Ile Cys Met Phe Asp Ser Phe Ala Ile Pro Gln Gly Arg Glu
    210                 215                 220

Val Ile Asn Tyr Tyr Met Pro Leu Gln Tyr Gly Phe Asp Gly Ile Ile
225                 230                 235                 240

Lys Leu Cys Asp Glu Lys Ile Ala Glu Val Met Gly Glu Ala Gly Asp
                245                 250                 255

Asp Gly Asp Phe Gly Met Ser Arg Gly Tyr Tyr Ala Ala Met Lys
                260                 265                 270

Glu Ile Thr Lys Gly Leu Ser Ala Trp Cys Glu Asn Tyr Ser Lys Arg
                275                 280                 285

Ala Lys Tyr Leu Ala Ser Ile Glu Thr Asp Ser Glu Ile Lys Ala Asn
    290                 295                 300

Tyr Glu Lys Ile Glu Glu Val Met Gly Asn Ile Ala His Lys Lys Pro
305                 310                 315                 320

Ala Asn Phe Trp Glu Ala Ile Gln Met Thr Leu Cys Cys His Phe Gly
                325                 330                 335

Val Val Asn Glu Asp Pro Gln Ser Gly Leu Ser Ile Gly Arg Leu Gly
                340                 345                 350

Gln Val Leu Gln Pro Phe Tyr Glu Lys Asp Val Glu Asp Gly Ile Met
    355                 360                 365

Thr Asp Glu Glu Val Ile Glu Leu Leu Glu Leu Tyr Arg Ile Lys Ile
370                 375                 380

Thr Cys Ile Glu Cys Phe Ala Ser Ala Gly Val Ser Gly Gly Val Leu
385                 390                 395                 400

Ser Gly Asn Thr Phe Asn Asn Leu Ser Leu Gly Gly Gln Asn Tyr Asp
                405                 410                 415

Gly Leu Ser Ala Val Thr Pro Leu Glu Tyr Leu Ile Val Glu Ala Gly
                420                 425                 430

Met Arg Asn Gln Thr Pro Gln Pro Thr Leu Ser Val Leu Tyr Asp Glu
                435                 440                 445

Lys Thr Pro Glu Asp Phe Leu Met Lys Ala Ala Ser Cys Thr Lys Leu
    450                 455                 460

Gly Leu Gly Tyr Pro Ala Trp Met Asn Asn Gln Thr Gly Met Asn Phe
465                 470                 475                 480

Met Met Arg Asn Tyr Gly Pro Glu Gly Met Asp Leu His Asp Ala Arg
                485                 490                 495

Ala Trp Cys Leu Gly Gly Cys Leu Glu Ser Ala Pro Gly Cys Phe Leu
                500                 505                 510

Pro Leu Glu Tyr Asn Gly Lys Val Thr Met Ile Pro Gly Ala Ser
    515                 520                 525

Pro Thr Cys Gly Thr Gly Val His Phe Ile Gly Met Pro Lys Val Leu
530                 535                 540

Glu Leu Val Leu Thr Asn Gly Leu Asp Lys Arg Thr Gly Lys Gln Val
545                 550                 555                 560

Tyr Pro Pro His Asn Lys Lys Leu Asp Ser Tyr Glu Thr Met Val Asn
                565                 570                 575

Gln Trp Lys Glu Tyr Met Glu Leu Thr Thr Asp Val Val Asn Arg Cys
                580                 585                 590

Asn Asn Ile Gln Met Asp Ile Trp Arg Lys Tyr Asn Met Pro Ala Val
                595                 600                 605

Asn Ser Leu Leu Lys Pro Asp Cys Phe Lys Lys Gly Lys His Ile Gly
    610                 615                 620
```

```
Thr Met Gly Ala Arg Tyr Asn Ser Cys Ile Asn Phe Glu Ser Cys Gly
625                 630                 635                 640

Thr Ile Thr Phe Val Asn Ser Leu Ser Ser Ile Lys Lys Asn Val Phe
            645                 650                 655

Asp Asp Ser Lys Phe Thr Ile Glu Glu Met Thr Asp Ala Met Leu Asn
        660                 665                 670

Asn Phe Gly Phe Lys Thr Ala Tyr Glu Thr Glu Val Phe Ser Pro Asp
    675                 680                 685

Phe Arg Glu Ser Thr Asp Lys Ser Thr Lys Tyr Glu Lys Ile Phe Ala
690                 695                 700

Ala Cys Val Asn Ala Pro Lys Tyr Gly Asn Ala Asp Lys Tyr Ala Asp
705                 710                 715                 720

Glu Ile Phe Lys Ala Tyr His Tyr Tyr Ile Tyr Asp Met Thr His Lys
            725                 730                 735

Phe Arg Ser Tyr Tyr Gly Lys Pro Leu Tyr Leu Cys Gln Ile Ser Val
        740                 745                 750

Ser Thr His Gly Pro Gln Gly Phe Val Thr Leu Ala Thr Ala Asp Gly
    755                 760                 765

Arg Leu Ala Gly Thr Thr Tyr Ser Asp Gly Ser Val Ser Ala Ala Ala
770                 775                 780

Gly Thr Asp Lys Asn Gly Ile Tyr Ala Ile Phe Glu Ser Ala Thr Val
785                 790                 795                 800

Tyr Asp His Ser Met His Gln Asn Ala Gln Met Asn Leu Lys Leu His
            805                 810                 815

Pro Thr Ala Val Lys Gly Ile Asn Gly Thr Arg Lys Leu Leu Asp Leu
        820                 825                 830

Val Arg Ala Tyr Met Arg Lys Gly Gly Phe His Val Gln Phe Asn Val
835                 840                 845

Val Asp Ser Lys Thr Leu Arg Asp Ala Gln Leu Thr Pro Glu Lys Tyr
850                 855                 860

Arg Glu Leu Met Val Arg Val Ala Gly Phe Thr Gln Tyr Trp Cys Glu
865                 870                 875                 880

Ile Gly Lys Pro Ile Gln Asp Glu Val Ile Tyr Arg Thr Glu Tyr Asp
            885                 890                 895

Lys
```

```
<210> SEQ ID NO 18
<211> LENGTH: 312
<212> TYPE: PRT
<213> ORGANISM: Clostridium scatologenes

<400> SEQUENCE: 18

Met Lys Glu Lys Gly Leu Ile Phe Asp Ile Gln Ser Phe Ser Val His
1               5                   10                  15

Asp Gly Pro Gly Cys Arg Thr Ser Val Phe Phe Ile Gly Cys Pro Leu
            20                  25                  30

Gln Cys Lys Trp Cys Ala Asn Pro Glu Ser Trp Thr Lys Lys His
        35                  40                  45

Ile Met Val Ala Glu Asn Val Cys Lys Trp Lys Asn Gly Cys Arg Ser
50                  55                  60

Cys Ile Asn Ala Cys Ser His Asp Ser Ile Lys Phe Ser Glu Asp Gly
65                  70                  75                  80

Lys Leu Lys Ile Ser Trp Asp Thr Cys Glu Lys Cys Glu Thr Phe Asp
            85                  90                  95
```

Cys Val Asn Met Cys Pro Asn Asn Ala Leu Lys Gln Cys Val Lys Glu
                100                 105                 110

Tyr Thr Val Asp Glu Leu Met Thr Ile Leu Lys Arg Asp Phe Asn Asn
            115                 120                 125

Trp Gly Ser Asp Gly Val Thr Phe Thr Gly Gly Asp Pro Leu Met
        130                 135                 140

His His Glu Phe Leu Val Glu Val Leu Lys Lys Cys Tyr Asp Ser Gln
145                 150                 155                 160

Ile His Lys Ala Ile Glu Thr Ser Gly Tyr Ala Lys Gln Glu Val Phe
                165                 170                 175

Leu Glu Val Leu Lys Tyr Ile Asp Phe Ala Phe Ile Asp Val Lys Asn
            180                 185                 190

Met Asp Arg Glu Lys His Lys Gln Gly Thr Gly Val Tyr Asn Asp Leu
        195                 200                 205

Ile Leu Ser Asn Ile Glu Ala Leu Lys Lys Ser Asn Trp Asn Gly Arg
210                 215                 220

Leu Val Leu Arg Gln Pro Thr Ile Ala Gly Tyr Asn Asp Ser Asp Glu
225                 230                 235                 240

Asn Ala Tyr Lys Leu Ile Glu Phe Met Asn Lys Asn Ser Leu Tyr Glu
                245                 250                 255

Ile Asn Leu Leu Lys Phe His Arg Leu Gly Glu Thr Lys Trp Asn Gln
            260                 265                 270

Leu Gly Lys Glu Tyr Glu Tyr Ser Lys Tyr Gly Asp Met Thr Asn Glu
        275                 280                 285

Lys Met Glu His Leu Gln Gln Leu Tyr Leu Asp Asn Asn Ile Ala Cys
290                 295                 300

Tyr Ile Gly Asp Asn Thr Pro Phe
305                 310

<210> SEQ ID NO 19
<211> LENGTH: 864
<212> TYPE: PRT
<213> ORGANISM: Thauera aromatica

<400> SEQUENCE: 19

Met Asn Asp Ile Val Ser Ala Lys Val Leu Glu Tyr Lys Gly Lys Lys
1               5                   10                  15

Leu Asn Phe Thr Pro Glu Asp Pro Ala Glu Glu Thr Ile Pro Ala Asp
            20                  25                  30

Glu Leu His Glu His Leu Gln Lys Pro Ser Thr Ala Arg Thr Lys Arg
        35                  40                  45

Leu Lys Glu Arg Cys Arg Trp Lys His Ala Ser Ala Gly Glu Phe Ile
50                  55                  60

Glu Lys Ser Val Thr Ala Gly Ile Glu Arg Met Arg Tyr Leu Thr Glu
65                  70                  75                  80

Ala His Lys Ala Ser Glu Gly Lys Pro Glu Ala Ile Arg Arg Ala Leu
                85                  90                  95

Gly Leu Ala Asn Val Leu Asn Lys Ser Thr Leu Val Leu Gln Glu Asp
            100                 105                 110

Glu Phe Ile Val Gly Tyr His Ala Glu Asp Pro Asn Met Phe Pro Leu
        115                 120                 125

Tyr Pro Glu Leu Ser His Met Ala Val Gln Asp Tyr Leu Arg Ser Asp
130                 135                 140

Tyr Ser Pro Gln Pro Ala Asp Glu Ala Ala Ile Asn Glu Tyr Trp
145                 150                 155                 160

```
Lys Pro His Ser Leu Gln Ser Lys Cys Gln Pro Tyr Phe Asp Pro Ala
                165                 170                 175

Asp Leu Gly Arg Met Tyr Gln Val Ser Ser Met Glu Ala Pro Ser Phe
            180                 185                 190

Ala Ser Gly Tyr Asn Ser Ile Val Pro Pro Tyr Glu Thr Val Leu Glu
        195                 200                 205

Asp Gly Leu Leu Ala Arg Ile Lys Leu Ala Glu Lys His Ile Ala Glu
    210                 215                 220

Ala Gln Ala Asp Met Ser Thr Phe Pro Trp Asn Gly Thr Lys Gly Leu
225                 230                 235                 240

Asp Asn Ile Ala Lys Ile Asp Asn Trp Lys Ala Met Val Ile Ala Cys
                245                 250                 255

Lys Ala Val Ile Ser Trp Ala Arg Arg Gln Gly Arg Leu Cys Lys Ile
            260                 265                 270

Val Ala Glu Asn Phe Glu Thr Asp Pro Lys Arg Gln Ala Glu Leu Leu
        275                 280                 285

Glu Ile Ala Asp Ile Cys Gln Arg Ile Pro Ala Glu Pro Cys Lys Gly
    290                 295                 300

Leu Lys Asp Ala Met Gln Ala Lys Phe Phe Thr Phe Leu Ile Cys His
305                 310                 315                 320

Ala Ile Glu Arg Tyr Ala Ser Gly Tyr Ala Gln Lys Glu Asp Thr Leu
                325                 330                 335

Leu Trp Pro Tyr Tyr Lys Ala Ser Val Val Asp Lys Lys Phe Gln Pro
            340                 345                 350

Met Ser His Met Asp Ala Val Glu Leu Val Glu Met Glu Arg Leu Lys
        355                 360                 365

Ile Ser Glu His Gly Ala Gly Lys Ser Arg Ala Tyr Arg Glu Ile Phe
    370                 375                 380

Pro Gly Ser Asn Asp Leu Phe Ile Leu Thr Val Gly Gly Thr Asn Ala
385                 390                 395                 400

Lys Gly Glu Asp Ala Cys Asn Asp Met Thr Asp Ala Ile Leu Glu Ala
                405                 410                 415

Ala Lys Arg Ile Arg Thr Ala Glu Pro Ser Ile Val Phe Arg Tyr Ser
            420                 425                 430

Lys Lys Asn Arg Glu Lys Thr Leu Arg Trp Val Phe Glu Cys Ile Arg
        435                 440                 445

Asp Gly Leu Gly Tyr Pro Ser Ile Lys His Asp Glu Ile Gly Thr Glu
    450                 455                 460

Gln Met Lys Glu Tyr Ala Lys Phe Ser Leu Asn Gly Asn Gly Ala Thr
465                 470                 475                 480

Asp Glu Glu Ala His Asn Trp Val Asn Val Leu Cys Met Ser Pro Gly
                485                 490                 495

Ile His Gly Arg Arg Lys Thr Gln Lys Thr Arg Ser Glu Gly Gly Gly
            500                 505                 510

Ser Ile Phe Pro Ala Lys Leu Leu Glu Ile Ser Leu Asn Asp Gly Tyr
        515                 520                 525

Asp Trp Ser Tyr Ala Asp Met Gln Leu Gly Pro Lys Thr Gly Asp Leu
    530                 535                 540

Ser Ser Leu Lys Ser Phe Glu Asp Val Trp Glu Ala Phe Arg Lys Gln
545                 550                 555                 560

Tyr Gln Tyr Ala Ile Asn Leu Cys Ile Ser Thr Lys Asp Val Ser Arg
                565                 570                 575
```

```
Tyr Phe Glu Gln Arg Phe Leu Gln Met Pro Phe Val Ser Ala Ile Asp
                580                 585                 590

Asp Gly Cys Met Glu Leu Gly Met Asp Ala Cys Ala Leu Ser Glu Gln
            595                 600                 605

Pro Asn Gly Trp His Asn Pro Ile Thr Thr Ile Val Ala Ala Asn Ser
        610                 615                 620

Leu Val Ala Ile Lys Lys Leu Val Phe Glu Glu Lys Lys Tyr Thr Leu
625                 630                 635                 640

Glu Gln Leu Ser Gln Ala Leu Lys Ala Asn Trp Glu Gly Phe Glu Glu
                645                 650                 655

Met Arg Val Asp Phe Lys Arg Ala Pro Lys Trp Gly Asn Asp Asp Asp
            660                 665                 670

Tyr Ala Asp Gly Ile Ile Thr Arg Phe Tyr Glu Glu Ile Ile Gly Gly
        675                 680                 685

Glu Met Arg Lys Ile Thr Asn Tyr Ser Gly Gly Pro Val Met Pro Thr
690                 695                 700

Gly Gln Ala Val Gly Leu Tyr Met Glu Val Gly Ser Arg Thr Gly Pro
705                 710                 715                 720

Thr Pro Asp Gly Arg Phe Gly Gly Glu Ala Ala Asp Asp Gly Gly Ile
                725                 730                 735

Ser Pro Tyr Met Gly Thr Asp Lys Lys Gly Pro Thr Ala Val Leu Arg
            740                 745                 750

Ser Val Ser Lys Val Gln Lys Asn Gln Lys Gly Asn Leu Leu Asn Gln
        755                 760                 765

Arg Leu Ser Val Pro Ile Met Arg Ser Lys His Gly Phe Glu Ile Trp
770                 775                 780

Asn Ser Tyr Met Lys Thr Trp His Asp Leu Asn Ile Asp His Val Gln
                785                 790                 795                 800

Phe Asn Val Val Ser Thr Asp Glu Met Arg Ala Ala Gln Arg Glu Pro
            805                 810                 815

Glu Lys His His Asp Leu Ile Val Arg Val Ser Gly Tyr Ser Ala Arg
        820                 825                 830

Phe Val Asp Ile Pro Thr Tyr Gly Gln Asn Thr Ile Ile Ala Arg Gln
835                 840                 845

Glu Gln Asp Phe Ser Ala Ser Asp Leu Glu Phe Leu Asn Val Glu Ile
                850                 855                 860

<210> SEQ ID NO 20
<211> LENGTH: 331
<212> TYPE: PRT
<213> ORGANISM: Thauera aromatica

<400> SEQUENCE: 20

Met Lys Ile Pro Leu Ile Thr Glu Ile Gln Arg Phe Ser Leu Gln Asp
1               5                   10                  15

Gly Pro Gly Ile Arg Thr Thr Ile Phe Leu Lys Gly Cys Pro Leu Arg
                20                  25                  30

Cys Pro Trp Cys His Asn Pro Glu Thr Gln Asp Ala Arg Gln Glu Phe
            35                  40                  45

Tyr Phe Tyr Pro Asp Arg Cys Val Gly Cys Gly Arg Cys Val Ala Val
        50                  55                  60

Cys Pro Ala Glu Thr Ser Arg Leu Val Arg Asn Ser Asp Gly Arg Thr
65                  70                  75                  80

Ile Val Gln Ile Asp Arg Thr Asn Cys Gln Arg Cys Met Arg Cys Val
                85                  90                  95
```

```
Ala Ala Cys Leu Thr Glu Ala Arg Ala Ile Val Gly Gln His Met Ser
            100                 105                 110

Val Asp Glu Ile Leu Arg Glu Ala Leu Ser Asp Ser Ala Phe Tyr Arg
            115                 120                 125

Asn Ser Gly Gly Gly Val Thr Ile Ser Gly Gly Asp Pro Leu Tyr Phe
            130                 135                 140

Pro Asp Phe Thr Arg Gln Leu Ala Ser Glu Leu His Ala Arg Gly Val
145                 150                 155                 160

His Val Ala Ile Glu Thr Ser Cys Phe Pro Lys Gln Gly Lys Val Val
                165                 170                 175

Glu Ser Met Ile Gly Ile Val Asp Leu Phe Ile Val Asp Leu Lys Thr
            180                 185                 190

Leu Asp Ala His Lys His Leu Asp Val Ile Gly Trp Pro Leu Ala Pro
            195                 200                 205

Ile Leu Ala Asn Leu Glu Thr Leu Phe Ala Ala Gly Ala Lys Val Arg
210                 215                 220

Ile His Ile Pro Val Ile Pro Gly Phe Asn Asp Ser His Ala Asp Ile
225                 230                 235                 240

Asp Ala Tyr Ala Glu Tyr Leu Gly Lys His Ala Ala Ile Ser Gly
                245                 250                 255

Ile Asp Leu Leu Asn Phe His Cys Tyr Gly Glu Gly Lys Tyr Thr Phe
            260                 265                 270

Leu Gly Arg Ala Gly Ser Tyr Gln Tyr Ser Gly Val Asp Glu Thr Pro
            275                 280                 285

Ala Glu Lys Ile Val Pro Leu Ala Gln Ala Leu Lys Ala Arg Gly Leu
            290                 295                 300

Ala Val Thr Ile Gly Gly Ile Val Gly Ile Ala Asn Gly Lys Asn Glu
305                 310                 315                 320

Leu Thr Gly Asp Ile Ala Leu Glu Val His His
                325                 330

<210> SEQ ID NO 21
<211> LENGTH: 787
<212> TYPE: PRT
<213> ORGANISM: Clostridium butyricum

<400> SEQUENCE: 21

Met Ile Ser Lys Gly Phe Ser Thr Gln Thr Glu Arg Ile Asn Ile Leu
1               5                   10                  15

Lys Ala Gln Ile Leu Asn Ala Lys Pro Cys Val Glu Ser Glu Arg Ala
            20                  25                  30

Ile Leu Ile Thr Glu Ser Phe Lys Gln Thr Glu Gly Gln Pro Ala Ile
            35                  40                  45

Leu Arg Arg Ala Leu Ala Leu Lys His Ile Leu Glu Asn Ile Pro Ile
50                  55                  60

Thr Ile Arg Asp Gln Glu Leu Ile Val Gly Ser Leu Thr Lys Glu Pro
65                  70                  75                  80

Arg Ser Ser Gln Val Phe Pro Glu Phe Ser Asn Lys Trp Leu Gln Asp
            85                  90                  95

Glu Leu Asp Arg Leu Asn Lys Arg Thr Gly Asp Ala Phe Gln Ile Ser
            100                 105                 110

Glu Glu Ser Lys Glu Lys Leu Lys Asp Val Phe Glu Tyr Trp Asn Gly
            115                 120                 125

Lys Thr Thr Ser Glu Leu Ala Thr Ser Tyr Met Thr Glu Glu Thr Arg
```

```
                130                 135                 140
Glu Ala Val Asn Cys Asp Val Phe Thr Val Gly Asn Tyr Tyr Tyr Asn
145                 150                 155                 160
Gly Val Gly His Val Ser Val Asp Tyr Gly Lys Val Leu Arg Val Gly
                165                 170                 175
Phe Asn Gly Ile Ile Asn Glu Ala Lys Glu Gln Leu Glu Lys Asn Arg
                180                 185                 190
Ser Ile Asp Pro Asp Phe Ile Lys Lys Glu Lys Phe Leu Asn Ser Val
                195                 200                 205
Ile Ile Ser Cys Glu Ala Ala Ile Thr Tyr Val Asn Arg Tyr Ala Lys
                210                 215                 220
Lys Ala Lys Glu Ile Ala Asp Asn Thr Ser Asp Ala Lys Arg Lys Ala
225                 230                 235                 240
Glu Leu Asn Glu Ile Ala Lys Ile Cys Ser Lys Val Ser Gly Glu Gly
                245                 250                 255
Ala Lys Ser Phe Tyr Glu Ala Cys Gln Leu Phe Trp Phe Ile His Ala
                260                 265                 270
Ile Ile Asn Ile Glu Ser Asn Gly His Ser Ile Ser Pro Ala Arg Phe
                275                 280                 285
Asp Gln Tyr Met Tyr Pro Tyr Glu Asn Asp Lys Asn Ile Thr Asp
                290                 295                 300
Lys Phe Ala Gln Glu Leu Ile Asp Cys Ile Trp Ile Lys Leu Asn Asp
305                 310                 315                 320
Ile Asn Lys Val Arg Asp Glu Ile Ser Thr Lys His Phe Gly Gly Tyr
                325                 330                 335
Pro Met Tyr Gln Asn Leu Ile Val Gly Gly Gln Asn Ser Glu Gly Lys
                340                 345                 350
Asp Ala Thr Asn Lys Val Ser Tyr Met Ala Leu Glu Ala Val His
                355                 360                 365
Val Lys Leu Pro Gln Pro Ser Leu Ser Val Arg Ile Trp Asn Lys Thr
                370                 375                 380
Pro Asp Glu Phe Leu Leu Arg Ala Ala Glu Leu Thr Arg Glu Gly Leu
385                 390                 395                 400
Gly Leu Pro Ala Tyr Tyr Asn Asp Glu Val Ile Ile Pro Ala Leu Val
                405                 410                 415
Ser Arg Gly Leu Thr Leu Glu Asp Ala Arg Asp Tyr Gly Ile Ile Gly
                420                 425                 430
Cys Val Glu Pro Gln Lys Pro Gly Lys Thr Glu Gly Trp His Asp Ser
                435                 440                 445
Ala Phe Phe Asn Leu Ala Arg Ile Val Glu Leu Thr Ile Asn Ser Gly
                450                 455                 460
Phe Asp Lys Asn Lys Gln Ile Gly Pro Lys Thr Gln Asn Phe Glu Glu
465                 470                 475                 480
Met Lys Ser Phe Asp Glu Phe Met Lys Ala Tyr Lys Ala Gln Met Glu
                485                 490                 495
Tyr Phe Val Lys His Met Cys Cys Ala Asp Asn Cys Ile Asp Ile Ala
                500                 505                 510
His Ala Glu Arg Ala Pro Leu Pro Phe Leu Ser Ser Met Val Asp Asn
                515                 520                 525
Cys Ile Gly Lys Gly Lys Ser Leu Gln Asp Gly Ala Glu Tyr Asn
                530                 535                 540
Phe Ser Gly Pro Gln Gly Val Gly Val Ala Asn Ile Gly Asp Ser Leu
545                 550                 555                 560
```

```
Val Ala Val Lys Lys Ile Val Phe Asp Glu Asn Lys Ile Thr Pro Ser
            565                 570                 575

Glu Leu Lys Lys Thr Leu Asn Asn Asp Phe Lys Asn Ser Glu Glu Ile
        580                 585                 590

Gln Ala Leu Leu Lys Asn Ala Pro Lys Phe Gly Asn Asp Ile Asp Glu
    595                 600                 605

Val Asp Asn Leu Ala Arg Glu Gly Ala Leu Val Tyr Cys Arg Glu Val
610                 615                 620

Asn Lys Tyr Thr Asn Pro Arg Gly Asn Phe Gln Pro Gly Leu Tyr
625                 630                 635                 640

Pro Ser Ser Ile Asn Val Tyr Phe Gly Ser Leu Thr Gly Ala Thr Pro
                645                 650                 655

Asp Gly Arg Lys Ser Gly Gln Pro Leu Ala Asp Gly Val Ser Pro Ser
            660                 665                 670

Arg Gly Cys Asp Val Ser Gly Pro Thr Ala Ala Cys Asn Ser Val Ser
        675                 680                 685

Lys Leu Asp His Phe Ile Ala Ser Asn Gly Thr Leu Phe Asn Gln Lys
    690                 695                 700

Phe His Pro Ser Ala Leu Lys Gly Asp Asn Gly Leu Met Asn Leu Ser
705                 710                 715                 720

Ser Leu Ile Arg Ser Tyr Phe Asp Gln Lys Gly Phe His Val Gln Phe
                725                 730                 735

Asn Val Ile Asp Lys Lys Ile Leu Leu Ala Ala Gln Lys Asn Pro Glu
            740                 745                 750

Lys Tyr Gln Asp Leu Ile Val Arg Val Ala Gly Tyr Ser Ala Gln Phe
        755                 760                 765

Ile Ser Leu Asp Lys Ser Ile Gln Asn Asp Ile Ile Ala Arg Thr Glu
    770                 775                 780

His Val Met
785

<210> SEQ ID NO 22
<211> LENGTH: 304
<212> TYPE: PRT
<213> ORGANISM: Clostridium butyricum

<400> SEQUENCE: 22

Met Ser Lys Glu Ile Lys Gly Val Leu Phe Asn Ile Gln Lys Phe Ser
1               5                   10                  15

Leu His Asp Gly Pro Gly Ile Arg Thr Ile Val Phe Phe Lys Gly Cys
            20                  25                  30

Ser Met Ser Cys Leu Trp Cys Ser Asn Pro Glu Ser Gln Asp Ile Lys
        35                  40                  45

Pro Gln Val Met Phe Asn Lys Asn Leu Cys Thr Lys Cys Gly Arg Cys
    50                  55                  60

Lys Ser Gln Cys Lys Ser Ala Ala Ile Asp Met Asn Ser Glu Tyr Arg
65                  70                  75                  80

Ile Asp Lys Ser Lys Cys Thr Glu Cys Thr Lys Cys Val Asp Asn Cys
                85                  90                  95

Leu Ser Gly Ala Leu Val Ile Glu Gly Arg Asn Tyr Ser Val Glu Asp
            100                 105                 110

Val Ile Lys Glu Leu Lys Lys Asp Ser Val Gln Tyr Arg Arg Ser Asn
        115                 120                 125

Gly Gly Ile Thr Leu Ser Gly Gly Glu Val Leu Leu Gln Pro Asp Phe
```

```
            130                 135                 140
Ala Val Glu Leu Leu Lys Glu Cys Lys Ser Tyr Gly Trp His Thr Ala
145                 150                 155                 160

Ile Glu Thr Ala Met Tyr Val Asn Ser Glu Ser Val Lys Lys Val Ile
                165                 170                 175

Pro Tyr Ile Asp Leu Ala Met Ile Asp Ile Lys Ser Met Asn Asp Glu
            180                 185                 190

Ile His Arg Lys Phe Thr Gly Val Ser Asn Glu Ile Ile Leu Gln Asn
            195                 200                 205

Ile Lys Leu Ser Asp Glu Leu Ala Lys Glu Ile Ile Arg Ile Pro
        210                 215                 220

Val Ile Glu Gly Phe Asn Ala Asp Leu Gln Ser Ile Gly Ala Ile Ala
225                 230                 235                 240

Gln Phe Ser Lys Ser Leu Thr Asn Leu Lys Arg Ile Asp Leu Leu Pro
                245                 250                 255

Tyr His Asn Tyr Gly Glu Asn Lys Tyr Gln Ala Ile Gly Arg Glu Tyr
            260                 265                 270

Ser Leu Lys Glu Leu Lys Ser Pro Ser Lys Asp Lys Met Glu Arg Leu
        275                 280                 285

Lys Ala Leu Val Glu Ile Met Gly Ile Pro Cys Thr Ile Gly Ala Glu
        290                 295                 300
```

<210> SEQ ID NO 23
<211> LENGTH: 792
<212> TYPE: PRT
<213> ORGANISM: Klebsiella pneumoniae

<400> SEQUENCE: 23

```
Met Glu Gly Leu Thr Pro Arg Met Gln Arg Leu Arg Asn His Tyr Leu
1               5                   10                  15

Thr Val Arg Pro Ser Val Ser Ile Tyr Arg Ala Leu Ala Phe Thr Glu
                20                  25                  30

Val Val Lys Ala Asn Pro Gly Met Pro Thr Ile Leu Leu Arg Ala Lys
            35                  40                  45

Ala Phe Arg His Ala Cys Glu Thr Ala Pro Ile Leu Ile Gln Asp Asp
        50                  55                  60

Glu Leu Ile Val Gly His Pro Cys Gly Lys Pro Arg Ala Gly Ala Phe
65                  70                  75                  80

Ser Pro Asp Ile Ala Trp Arg Trp Val Arg Asp Glu Leu Asp Thr Met
                85                  90                  95

Ser Thr Arg Pro Gln Asp Pro Phe Glu Ile Ser Glu Ala Asp Lys Lys
            100                 105                 110

Thr Ile Arg Glu Glu Ile Val Pro Phe Trp Glu Gly Arg Ser Leu Asp
        115                 120                 125

Glu Ile Cys Glu Ala Gln Tyr Arg Glu Ala Gly Val Trp Ala Phe Ser
    130                 135                 140

Gly Glu Thr Phe Val Ser Asp Leu Ser Tyr His Gln Ile Asn Gly Gly
145                 150                 155                 160

Gly Asp Thr Cys Pro Gly Tyr Asp Val Leu Phe Thr Lys Gly Met
                165                 170                 175

Asn Gly Ile Lys Ala Asp Ala Glu Ala His Leu Ala Ser Leu Ser Met
            180                 185                 190

Glu Asn Pro Glu Asp Ile Asp Arg Ile Tyr Tyr Lys Ala Ala Ile
        195                 200                 205
```

-continued

```
Glu Thr Cys Glu Gly Val Val Asn Tyr Ala Arg Arg Ile Ala Ala His
    210             215             220
Ala Arg Glu Leu Ala Ala Lys Glu Gln Asn Ala Gln Arg Arg Ala Glu
225             230             235             240
Leu Leu Thr Ile Ala Glu Val Asn Glu Asn Val Pro Ala Asn Pro Pro
            245             250             255
Lys Thr Leu Gln Glu Ala Leu Gln Ser Ile Trp Thr Val Glu Ser Leu
        260             265             270
Phe Glu Ile Glu Glu Asn Gln Thr Gly Leu Ser Leu Gly Arg Val Asp
    275             280             285
Gln Tyr Cys Tyr Pro Met Phe Glu Ala Asp Ile Arg Glu Gly Arg Leu
290             295             300
Thr His Asp Thr Ala Leu Glu Leu Leu Gln Ala Phe Ile Ile Lys Cys
305             310             315             320
Ala Glu Leu Met Trp Met Ser Ser Glu Leu Gly Ala Lys Tyr Phe Ala
            325             330             335
Gly Tyr Gln Pro Phe Ile Asn Leu Thr Val Gly Gly Lys Arg Ser
        340             345             350
Gly Gly Asp Ala Cys Asn Asp Leu Thr Tyr Leu Ile Met Asp Ala Val
    355             360             365
Arg Phe Val Lys Val Tyr Gln Pro Ser Leu Ala Cys Arg Ile His Asn
370             375             380
Gln Ser Pro Gln Lys Tyr Met Glu Lys Ile Val Asp Val Val Lys Ala
385             390             395             400
Gly Met Gly Phe Pro Ala Cys His Phe Asp Asp Ser His Ile Lys Met
            405             410             415
Met Leu Arg Lys Gly Phe Asp Phe Glu Asp Ala Arg Asp Tyr Cys Leu
        420             425             430
Met Gly Cys Val Glu Pro Gln Lys Ser Gly Arg Ile Tyr Gln Trp Thr
    435             440             445
Ser Thr Gly Tyr Thr Gln Trp Pro Ile Ala Ile Glu Phe Val Leu Asn
450             455             460
Arg Gly Arg Met Val Leu Phe Asp Ser Tyr Gln Gly Leu Asp Thr Gly
465             470             475             480
Asp Leu Arg Asp Leu Arg Thr Phe Asp Glu Phe Asp Ala Ala Val Lys
            485             490             495
Gln Gln Ile Ala His Ile Val Arg Leu Ser Ala Ile Gly Thr Val Ile
        500             505             510
Ser Gln Arg Val His Arg Asp Val Ala Pro Lys Pro Leu Met Ser Leu
    515             520             525
Leu Val Glu Gly Cys Met Glu Ser Gly Lys Asp Val Ala Ala Gly Gly
530             535             540
Ala Met Val Asn His Gly Pro Gly Leu Ile Phe Ser Gly Leu Ala Thr
545             550             555             560
Tyr Val Asp Ser Met Ala Ala Ile Arg Lys Leu Val Phe Glu Glu Lys
            565             570             575
Lys Tyr Thr Leu Glu Gln Ile Arg Asp Ala Leu Leu Ala Asn Phe Glu
        580             585             590
Gly Tyr Glu Ala Leu Arg Arg Asp Cys Leu Asn Ala Pro Lys Tyr Gly
    595             600             605
Asn Asp Asp Asn Tyr Val Asp Gln Tyr Ala Leu Asp Ile Thr Glu Trp
610             615             620
Thr Glu Lys Glu Cys Arg Lys Tyr Lys Met Leu Tyr Ser Thr Leu Ser
```

```
            625                 630                 635                 640
His Gly Thr Leu Ser Ile Ser Asn Asn Thr Pro Ile Gly Glu Leu Thr
                    645                 650                 655

Asn Ala Thr Pro Asn Gly Arg Leu Ala Trp Met Pro Leu Ser Asp Gly
                660                 665                 670

Ile Ser Pro Thr Gln Gly Ala Asp Lys Gln Gly Pro Thr Ala Ile Ile
            675                 680                 685

Lys Ser Val Ser Lys Met Asn Val Glu Thr Met Asn Ile Gly Met Val
        690                 695                 700

His Asn Phe Lys Phe Leu Lys Gly Leu Leu Asp Thr Pro Glu Gly Arg
705                 710                 715                 720

His Gly Leu Ile Thr Leu Leu Arg Thr Ala Ser Ile Leu Gly Asn Gly
                    725                 730                 735

Gln Met Gln Phe Ser Tyr Val Asp Asn Glu Val Leu Lys Lys Ala Gln
                740                 745                 750

Gln Glu Pro Glu Lys Tyr Arg Asp Leu Ile Val Arg Val Ala Gly Tyr
            755                 760                 765

Ser Ala Tyr Phe Val Glu Leu Cys Lys Glu Val Gln Asp Glu Ile Ile
        770                 775                 780

Ser Arg Thr Val Ile Glu Lys Phe
785                 790
```

<210> SEQ ID NO 24
<211> LENGTH: 315
<212> TYPE: PRT
<213> ORGANISM: Klebsiella pneumoniae

<400> SEQUENCE: 24

```
Met Ile Ala Lys Gln Glu Leu Thr Gly Arg Ile Phe Asn Ile Gln Lys
1               5                   10                  15

Tyr Ser Ile Tyr Asp Gly Asp Gly Ile Arg Thr Leu Val Phe Phe Lys
                20                  25                  30

Gly Cys Asn Ile Arg Cys Pro Trp Cys Ala Asn Pro Glu Gly Leu Asn
            35                  40                  45

Ser Gln Phe Gln Val Met Phe Ser His Asp Lys Cys Ile Asn Cys Gly
        50                  55                  60

Asp Cys Val Ser Val Cys Pro Ala Gly Ile His Tyr Arg Ala Glu Glu
65                  70                  75                  80

Asn Gly Glu Met Lys His Phe Val Asp Arg Asn Lys Asp Cys Ile Gly
                85                  90                  95

Cys Arg Lys Cys Glu Glu Ile Cys Thr Gln Asn Ala Leu Asp Ile Met
            100                 105                 110

Gly Lys Asp Val Thr Val Ser Glu Leu Met Glu Ile Ile Met Gln Asp
        115                 120                 125

Tyr Asp Phe Tyr Ile Ser Ser Gly Gly Val Thr Ile Gly Gly Gly
    130                 135                 140

Glu Met Ser Leu Gln Thr Asp Phe Ala Val Ala Leu Phe Arg Glu Cys
145                 150                 155                 160

Lys Lys Met Met Ile Asn Thr Ala Val Glu Thr Gln Gly Thr Thr Pro
                165                 170                 175

Leu Ala Asn Tyr Gln Lys Leu Ala Pro Val Thr Asp Thr Phe Leu Phe
            180                 185                 190

Asp Ile Lys Gln Ile Asn Ser Glu His His Lys Ala Met Leu Gly Ile
        195                 200                 205
```

```
Gly Asn Glu Gly Ile Arg Arg Asn Leu Glu Trp Leu Val Asp Ser Gly
            210                 215                 220

Ala Asn Val Ile Val Arg Met Pro Leu Ile Arg Gly Tyr Asn Asp Ser
225                 230                 235                 240

Phe Asp Ala Ile Thr Gly Ala Ile Asp Tyr Val Gln Lys Leu Ala Lys
                245                 250                 255

Arg Gly Asn Ile Arg Arg Ile Asp Met Leu Pro Tyr His Gln Leu Gly
            260                 265                 270

Arg Lys Lys Tyr Glu Arg Leu Asp Met Pro Tyr Pro Ile Thr Gln Asp
        275                 280                 285

Pro Ser Tyr Ser Pro Asp Glu Leu Asp Arg Leu Glu Thr Phe Phe Arg
290                 295                 300

Gln Phe Asp Phe Asp Ile Arg Leu Val Arg His
305                 310                 315

<210> SEQ ID NO 25
<211> LENGTH: 789
<212> TYPE: PRT
<213> ORGANISM: Clostridioides difficile

<400> SEQUENCE: 25

Met Ala Arg Gly Thr Phe Glu Arg Thr Lys Lys Leu Arg Glu Glu Ser
1               5                   10                  15

Ile Asn Ala Glu Pro His Ile Ser Ile Glu Arg Ala Val Leu Met Thr
                20                  25                  30

Glu Ala Tyr Lys Lys Tyr Glu Gly Ser Val Glu Ile Pro Val Leu Arg
            35                  40                  45

Ala Leu Ser Phe Lys His Tyr Ile Glu Asn Arg Thr Leu Ser Ile Asn
50                  55                  60

Asp Gly Glu Leu Ile Val Gly Glu Lys Gly Asp Ser Pro Asn Gly Ala
65                  70                  75                  80

Pro Thr Tyr Pro Glu Ile Cys Cys His Thr Met Glu Asp Leu Glu Val
                85                  90                  95

Met His Asn Arg Asp Ile Ile Asn Phe Ser Val Ser Glu Glu Ala Arg
            100                 105                 110

Lys Ile His Lys Glu Glu Ile Ile Pro Phe Trp Lys Lys Arg Gln Thr
        115                 120                 125

Arg Asp Lys Ile Ile Asn Ala Met Thr Pro Glu Trp Leu Ala Ala Tyr
130                 135                 140

Glu Ala Gly Met Phe Thr Glu Phe Met Glu Gln Arg Ala Pro Gly His
145                 150                 155                 160

Thr Val Cys Gly Asp Thr Ile Tyr Lys Lys Gly Phe Leu Asp Leu Lys
                165                 170                 175

Lys Asp Ile Glu Ala Arg Leu Lys Glu Leu Asp Phe Leu Asn Asp Leu
            180                 185                 190

Asp Ala Tyr Asn Lys Lys Ala Asp Leu Glu Ala Met Ala Ile Ala Cys
        195                 200                 205

Asp Ala Met Val Ile Leu Gly Lys Arg Tyr Ala Glu Lys Ala Arg Gln
210                 215                 220

Met Ala Glu Glu Thr Asp Glu Ala Lys Lys Asp Leu Leu
225                 230                 235                 240

Ile Ala Glu Thr Cys Asp Val Val Pro Ala His Lys Pro Glu Thr Tyr
                245                 250                 255

His Gln Ala Ile Gln Met Tyr Trp Phe Val His Ile Gly Val Thr Thr
            260                 265                 270
```

```
Glu Leu Asn Ile Trp Asp Ala Phe Thr Pro Gly Arg Leu Asp Gln His
    275                 280                 285

Leu Asn Pro Phe Tyr Glu Arg Asp Val Glu Asn Gly Ile Leu Asp Arg
    290                 295                 300

Asp Arg Ala Gln Glu Leu Leu Glu Cys Leu Trp Val Lys Phe Asn Asn
305                 310                 315                 320

Gln Pro Ala Pro Pro Lys Val Gly Ile Thr Leu Lys Glu Ser Ser Thr
                325                 330                 335

Tyr Thr Asp Phe Ala Asn Ile Asn Thr Gly Gly Ile Asn Pro Asp Gly
            340                 345                 350

Gln Asp Gly Val Asn Glu Val Ser Tyr Ile Ile Leu Asp Val Met Asp
        355                 360                 365

Glu Met Lys Leu Ile Gln Pro Ser Ser Asn Val Gln Ile Ser Lys Lys
    370                 375                 380

Thr Pro Gln Lys Phe Leu Lys Arg Ala Cys Glu Ile Ser Arg Lys Gly
385                 390                 395                 400

Trp Gly Gln Pro Ala Phe Tyr Asn Thr Glu Ala Ile Val Gln Glu Leu
                405                 410                 415

Met Glu Ala Gly Lys Thr Ile Glu Asp Ala Arg Leu Gly Gly Thr Ser
            420                 425                 430

Gly Cys Val Glu Thr Gly Cys Phe Gly Lys Glu Ala Tyr Val Leu Thr
        435                 440                 445

Gly Tyr Met Asn Ile Pro Lys Ile Leu Glu Leu Thr Leu Asn Asn Gly
    450                 455                 460

Tyr Asp Pro Ile Ser Lys Lys Gln Ile Gly Ile Glu Thr Gly Asp Pro
465                 470                 475                 480

Arg Asn Phe Gln Ser Tyr Glu Glu Leu Phe Glu Ala Phe Lys Lys Gln
                485                 490                 495

Leu His Tyr Met Ile Asp Ile Lys Ile Glu Gly Asn Ala Val Ile Glu
            500                 505                 510

Asn Ile Cys Ala Lys His Met Pro Cys Pro Leu Met Ser Thr Ile Val
        515                 520                 525

Asp Asp Cys Ile Glu Lys Gly Lys Asp Tyr Gln Arg Gly Gly Ala Arg
    530                 535                 540

Tyr Asn Thr Arg Tyr Ile Gln Gly Val Gly Ile Gly Thr Ile Thr Asp
545                 550                 555                 560

Ser Leu Thr Ala Ile Lys Tyr Asn Val Phe Asp Lys Lys Phe Asp
                565                 570                 575

Met Asp Thr Leu Leu Lys Ala Leu Asp Ala Asn Phe Glu Gly Tyr Glu
            580                 585                 590

Ala Ile Leu Asn Leu Val Ser Asn Lys Thr Pro Lys Tyr Gly Asn Asp
        595                 600                 605

Asp Asp Tyr Ala Asp Glu Ile Met Gln Glu Ile Phe Asn Ala Tyr Tyr
    610                 615                 620

Asn Glu Val Thr Gly Arg Pro Thr Val Cys Gly Gly Glu Tyr Arg Val
625                 630                 635                 640

Asp Met Leu Pro Thr Thr Cys His Ile Tyr Phe Gly Glu Ile Met Gly
                645                 650                 655

Ala Ser Pro Asn Gly Arg Leu Cys Ala Lys Pro Val Ser Glu Gly Ile
            660                 665                 670

Ser Pro Glu Lys Gly Gly Asp Thr Asn Gly Pro Thr Ala Val Ile Lys
        675                 680                 685
```

```
Ser Cys Ala Lys Met Asp His Ile Lys Thr Gly Gly Thr Leu Leu Asn
    690                 695                 700
Gln Arg Phe Ala Pro Ser Val Val Gln Gly Glu Lys Gly Leu Asp Asn
705                 710                 715                 720
Met Ala Asn Leu Val Arg Ala Tyr Phe Asn Met Asp Gly His His Ile
                725                 730                 735
Gln Phe Asn Val Phe Asp Lys Asn Val Leu Leu Glu Ala Gln Lys Asn
            740                 745                 750
Pro Gln Asp Tyr Lys Asp Leu Ile Val Arg Val Ala Gly Tyr Ser Asp
        755                 760                 765
His Phe Asn Asn Leu Ser Arg Thr Leu Gln Asp Glu Ile Ile Gly Arg
770                 775                 780
Thr Glu Gln Thr Phe
785

<210> SEQ ID NO 26
<211> LENGTH: 302
<212> TYPE: PRT
<213> ORGANISM: Clostridioides difficile

<400> SEQUENCE: 26

Met Asn Pro Leu Val Ile Asn Leu Gln Lys Cys Ser Ile His Asp Gly
1               5                   10                  15
Pro Gly Ile Arg Ser Thr Val Phe Phe Lys Gly Cys Pro Leu Glu Cys
            20                  25                  30
Val Trp Cys His Asn Pro Glu Ser Gln Thr Tyr Thr Lys Gln Val Leu
        35                  40                  45
Tyr Asn Glu Glu Arg Cys Ser Lys Cys Glu Ala Cys Ile Asn Ile Cys
    50                  55                  60
Pro His Lys Ala Ile Tyr Lys Gly Glu Thr Lys Ile Cys Leu Asp Gln
65                  70                  75                  80
Asp Lys Cys Glu Phe Cys Glu Thr Cys Leu Asp Tyr Cys Val Asn Asn
                85                  90                  95
Ala Arg Glu Ile Val Gly Gln Glu Tyr Ser Val Arg Asp Leu Val Lys
            100                 105                 110
Glu Ile Glu Lys Asp Arg Ile Phe Tyr Glu Ser Gly Gly Gly Val
        115                 120                 125
Thr Leu Ser Gly Gly Glu Val Met Ala Gln Asp Met Asp Phe Ile Cys
    130                 135                 140
Gly Val Ile Asn Met Cys Lys Ser Lys Gly Ile His Val Ala Ile Asp
145                 150                 155                 160
Thr Cys Gly Tyr Ala Lys Ser Glu Asn Tyr Glu Arg Val Ala Lys Cys
                165                 170                 175
Ala Asp Leu Phe Leu Tyr Asp Ile Lys Leu Ile Asp Glu Asp Lys His
            180                 185                 190
Ile Lys Phe Thr Gly Lys Ser Asn Asp Leu Ile Leu Lys Asn Val Lys
        195                 200                 205
Ile Leu Ser Glu Leu Gly Ala Asn Ile Asn Ile Arg Ile Pro Leu Ile
    210                 215                 220
Val Gly Val Asn Val Asp Asp Glu Asn Leu Glu Val Lys Lys Met Ile
225                 230                 235                 240
Glu Phe Leu Lys Pro Leu Asn Ile Gln Ala Val Ser Leu Leu Pro Tyr
                245                 250                 255
His Asn Ile Gly Lys His Lys Tyr Asp Lys Ile Tyr Lys Lys Tyr Glu
            260                 265                 270
```

```
Gly Glu Glu Leu Gln Arg Pro Ser Glu Glu Lys Leu Glu Glu Ile Lys
            275                 280                 285

Arg Leu Phe Glu Ala Ser Asn Phe Asn Thr Lys Ile Gly Gly
        290                 295                 300

<210> SEQ ID NO 27
<211> LENGTH: 154
<212> TYPE: PRT
<213> ORGANISM: Escherichia coli

<400> SEQUENCE: 27

Met Asn Tyr His Gln Tyr Tyr Pro Val Asp Ile Val Asn Gly Pro Gly
1               5                   10                  15

Thr Arg Cys Thr Leu Phe Val Ser Gly Cys Val His Glu Cys Pro Gly
            20                  25                  30

Cys Tyr Asn Lys Ser Thr Trp Arg Val Asn Ser Gly Gln Pro Phe Thr
        35                  40                  45

Lys Ala Met Glu Asp Gln Ile Ile Asn Asp Leu Asn Asp Thr Arg Ile
    50                  55                  60

Lys Arg Gln Gly Ile Ser Leu Ser Gly Gly Asp Pro Leu His Pro Gln
65                  70                  75                  80

Asn Val Pro Asp Ile Leu Lys Leu Val Gln Arg Ile Arg Ala Glu Cys
                85                  90                  95

Pro Gly Lys Asp Ile Trp Val Trp Thr Gly Tyr Lys Leu Asp Glu Leu
            100                 105                 110

Asn Ala Ala Gln Met Gln Val Val Asp Leu Ile Asn Val Leu Val Asp
        115                 120                 125

Gly Lys Phe Val Gln Asp Leu Lys Asp Pro Ser Leu Ile Trp Arg Gly
    130                 135                 140

Ser Ser Asn Gln Val Val His His Leu Arg
145                 150
```